US009375398B2

(12) United States Patent
Dreher

(10) Patent No.: US 9,375,398 B2
(45) Date of Patent: Jun. 28, 2016

(54) PEPTIDES FOR SKIN REJUVENATION AND METHODS OF USING THE SAME

(71) Applicant: Neocutis SA, Pully (CH)

(72) Inventor: Frank Dreher, San Francisco, CA (US)

(73) Assignee: Neocutis S.A., Pully (CH)

( * ) Notice: Subject to any disclaimer, the term of this patent is extended or adjusted under 35 U.S.C. 154(b) by 87 days.

(21) Appl. No.: 14/202,418

(22) Filed: Mar. 10, 2014

(65) Prior Publication Data

US 2014/0309173 A1    Oct. 16, 2014

Related U.S. Application Data

(60) Provisional application No. 61/779,601, filed on Mar. 13, 2013.

(51) Int. Cl.
| A61K 38/06 | (2006.01) |
| A61K 38/07 | (2006.01) |
| A61K 38/05 | (2006.01) |
| A61K 8/64 | (2006.01) |
| A61Q 19/08 | (2006.01) |
| A61K 9/00 | (2006.01) |

(52) U.S. Cl.
CPC ............... *A61K 9/0019* (2013.01); *A61K 8/64* (2013.01); *A61K 9/0014* (2013.01); *A61K 38/05* (2013.01); *A61K 38/06* (2013.01); *A61K 38/07* (2013.01); *A61Q 19/08* (2013.01)

(58) Field of Classification Search
CPC ... A61K 38/00; A61K 38/1709; A61K 45/06; A61K 2300/00; A61K 38/05; A61K 38/06; A61K 38/07; A61K 8/64; A61K 9/0014; A61K 9/0019; C07K 14/775; A61Q 19/08
See application file for complete search history.

(56) References Cited

U.S. PATENT DOCUMENTS

| 5,503,776 | A | * | 4/1996 | Murase et al. ................. 252/397 |
| 6,372,717 | B1 | | 4/2002 | Greff |
| 6,620,419 | B1 | | 9/2003 | Lintner |
| 8,110,658 | B2 | | 2/2012 | Harris et al. |
| 2004/0132667 | A1 | * | 7/2004 | Lintner ........................... 514/18 |
| 2005/0008665 | A1 | * | 1/2005 | Batzer et al. ................... 424/401 |
| 2007/0237735 | A1 | | 10/2007 | Denommee |
| 2010/0272790 | A1 | * | 10/2010 | Morariu ......................... 424/450 |
| 2010/0311668 | A1 | * | 12/2010 | Farwick et al. ............... 514/18.8 |
| 2010/0311688 | A1 | | 12/2010 | Chapin et al. |
| 2011/0195102 | A1 | | 8/2011 | Van Den Nest et al. |

FOREIGN PATENT DOCUMENTS

| CN | 1810828 | A | * | 8/2006 | ............. A61K 38/00 |
| FR | 2668365 | A1 | * | 4/1992 | ............... A61K 7/48 |
| FR | 2810323 | A1 | | 12/2001 | |
| FR | 2946251 | A1 | | 12/2010 | |
| WO | WO-94/19325 | A1 | | 2/1994 | |
| WO | WO-95/12581 | A1 | | 5/1995 | |
| WO | WO-98/07744 | A1 | | 2/1998 | |
| WO | WO-00/15188 | A1 | | 3/2000 | |
| WO | WO-00/58347 | A1 | | 10/2000 | |
| WO | WO-01/64178 | A1 | | 9/2001 | |
| WO | WO-2004/028536 | A1 | | 4/2004 | |
| WO | WO-2004/064866 | A1 | | 8/2004 | |
| WO | WO-2004/099237 | A1 | | 11/2004 | |
| WO | WO-2005/048968 | A1 | | 6/2005 | |
| WO | WO-2007/143006 | A2 | | 12/2007 | |
| WO | WO-2007/143006 | A3 | | 12/2007 | |
| WO | WO-2007/146269 | A2 | | 12/2007 | |
| WO | WO-2007-146269 | A3 | | 12/2007 | |
| WO | WO-2009/068351 | A2 | | 6/2009 | |
| WO | WO-2009/068351 | A3 | | 6/2009 | |
| WO | WO-2010/082175 | A2 | | 7/2010 | |
| WO | WO-2010/082175 | A3 | | 7/2010 | |
| WO | WO-2010/083368 | A2 | | 7/2010 | |
| WO | WO-2010/083368 | A3 | | 7/2010 | |
| WO | WO-2010/136965 | A2 | | 12/2010 | |
| WO | WO-2010/136965 | A3 | | 12/2010 | |
| WO | WO-2010/136965 | A9 | | 12/2010 | |
| WO | WO-2011/109469 | A1 | | 9/2011 | |
| WO | WO-2012/164488 | A2 | | 12/2012 | |
| WO | WO/2012/164488 | A3 | | 12/2012 | |

(Continued)

OTHER PUBLICATIONS

English Tranaslation of Description of FR2668365, Patent Translate powered by EPO and Google, accessed May 15, 2015, pp. 1-6.*
English Tranaslation of CN1810828A, Google Translation, accessed May 15, 2015, pp. 1-4.*
Ameri, M. et al. (Feb. 2010,—published Dec. 15, 2009). "Parathyroid hormone PTH(1-34) formulation that enables uniform coating on a novel transdermal microprojection delivery system," Pharm Res 27(2):303-313.
Ansurudeen, I. et al. (Jul. 2012, e-published Mar. 24, 2012). "Carnosine enhances diabetic wound healing in the db/db mouse model of type 2 diabetes," *Amino Acids* 43(1):127-134.
Babizhayev, M.A. (Apr. 11, 2006, e-published Jan. 4, 2006). "Biological activities of the natural imidazole-containing peptidomimetics n-acetylcarnosine, carcinine and L-carnosine in ophthalmic and skin care products," Life Sci 78(20):2343-2357.

(Continued)

*Primary Examiner* — James H Alstrum Acevedo
*Assistant Examiner* — Erinne Dabkowski
(74) *Attorney, Agent, or Firm* — Mintz Levin Cohn Ferris Glovsky and Popeo, P.C.

(57) ABSTRACT

The invention provides compositions for stimulating the formation of one or more extracellular matrix components that contain a lipoaminoacid derivative of the tripeptide carnosine such as N-Octanoyl Carnosine. Also provided are compositions containing N-Octanoyl Carnosine in combination with selected tripeptide and/or tetrapeptides as well as pharmaceutical and/or cosmetic compositions containing such compositions. The invention further provides methods of using the compositions and compositions of the invention to treat, alleviate, and/or ameliorate a symptom, condition, disorder, or disease of the skin or mucosa, wherein the symptom, condition, disorder, or disease is associated with changes in extracellular matrix components.

15 Claims, 2 Drawing Sheets

(56) References Cited

FOREIGN PATENT DOCUMENTS

| WO | WO-2014/140890 A2 | 9/2014 |
|---|---|---|
| WO | WO-2014/140890 A3 | 9/2014 |

OTHER PUBLICATIONS

Babizhayev, M.A. (Nov. 2009). "Current ocular drug delivery challenges for N-acetylcarnosine: novel patented routes and modes of delivery, design for enhancement of therapeutic activity and drug delivery relationships," Recent Pat Drug Deliv Formul 3(3):229-265.
Barnett, G. (1972). *Cosmetics, Science and Technology*, vol. 1, 2nd Edition, Balsam et al.eds, pp. 32-42.
Barnett, G. (1972). *Cosmetics, Science and Technology*, vol. 1, 2nd Edition, Balsam et al.eds, pp. 72-73.
Bonod-Bidaud, C. et al. (Jul. 2012, e-published Mar. 22, 2012). "In vivo evidence for a bridging role of a collagen V subtype at the epidermis-dermis interface," J Invest Dermatol 132(7):1841-1849.
Bornstein, J. et al. (2007). "Involvement of Heparanase in the Pathogenesis of Localized Vulvodynia," International Journal of Gynecological Pathology 27:136-141.
Brinckmann, J. et al. (Jan. 1995). "Collagen synthesis in (sun-) aged human skin and in fibroblasts derived from sun-exposed and sun-protected body sites," J Photochem Photobiol B 27(1):33-38.
Burrows, L.J. et al. (Sep. 2012, e-published Jul. 12, 2012). "The Effects of Hormonal Contraceptives on Female Sexuality: A Review," J Sex Med 9(9):2213-2223.
Carpino, L.A. et al. (1990). "[(9-Fluorenylmethyl)oxy]carbonyl (FMOC) amino acid fluorides. Convienient new peptide coupling reagents applicable to the FMOC/tert-butyl strategy for solution and solid-phase syntheses," Journal of the American Chemical Society 112(26):9651-9652.
Cuzzocrea, S. et al. (2007). "Protective Effect of Orally Administered Carnosine on Bleomycin-Induced Lung Injury," Am J Physiol Lung Cell Mol Physiol 292:L1095-L1104.
Dang, C. et al. (Jan. 2003). "Fetal wound healing current perspectives," Clin Plast Surg 30(1):13-23.
Drafi, F. et al. (2010). "Carnosine inhibits degradation of hyaluronan induced by free radical processes in vitro and improves the redox imbalnce in adjuvant arthritis in vivo," Neuro Endocrinol Lett 31 Supplemental 2:96-100.
Farwick, M. et al. (Jul. 2011). "Bioactive tetrapeptide GEKG boosts extracellular matrix formation: in vitro and in vivo molecular and clinal proof," Exp Dermatol 20(7):600-604.
Fitzpatrick, D.W. et al. (Jan. 1982), "Carnosine, histidine, and wound healing," Surgery 91(1):56-60.
Gambichler, T. et al. (Feb. 2012). Differential expression of connective tissue growth factor and extracellular matrix proteins in lichen sclerosus, J Eur Acad Dermatol Venereol 26(2):207-212.
Goldstein, A. et al. (Apr. 2010). "Can oral contraceptives cause vestibulodynia?" J Sex Med 7(4 Pt 1):1585-1587.
Gorouhi, F. et al. (2010). "Topical Peptides and Proteins for Aging Skin," Chapter 101 in The Textbook of Aging pp. 1089-1117.
Guney, Y. et al. (2006, e-published Jan. 10, 2006). "Carnosine may reduce lung injury caused by radiation therapy," Med Hypotheses 66(5):957-959.
Hipkiss, A.R. (Aug. 1998). "Carnosine, a protective, anti-ageing peptide?," Int J Biochem Cell Biol 30(8):863-868.
Hipkiss, A.R. (May 2000). "A possible new role for the anti-ageing peptide carnosine," Cell Mol Life Sci 57(5):747-753.
Hipkiss, A.R. (Apr. 2009). "On the enigma of carnosine's anti-ageing actions," Exp Gerontol 44(4):237-242.
International Search Report mailed on Jan. 12, 2015 for PCT Application No. PCT/IB2014/001119, filed on Feb. 26, 2014, 4 pages.
Iriyama, S. et al. (Nov. 2010). "Heparanase activation induces epidermal hyperplasia, angiogenesis, lymphangiogenesis and wrinkles," Exp Dermatol 19(11):965-972.
Janssen, B. et al. (Aug. 2005). Carnosine as a protective factor in diabetic nephropathy: association with a leucine repeat of the carnosinase gene CNDP1., Diabetes 54(8):2320-2327.
Kahan, V. et al. (Nov. 2009, e-published Jun. 10, 2009), Stress, immunity and skin collagen integrity: evidence from animal models and clinical conditions, Brain Behav Immun 23(8):1089-1095.
Kellogg-Spadt, S. (Apr. 2010). "Vulvovaginal Atrophy," Adv Nurse Pract 18(4):31-32, 34, 55.
Kent, S.B.H. et al. (Jun. 10-15, 1984). "High Yield Chemical Synthesis of Biologically Active Peptides on an Automated Peptide Synthesizer of Novel Design," Peptides 1984, Proceedings of the 18$^{th}$ European Peptide Symposium, Djuronaset, Sweden, pp. 185-188.
Koppel, H. et al. (Dec. 2011, Jul. 12, 2011). "L-carnosine inhibits high-glucose-mediated matrix accumulation in human mesangial cells by interfering with TGF-β production and signaling," Nephrol Dial Transplant 26(12):3852-3858.
Kurdykowski, S. et al. (Jan. 5, 2012, e-published Oct. 31, 2011). "Ultraviolet-B irradiation induces epidermal up-regulation of heparanase expression and activity," J Photochem Photobiol B 106:107-112.
Leung, A. et al. (Jun. 2012). "Fetal wound healing: implications for minimal scar formation," Curr Opin Pediatr 24(3):371-378.
Lintner, K. (Jun. 2000). "Biologically active peptides: from a laboratory bench curiosity to a functional skin care product," Int J Cosmet Sci 22(3):207-218.
Lintner, Karl (2010). "Peptides and Proteins," Chapter 36 in Cosmetic Dermatology: Products and Procedures, Blackwell Publishing, pp. 292-301.
Maquart, F.X. et al. (Nov. 1993). "In vivo stimulation of connective tissue accumulation by the tripeptide-copper complex glycyl-L-histidyl-L-lysine-Cu2+ in rat experimental wounds," J Clin Invest 92(5):2368-2376.
Mccutcheon's Detergents and Emulsifiers (1986). North American Edition, pp. 317-324.
Merrifield, R.B. et al. (1963). "Solid Phase Peptide Synthesis. I. The Synthesis of a Tetrapeptide," J Am Chem Soc 85:2149-2154.
Merrifield, R.B. et al. (Dec. 1966). "Instrument for Automated Synthesis of Peptides," Analytical Chemistry 38(13):1905-1914.
Montalbetti, C. et al. (2005, e-published Sep. 19, 2005). "Amide bond formation and peptide coupling," Tetrahedron 61:10827-10852.
Morita, A. et al. (2009). "Molecular Basis of Tobacco Smoke-Induced Premature Skin Aging," Journal of Investigative Dermatology Symposium Proceedings 14:53-55.
Nagai, K. et al. (Nov. 1986). Action of Carnosine and Beta-Alanine on Wound Healing, Surgery 100(5):815-821.
Oikarinen, A. et al. (Nov. 1991). "New aspects of the mechanism of corticosteroid-induced dermal atrophy," Clin Exp Dermatol 16(6):416-419.
Olivieri, J. et al. (Dec. 2, 2010). Fibrillin assemblies: extracellular determinants of tissue formation and fibrosis, Fibrogenesis Tissue Repair 3(24), 8 pages.
Philips, N. et al. (2012, e-published Mar. 15, 2012). "Beneficial regulation of fibrillar collagens, heat shock protein-47, elastin fiber components, transforming growth factor-β1, vascular endothelial growth factor and oxidative stress effects by copper in dermal fibroblasts," Connect Tissue Res 53(5):373-378.
Pickart, L. et al. (2008). "The human tri-peptide GHK and tissue remodeling," J Biomater Sci Polymer Edn 19(8):969-988.
Quinn, P.J. et al. (1992). "Carnosine: its properties, functions and potential therapeutic applications," Mol Aspects Med 13(5):379-444.
Roberts, P.R. et al. (Mar. 1998). "Dietary peptides improve wound healing following surgery," Nutrition 14(3):266-269.
Schwartz, E. et al. (Dec. 1993). "Collagen alterations in chronically sun-damaged human skin," Photochem Phtobiol 58(6):841-844.
Seite, S. et al. (Sep. 2006). "Elastin changes during chronological and photo-ageing: the important role of lysozyme," J Eur Acad Dermatol Venereol 20(8):980-987.
Shu, YY. et al. (Oct. 1, 2011). "Estrogen and skin: therapeutic options," Am J Clin Dermatol 12(5):297-311.

(56) References Cited

OTHER PUBLICATIONS

Sok, J. et al. (May-Jun. 2008, e-published May 13, 2008). "Improvement of the dermal epidermal junction in human reconstructed skin by a new c-xylopyranoside derivative," Eur J Dermatol 18(3):297-302.

Soliman, K.M. et al. (2002). "Effects of Carnosine on Bilharzial Infestation in Hamsters: Biochemical and Histochemical Studies," Comparative Biochemistry and Physiology Part B 131:535-542.

Uitto, J. et al. (Dec. 2000). Cytokine modulation of extracellular matrix gene expression: relevance to fibrotic skin diseases, J Dermatol Sci 24 (Supplement 1):S60-S69.

Vizioli, M.R. et al. (1983). "Effects of carnosine on the development of rat sponge-induced granulation tissue. II. Histoautoradiographic observations on collagen biosynthesis," Cell Mol Biol 29(1):1-9.

Vizioli, M.R. et al. (1978). "Effects of carnosine on the development of rat sponge-induced granulation. I. General morphology and glycosaminoglycans histophotometry," Cell Mol Biol 23(3):267-273.

Vlieghe, P. et al. (Jan. 2010, e-published Oct. 30, 2009). "Synthetic therapeutic peptides: science and market," Drug Discov Today 15(1-2):40-56.

Zhang, L. et al. (Sep.-Oct. 2009). "Cosmeceuticals and peptides," Clin Dermatol 27(5):485-494.

\* cited by examiner

PEPTIDES FOR SKIN REJUVENATION AND METHODS OF USING THE SAME

RELATED APPLICATIONS

This application claims priority to U.S. Patent Application No. 61/779,601, filed Mar. 13, 2013, which is herein incorporated by reference in its entirety.

INCORPORATION-BY-REFERENCE OF SEQUENCE LISTING

The contents of the text file named "27894-507001US_ST25.txt", which was created on Jun. 30, 2014 and is 3 KB in size, are hereby incorporated by reference in their entireties.

FIELD OF THE INVENTION

This invention relates generally to the fields of skin rejuvenation of human skin, maintenance of healthy skin, restoration of damaged skin, wound healing, treatment of atrophy of any human tissue, and/or treatment of conditions, disorders, and diseases of the skin and mucosa associated with changes in extracellular matrix components. More particularly, the invention relates to compositions and methods of using such compositions in order to improve the appearance of aged skin by stimulating extracellular matrix components including, for example, collagens, elastin and hyaluronic acid in humans.

BACKGROUND OF THE INVENTION

Human skin is a complex organ which extends over the entire body. There are different types of skin at different portions of the body. For example, facial skin is different from that of the scalp, and even the skin on the palm of the hand is different than that on the back of the hand. Although the type of skin can vary over a person's body, skin is generally composed of two main layers of tissue. The epidermis, the outermost layer, is composed of several layers. The dermis, also called corium or cutis vera, is composed of a papillary layer above and a reticular layer below.

The human epidermis is principally composed of keratinocytes but contains also other types of cells including the melanocytes and the Langerhans' cells. Each of these cell types contribute, through their specific function, to the essential role played by the skin.

The dermis provides a solid support for the epidermis. It is also its feeder layer. The dermis consists mainly of fibroblasts but leukocytes, mast cells or tissue macrophages are also present. The dermis further contains blood vessels and nerve fibers. The acellular part (i.e., the area in between the cells) of the dermis is called extracellular matrix. The extracellular matrix of skin is composed of various extracellular components including proteins; in particular collagen fibers and elastin. Other extracellular matrix components of skin include glycosaminoglycans (e.g., hyaluronic acid, chondroitin sulfate, dermatan sulfate, keratan sulfate, heparan sulfate, etc.), proteoglycans (e.g., fibromodulin, decorin, biglycan, perlecan, heparan sulfate proteoglycan 2, agrin, versican, aggrecan, lumican, collagen type IX, collagen type XII, collagen type XIV, testican 1, testican 2, etc.) and various glycoproteins (e.g., fibrillin 1, thrombospondin-1 and -2, tenascin-C and -X, osteopontin, fibronectin, laminin-5 and -6, vitronectin, etc.). These extracellular components are synthesized by dermal fibroblasts, which make dermal fibroblasts the primary constituent in the structural assembly of the dermis.

The extracellular matrix is a highly heterogeneous amalgam of morphologically diverse architectural entities. It organizes and imparts structural integrity to individual tissues, in addition to modulating cell behavior by interacting with cell surface receptors and soluble growth factors. Dysfunctions and changes in components of the extracellular matrix can therefore interfere with both tissue integrity and cell performance. Dysfunctions and changes in components of the extracellular matrix of skin and mucosa in humans can lead to skin aging, skin atrophy, damaged skin, wounded skin, atrophy of vulva and vagina (vulvovaginal atrophy), or to any other conditions, disorders and diseases of skin and mucosa associated with changes in extracellular matrix components.

Therefore, a need exists in the art for compositions having improved activity that maintain or even increase the level of a rather large number of extracellular matrix components, including those that are altered in aged, damaged, wounded, atrophic skin, atrophy of vulva and vagina, or in any other conditions, disorders and diseases of skin and mucosa in humans associated with changes in extracellular matrix components.

SUMMARY OF THE INVENTION

The instant invention provides alternative peptidic compounds (i.e., peptides such as carnosine peptidic compounds and peptide derivatives and analogues) or appropriate peptidic combinations thereof (i.e., combinations of peptides, peptide derivatives and analogues), for the cosmetic and pharmaceutical uses.

In particular, provided herein are compositions for stimulating the formation of one or more extracellular matrix components (e.g., collagen I, collagen III, collagen V, collagen VI, collagen VII, collagen XVI, elastin, laminin, hyaluronic acid, fibrillin, heparan sulfate proteoglycan 2, and/or any combination(s) thereof).

For example, such compositions contain a lipoaminoacid derivative of the dipeptide carnosine where the amino-terminus is acylated. This lipoamino acid derivative may include, but is not limited to, Octanoyl Carnosine (also referred to interchangeably herein as N-Octanoyl Carnosine).

The chemical structure of Octanoyl Carnosine is provided below:

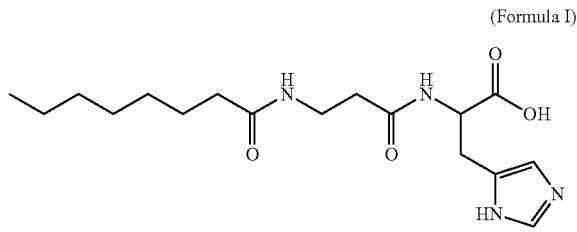

Octanoyl Carnosine (N-Octanoyl-beta-alanyl-histidine)

(Formula I)

Octanoyl Carnosine differs in structure and biological properties from carnosine. The chemical structure of carnosine is provided below:

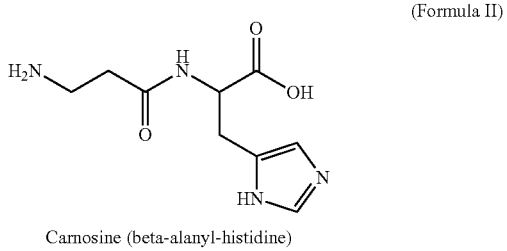 [SMILES: NCCC(=O)NC(Cc1cnc[nH]1)C(=O)O]

Carnosine (beta-alanyl-histidine)

Octanoyl Carnosine is a lipoaminoacid derivative of carnosine. Octanoyl Carnosine is not naturally occurring. Rather, Octanoyl Carnosine is a chemically modified carnosine where the amino-terminus (—NH2) of the dipeptide carnosine has been altered with an acylating agent to form an octanoyl group. This alteration of the amino-terminus provides significantly different physicochemical properties (e.g., molecular weight, diffusivity, water solubility, lipophilicity, octanol-water distribution coefficient, H-bond formation, etc.), chemical properties (e.g., chemical reactivity towards a chemical reactant, chemical stability, spontaneous hydrolysis, transformation by carnosinase, etc.), metabolic stability (i.e., proteolytic and/or enzymatic degradation), and biological properties (e.g., stimulation of extracellular matrix components including but not limited to collagens I and III; whether or not related to different enzyme kinetics, different affinities to cell surface or nuclear receptors, and/or increased diffusivity through cell membranes or other physiological barriers).

For example, being more lipophilic (i.e., higher octanol-water distribution coefficient) than carnosine provides Octanoyl Carnosine a higher permeability through mammal skin and therefore a higher potency than carnosine. For example, being more resistant to degradation (i.e., higher metabolic stability) than carnosine provides Octanoyl Carnosine a longer and more sustained potency than carnosine. For example, being a lipoaminoacid derivative of carnosine provides Octanoyl Carnosine the novel and unexpected biological properties to differently and more effectively stimulate the formation of extracellular matrix components; including but not limited to collagens I and III, as compared to carnosine.

The compositions of the invention may additionally include one or more carriers, excipients, and/or additional ingredients suitable for topical administration and/or subcutaneous administration.

The compositions of the invention are able to improve the general state of skin and/or mucosa, rejuvenate skin, treat damaged skin or mucosa, improve atrophic tissue including vulvovaginal atrophy, and/or treat other conditions, disorders and diseases of skin and mucosa associated with changes in extracellular matrix components in humans.

More specifically, the invention provides peptidic compositions, or appropriate combinations thereof, that are sufficiently effective to be used for the stimulation of the formation of collagen I, collagen III, collagen V, collagen VI, collagen VII, collagen XVI, elastin, laminin, hyaluronan synthase 2, fibrillin 1, heparan sulfate proteoglycan, and/or hyaluronic acid (or combinations thereof). Such compositions can be particularly used for the treatment of conditions, disorders and/or diseases of skin and mucosa associated with changes in extracellular matrix components in humans.

Even more specifically, the compositions of the invention stimulate the formation of one or more of the extracellular matrix components predominantly associated with skin aging (e.g., collagen I, collagen III, collagen V, elastin, hyaluronic acid, and/or any combination(s) thereof). Such compositions can be particularly used for the treatment of skin aging in humans.

Importantly, the compositions of the invention stimulate the formation of collagen III to a higher degree than the formation of collagen I. Determination of the degree of collagen III and/or collagen I formation is well within the routine level of skill in the art. Because these compositions stimulate the formation of collagen III, they can be particularly used for the treatment of wounded or damaged skin.

Any of the compositions of the invention can additionally contain one or more additional active ingredients, wherein the combination of all active ingredients stimulates the formation of hyaluronic acid. By way of non-limiting example, the one or more additional active ingredients may be tripeptides, tetrapeptides, and/or any combinations thereof. Specifically, the compositions may include Octanoyl Carnosine, in combination with the lipoaminoacid derivative of the tripeptide GHK (N-Palmitoyl-GHK), and the tetra-peptide GEKG (SEQ ID NO:1). Because these compositions (or appropriate combinations thereof) stimulate the formation of hyaluronic acid, they can be particularly used for the treatment of wounded or damaged skin, atrophic skin and mucosa, and vulvovaginal atrophy.

Unappreciated by the art and unexpectedly, it has been found that compositions containing the lipoaminoacid derivative of the dipeptide carnosine, N-Octanoyl Carnosine, stimulate the formation of extracellular matrix components such as collagen I, collagen III, collagen V, collagen VI, collagen VII, collagen XVI, elastin, laminin, hyaluronic acid, fibrillin, and/or heparan sulfate proteoglycan 2. In fact, compositions containing Octanoyl Carnosine stimulate the formation of the extracellular matrix components which are predominantly associated with skin aging, namely collagen I, collagen III, collagen VII, elastin and/or hyaluronic acid.

Furthermore, unappreciated by the art and most unexpectedly, compositions containing Octanoyl Carnosine stimulate the formation of significantly more collagen III than collagen I. Moreover, compositions containing Octanoyl Carnosine combined with selected additional tri- and tetra-peptides stimulate formation of hyaluronic acid in a synergistic manner.

Any of the compositions described herein may be suitable for topical administration in humans on skin aged skin, damaged skin, skin after cosmetic and/or dermatological procedures, atrophic skin, wounded skin, vulva, vagina, atrophic vulva, atrophic vagina, and/or on skin and mucosa associated with changes in one or more extracellular matrix components. Moreover, in some cases, these compositions may be suitable for subcutaneous administration in humans.

Compositions according to the invention that contain a combination of Octanoyl Carnosine, selected tripeptides, and selected tetrapeptides stimulate the formation of extracellular matrix components in skin or mucosa to a greater degree than any one or two of the active ingredients alone. For example, the combination of these ingredients produces synergistic results.

The invention provides compositions containing at least Octanoyl Carnosine. Optionally, the composition may contain Octanoyl Carnosine and at least one additionally substance (e.g., an acceptable carrier and/or excipient) suitable for topical application and/or for subcutaneous application.

The invention further provides a composition containing at least an N-acyl derivative of carnosine (other than Octanoyl Carnosine), an ester of Octanoyl Carnosine, an ester of carnosine, and/or any combination(s) thereof. Those skilled in the art will recognize that any of the compositions described herein can include Octanoyl Carnosine, any other N-acyl derivative of carnosine, an ester of Octanoyl Carnosine, an ester of carnosine, and/or any combination(s) thereof. These compounds are collectively referred to herein as "derivatives of Octanoyl Carnosine" or "Octanoyl Carnosine derivatives". The structure of suitable Octanoyl Carnosine derivatives that can be used in the compositions of the invention is provided below:

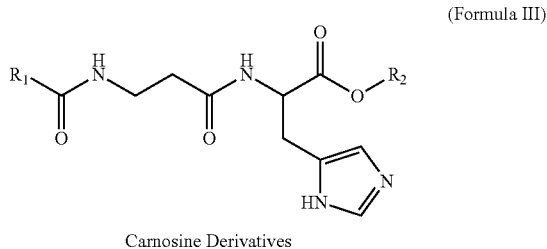

(Formula III)

Carnosine Derivatives wherein R1 is a carbon-containing side chain which can be linear or branched, saturated or unsaturated; and can contain heteroatoms including sulfur atoms (S), oxygen atoms (O), nitrogen atoms (N), phosphorus atoms (P), and/or halogen atoms (F, Cl, Br, I); and wherein R2 is either a proton atom (H), or a carbon-containing side chain which can be linear or branched, saturated or unsaturated; and can contain heteroatoms including sulfur atoms (S), oxygen atoms (O), nitrogen atoms (N), phosphorus atoms (P), and/or halogen atoms (F, Cl, Br, I).

Preferably, the R1 group is a linear, saturated carbon-containing side chain of —(CH2)n-CH3 whereas n is an integer number between 0 to 18. Preferably, the R2 group is either H, or a linear, saturated carbon-containing side chain of —(CH2)m-CH3 whereas m is an integer number between 0 to 19.

For example for Octanoyl Carnosine, R1=—(CH2)6-CH3 and R2=H. Octanoyl Carnosine is the most preferred derivative of carnosine for use in the compositions and methods of the invention.

Also provided are compositions containing at least Octanoyl Carnosine; in combination with the lipoaminoacid derivative of the tri-peptide GHK, N-Palmitoyl-GHK (also referred to interchangeably herein as Palmitoyl-GHK); and the tetra-peptide GEKG (SEQ ID NO:1). More specifically, also provided are compositions containing Octanoyl Carnosine, in combination with Palmitoyl-GHK, GEKG (SEQ ID NO:1), and at least one additional substance (e.g., carrier and/or excipient) suitable for topical application.

The invention also provides compositions containing at least Octanoyl Carnosine, an N-acyl derivative of carnosine other than Octanoyl Carnosine, an ester of Octanoyl Carnosine, and/or an ester of carnosine; in combination with Palmitoyl-GHK, an N-acyl derivative of GHK other than Palmitoyl-GHK, and/or an ester derivative of Palmitoyl-GHK; and GEKG (SEQ ID NO:1), an N-acyl derivative of GEKG (SEQ ID NO:1), an ester derivative of GEKG (SEQ ID NO:1), and/or an N-acyl GEKG (SEQ ID NO:1) ester.

Those skilled in the art will recognize that any of the compositions described herein can include Palmitoyl-GHK, an N-acyl derivative of GHK other than Palmitoyl-GHK, an ester derivative of Palmitoyl-GHK, and/or any combination(s) thereof. These compounds are collectively (and interchangeably) referred to herein as "derivatives of Palmitoyl-GHK" or "Palmitoyl-GHK derivatives.

Likewise, those skilled in the art will also recognize that any of the compositions described herein can include GEKG (SEQ ID NO:1), an N-acyl derivative of GEKG (SEQ ID NO:1), an ester derivative of GEKG (SEQ ID NO:1), an ester derivative of N-acyl GEKG (SEQ ID NO:1), and/or any combination(s) thereof. These compounds are collectively (and interchangeably) referred to herein as "derivatives of GEKG (SEQ ID NO:1)" or "GEKG (SEQ ID NO:1) derivatives".

In addition, those skilled in the art will also recognize that any of the compositions described herein can also include cyclic di-, tri, and/or tetrapeptides according to the invention. Cyclic peptides can be obtained by either linking side chains of the peptide or ends of the peptide sequence (head-to tail, N-backbone to N-backbone, end to N-backbone, end to side chain, side chain to N-backbone, side chain to side chain) through disulfide (disulfide-bond cyclization), lanthionine, dicarba, hydrazine or lactam bridges.

Any of the compositions described herein can also include di-, tri, and/or tetrapeptides according to the invention where the natural amino acid residue was substituted by unnatural amino acid (D-configuration), an N-methyl amino-alpha-amino acid, a non-proteogenic constrained amino acid, or a beta-amino acid.

Those skilled in the art will also recognize that any of the compositions described herein can also include di-, tri, and/or tetrapeptides according to the invention where the amid bond between two amino acids is replaced by NH-amide alkylation; or as further described in Drug Discovery Today 2010, 15, 40-56, or in other references known in the art.

Thus, the present invention relates to compositions containing Octanoyl Carnosine (or one or more derivatives thereof), formulated in combination with one or more additional substances, which can include, for example, an acceptable carrier and/or excipient suitable for topical application and/or for subcutaneous application. Optionally, any of the compositions described herein may also include one or more additional substances with biological activities.

In one aspect, the present invention provides compositions containing Octanoyl Carnosine (or one or more derivatives thereof) in combination with Palmitoyl-GHK (or one or more derivatives thereof) and GEKG (SEQ ID NO:1) (or one or more derivatives thereof) at a weight ratio of 4:1:5, formulated in combination with one or more additional substances which can include for example, a carrier and/or excipient suitable for topical application and/or subcutaneous administration. Optionally, such compositions may also include one or more additional substances with biological activities.

Preferably, the compositions of the invention contain at least Octanoyl Carnosine, Palmitoyl-GHK, and GEKG (SEQ ID NO:1) at a weight ratio of 4:1:5. However, those skilled in the art will recognize that other ratios of active ingredients can also be used and that determination of an appropriate weight ratio can be routinely determined.

Moreover, any of the compositions described herein can include between about 0.0001% to 10% per weight of Octanoyl Carnosine, depending on the solubility of Octanoyl Carnosine in the composition. Such compositions may also contain Octanoyl Carnosine, Palmitoyl-GHK, and GEKG (SEQ ID NO:1) (or one or more derivatives thereof) at a weight ratio of about 4:1:5, depending on the solubilities of Octanoyl Carnosine, Palmitoyl-GHK, and GEKG (SEQ ID NO:1) (or one or more derivatives thereof) in the composition.

For example, some compositions according to the invention contain about 0.004% per weight of Octanoyl Carnosine;

about 0.001% per weight of Palmitoyl-GHK, and about 0.005% per weight of GEKG (SEQ ID NO:1) along with one or more acceptable carriers or excipients suitable for topical administration in humans on skin, aged skin, damaged skin, skin after cosmetic and/or dermatological procedures, wounded skin, atrophic skin, atrophic mucosa, atrophic vulva, atrophic vagina, and/or for skin and mucosa associated with changes in extracellular matrix components.

The combination compositions will stimulate production of a biomolecule whereas application of either of Octanoyl Carnosine, the tripeptide Palmitoyl-GHK, or the tetrapeptide GEKG (SEQ ID NO:1) (or any derivatives thereof) alone would not or would stimulate production to a significantly lesser extent (e.g., amount) than the combination. Alternatively (or additionally), the combination compositions stimulate production of a greater extent of a biomolecule than that achieved from the peptides when added or administered individually. Indeed, in certain preferred aspects of the present invention, the combination of Octanoyl Carnosine, the tripeptide, and the tetrapeptide (or any derivatives thereof) produces synergistic results.

Also provided herein are pharmaceutical and/or cosmetic compositions and/or formulations containing any of the compositions of the invention along with one or more pharmaceutically and/or cosmetically acceptable carriers. In these pharmaceutical and/or cosmetic compositions and/or formulations, the composition may contain the combination of Octanoyl Carnosine, the lipoaminoacid derivative of the tripeptide GHK (i.e., N-Palmitoyl-GHK) and the tetra-peptide GEKG (SEQ ID NO:1). By way of non-limiting example, these components of the composition and/or formulation may be present at a weight ratio of 4:1:5.

The invention further provides kits containing, in one or more containers, any of the pharmaceutical and/or cosmetic compositions and/or formulations of the invention.

The compositions of the present invention are particularly suitable for skin rejuvenation or improving the appearance of aged skin. In addition, these compositions can also be used for maintaining healthy skin, restoring damaged skin, enhancing the restoration of skin after cosmetic and dermatological procedures, wound healing including scarless wound healing, treating atrophy of any human tissue including vulvovaginal atrophy, and for other conditions, disorders and diseases of skin and mucosa in humans associated with changes in extracellular matrix components.

These compositions for skin rejuvenation can be used for improving the appearance of aged skin, maintaining healthy skin, restoration of damaged skin, enhancing the restoration of skin after cosmetic and dermatological procedures, wound healing including scarless wound healing, treatment of atrophy of any human tissue including vulvovaginal atrophy, and for other conditions, and/or disorders and diseases of skin and mucosa in humans associated with changes in extracellular matrix components.

Certain aspects of the present invention also relate to the use of such compositions to make cosmetics, personal care products, feminine care products, hygiene products, dermatology products, pharmaceutical preparations, or medicaments for maintaining healthy skin, skin rejuvenation, restoration of damaged skin including, but not limited to, skin after cosmetic and dermatological procedures, wound healing, treatment of atrophy of any human tissue including vulvovaginal atrophy, and/or other conditions, disorders and diseases of skin and mucosa in humans associated with changes in extracellular matrix components.

This is accomplished by topical application of the composition of the invention to the skin or mucosa of the human needing such treatment. In some limited cases, this can be accomplished by subcutaneous administration of the composition of the invention in a human needing such treatment.

Certain aspects of the present invention also relate to methods of using such compositions to improve the state and appearance of human skin and to prevent and/or reduce the visible signs of aging and/or for enhancing the restoration of skin after cosmetic and dermatological procedures, as well as for enhancing wound healing, reducing the atrophy of any human tissue including vulvovaginal atrophy, and for improving other conditions, disorders and diseases of skin and mucosa in humans associated with changes in extracellular matrix components. These methods generally involve topically applying the composition to the affected skin or the affected mucosa when needed, in the amount and at the frequency best suited for the purpose. Methods of preventing, delaying the onset, or treating a skin or mucosal condition, disorder or disease are also contemplated.

Furthermore the present invention relates also to the use of Octanoyl Carnosine (or any derivatives thereof), or any peptide combinations with Octanoyl Carnosine (or any derivatives thereof), as active agents in medicine (i.e., active pharmaceutical ingredients) to make a medicament.

Among the additional advantages of using peptide Octanoyl Carnosine (or any derivatives thereof) and peptide combinations thereof, are the fact that the peptides are less toxic in comparison to the commonly used drugs for certain indications mentioned herein and that the peptides have fewer side effects, can be used for a long term treatment of conditions, disorders and diseases of skin and mucosa in humans associated with changes in extracellular matrix components, and can be easily administered as composition suitable for topical application. Moreover, no toxic or noxious degradation products of peptides are formed.

Furthermore, di-, tri-, and tetra-peptides are small (e g, contain only two to four amino acids) and have therefore the advantage of not being or being less immunogenic; in contrast to larger peptides (i.e., peptides containing of five or more amino acids) which can become immunogenic and cause allergic reactions. This makes the di-peptide Octanoyl Carnosine, the tri-peptide Palmitoyl-GHK and/or the tetra-peptide GEKG (SEQ ID NO:1) (or any di-, tri-, and tetra-peptide derivatives thereof) particularly suitable for human use.

Also, di-, tri-, and tetra-peptides are of a lower molecular weight (grams per mol) than the peptides consisting of five or more amino acids, which provides di-, tri-, and tetra-peptides with a smaller molecular volume than larger peptides, which enables di-, tri-, and tetra-peptides to better (i.e., faster, to a larger extent) absorb and penetrate skin, mucous membranes, cell membranes, and/or other physiological barriers. Thus, the di-peptide Octanoyl Carnosine, the tri-peptide Palmitoyl-GHK and/or the tetra-peptide GEKG (SEQ ID NO:1) (or any di-, tri-, and/or tetra-peptide derivatives thereof) are particularly suitable for topical application.

In particular, repeated topical application of Octanoyl Carnosine (or any derivatives thereof), or preferred combinations thereof with Palmitoyl-GHK and GEKG (SEQ ID NO:1) (or any derivatives thereof) in accordance to the present invention can offer the advantages and qualities described herein, as well as others which can be routinely determined. By way of non-limiting example, these advantages may include the ability (in some cases and with certain preferred combinations) to improve the visible signs of aging in human skin (including, for example, fine lines, wrinkles, skin folds, enlarged pores, roughness, dryness, loss of elasticity, loss of volume), improve other skin texture defects such as stretch marks (as caused by pregnancy, trauma or other influences), reduce bags under the eyes (also called "puffy eyes"), reduce dark (under eye) circles (both caused by thinning of the skin, insufficient blood circulation and slack tissue), and as well to reduce the severity of atrophic skin and mucosa including vulvovaginal atrophy. Moreover, some of these compositions have been discovered to have a benefit in wound healing and tissue regeneration.

Provided herein are methods of treating, alleviating, or ameliorating a symptom, condition, disorder, or disease of the skin or mucosa, wherein the symptom, condition, disorder, or disease is associated with changes in extracellular matrix components, the method comprising administering an effective amount of any of the compositions and/or formulations of the invention to a person (e.g., patient) in need thereof. For example, wherein the symptom, condition, disorder, or disease of the skin or mucosa associated with changes in extracellular matrix components is selected from the group consisting of wounds, aging, age-associated disorders and diseases, atrophy of any human tissue, disorders and diseases of vulvar tissue, disorders and diseases of vaginal tissue, and/or any combination(s) thereof.

In some examples, treating, alleviating, or ameliorating the wound results in scarless wound healing. In other examples, treating, alleviating, or ameliorating atrophy of any human tissue involves the treatment of vulvovaginal atrophy. In other examples, treating, alleviating, or ameliorating skin and mucosa associated with changes in extracellular matrix components comprises the treatment of vulvodynia, lichen sclerosus, vulvar lichens planus, erosive lichen planus, vulvar eczema, vulvar lichen simplex chronicus, ulcers of the vulva, Behcet's disease, vulvar intraepithelial neoplasia, and/or any combination(s) thereof.

Any of the methods described herein may involve repeated topical administration of any of the compositions and/or formulations described herein to the patient. By way of non-limiting example, the compositions/and or formulations may be administered to the patient at least once or twice a day for at least 30 days.

Alternatively, any of the methods described herein may involve repeated subcutaneous administration of any of the compositions and/or formulations described herein to the patient. By way of non-limiting example, the compositions/ and or formulations may be administered to the patient at least once or twice a day for at least 30 days.

Those skilled in the art will recognize that the administration of any of the compositions and/or formulations of the invention treats, alleviates, or ameliorates one or more visible signs of aging associated with changes in extracellular matrix components selected from the group consisting of fine lines, wrinkles, enlarged pores, roughness, dryness, loss of elasticity, loss of volume, atrophic skin, atrophic vulva, atrophic vagina, stretch marks, puffy eyes, dark (under eye) circles caused by thinning of the skin, dark (under eye) circles caused by insufficient blood circulation and slack tissue, and any combinations thereof.

Those skilled in the art will further recognize that the administration of any of the compositions and/or formulations of the invention treats, alleviates, or ameliorates conditions, disorders and diseases of skin and mucosa in humans associated with changes in extracellular matrix components which are not related to aging and which are selected from the group of wounded skin, damaged skin after cosmetic and dermatological procedures, atrophy of skin and mucosa due to other causes than aging (e.g., emotional stress, use of oral contraceptive pills, use of aromatase inhibitors, due to surgery, etc.), and for other conditions, and/or disorders and diseases of skin and mucosa in humans associated with changes in extracellular matrix components which are not related to aging.

Also provided are methods of improving or rejuvenating the appearance of skin comprising administering an effective amount of any of the compositions and/or formulations of the invention to a patient in need thereof. By way of non-limiting example, the compositions and/or formulations are administered to the patient in the form of a cosmetic, a personal care product, a feminine care product, a hygiene product, a dermatology product, a pharmaceutical preparation, a medicament, or any combination thereof. Such compositions and/or formulations can be administered topically to the skin or mucosa of the patient and/or subcutaneously to the patient.

The invention also provides methods of maintaining healthy skin or of preventing, ameliorating, or delaying aging of skin, the method by administering an effect amount of any of the compositions and/or formulations described herein to a patient in need thereof. For example, the compositions and/or formulations may be administered to the patient (i.e., topically to the skin or mucosa) in the form of a cosmetic, a personal care product, a feminine care product, a hygiene product, a dermatology product, a pharmaceutical preparation, a medicament, or any combination thereof. In such methods, administration of the compositions and/or formulations prevents, ameliorates, or delays the development of one or more signs of aging selected from the group consisting of fine lines, wrinkles, enlarged pores, roughness, dryness, loss of elasticity, loss of volume, atrophic skin, atrophic vulva, atrophic vagina, stretch marks, puffy eyes, dark (under eye) circles caused by thinning of the skin, dark (under eye) circles caused by insufficient blood circulation and slack tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
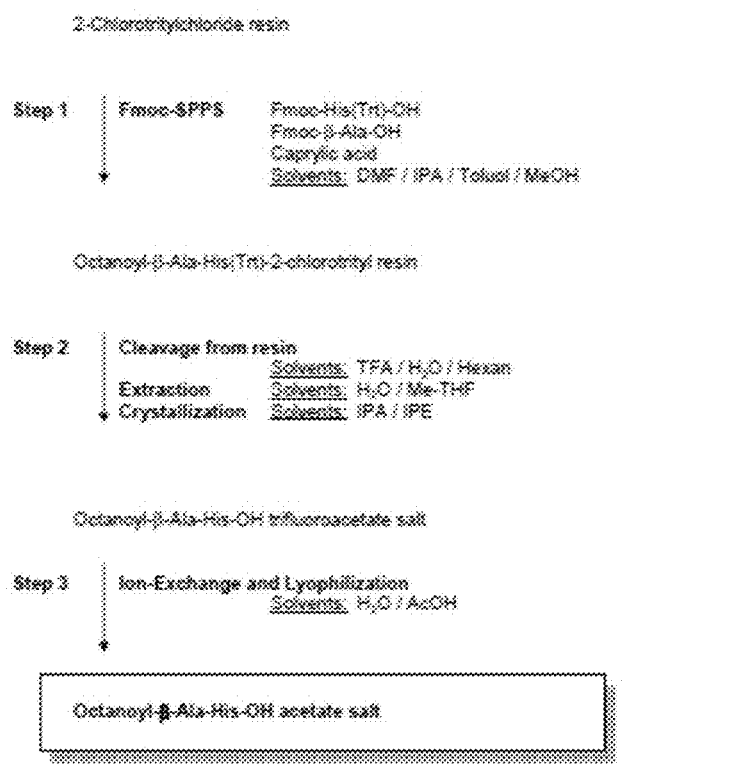
FIG. 1 is a schematic showing one way of the synthesis and purification of Octanoyl Carnosine (Octanoyl-beta-Ala-His-OH) in its acetate salt form by solid-phase synthesis.

The present invention will be better understood from the following description.

In this specification where reference is made to particular features of the invention it is to be understood that the disclosure of the invention in this specification includes all appropriate combinations of such particular features. The embodiments disclosed in this specification are exemplary and do not limit the invention. As used in this specification, the singular forms "a", "an", and "the" include plural reference unless the context clearly dictates otherwise. The terms "comprises" and "contains" and grammatical equivalents thereof are used in this specification to mean that, in addition to the features specifically identified, other features are optionally present. The term "at least" followed by a number is used herein to denote the start of a range beginning with that number.

This specification incorporates by reference all documents referred to herein and all documents filed concurrently with this specification or filed previously in connection with this application, including but not limited to such documents which are open to public inspection with this specification. All publications cited herein are hereby incorporated by reference in their entirety.

While the specification concludes with the claims particularly pointing and distinctly claiming the invention, it is believed that the present invention will be better understood from the following description. The terms "having" and "including" are to be construed as open-ended unless the context suggests otherwise.

Extracellular Matrix Components

Collagen occurs in many places throughout the body. So far, at least 28 types of collagen have been identified and described which provide a variety of structural and functional properties that collagen exhibits throughout the body. The five most common types are collagen I, II, III, IV and V. However, over 90% of the collagen in the body is of type I.

In human skin, collagen types I and III are the predominant types of collagen. They are present as fibrils and are responsible for the solidity and the strength of the dermis. Since type I collagen is the predominant collagen in adult human skin, comprising about 80% of the total bulk of collagen, it plays a major role in providing tensile strength to the skin. It is clear, however, that type III collagen, which comprises some 10% of the total dermal collagen, also plays a critical role in providing additional tensile properties to the skin and other tissues. (See Journal of Dermatological Science, 24, Suppl. 1, 2000, S60-S69).

Structurally, three collagen polypeptides wrap around each other in a helix to form a triple helix collagen I or III molecule. These molecules are packed in a five-stranded rope-like structure wherein each collagen molecule is quarter-staggered with respect to the next to form a microfibril. Microfibrils are subsequently wrapped around other microfibrils to form fibrils, which in turn wrap around other fibrils to produce even larger fibers.

Using histological and ultrastructural approaches in the past, it has been well-described that chronologically aged skin manifests in a reduced synthesis of both collagen types I and III. With respect to photoaging, Schwarz et al. (Photochem Photobiol 1993, 58, 841-844) demonstrated that the loss in collagen in sun-damaged human skin is due to increased degradation of both types I and III collagens. Additionally, it was shown that fibroblasts derived from sun-exposed skin synthesize a lower proportion of collagen III than cells from sun-protected skin. (See J Photochem Photobiol B. 1995, 27: 33-38).

Other collagen types are also present in skin, and a few of them have been described to change with skin aging. For instance, collagen VII, which is responsible for anchoring the basement membrane onto dermal matrix, decreases with aging. (See Eur J Dermatol 2008; 18: 297-302). One of the additional major morphological features of aged skin is an altered dermal epidermal junction which structurally manifests as flattening of the dermal epidermal junction outline with the loss of rete pegs and re-duplication of the lamina densa. Since the dermal epidermal junction is involved in the cohesion between the dermis and epidermis, age-related alterations in the dermal epidermal junction as a result of collagen VII decrease entail functional changes in skin resistance to mechanical stress and tissue homeostasis. This may contribute to wrinkle formation.

Collagen V assembles into diverse molecular forms and studies indicated that it is expressed in skin as different subtypes with important but distinct roles in matrix organization and stability. (See J Invest Dermatol 2012, 132: 1841-1849). Whereas collagen V is the defective product in most cases of classical Ehlers-Danlos syndrome, which is an extracellular matrix component disorder typically characterized by skin fragility and abnormal wound healing, it does not seem to significantly change with skin aging.

Further collagen types such as collagens VI, XIV and XVI are also expressed in the collagen-rich dermis. Although the structural features of these collagens are now well-characterized, their functions still remain mostly elusive.

The production of collagen in vivo requires activation of the collagen biosynthesis pathway by which transcription in the cell nucleus promotes polypeptide synthesis via translation from mRNA, organization of the polypeptides into a pro-collagen triple helix in the cytoplasm, secretion of pro-collagen from the cell, and then cleavage reactions, fibril assembly, and cross-linking extracellularly. Unlike many proteins that are stored in secretory granules and then secreted from the cell upon demand, collagen is secreted continuously.

Alterations in content and structure of collagen and other components of the extracellular matrix, including but not limited to, elastin and hyaluronic acid are characteristic of aged human skin.

Elastin is a vital component of the extracellular matrix of vertebrates, and provides exceptional properties including elasticity and tensile strength to many tissues and organs including the skin. Mature elastin is an insoluble and extremely durable protein that undergoes little turnover, but sustained exposure to proteases may lead to irreversible and severe damage, and thus to functional loss of the elastic fiber network. In general, elastin content decreased with age in sun unexposed skin (i.e., buttock) (i.e., elastin content decreased by about 44% between 50 and 70 years of age). A similar decrease was seen in severe sun-exposed skin (i.e., face) (i.e., elastin content decreased by about 31% between 50 and 70 years of age). Interestingly, the elastin content in moderately sun-exposed areas (i.e., forearm) did not significantly change during aging. This phenomenon might be explained by a combination of age-induced reduction and sun-dependent increase in elastin, what appears to be at least partially regulated by UV-induced deposition of lysozyme in elastin fibers. (See JEADV 2006, 20, 980-987).

Fibrillins (e.g., fibrillin 1) are ubiquitous glycoproteins of the extracellular matrix that self-polymerize into filamentous microfibrils in which individual molecules are organized in longitudinal head-to-tail arrays and associate laterally as well. (See Fibrogenesis & Tissue Repair 2010, 3, 24). Fibrillin microfibrils can additionally serve as the structural template for tropoelastin deposition and/or crosslinking during elastic fiber formation. Specific segments of the fibrillins interact in vitro with numerous extracellular signaling and cell surface molecules, including fibronectin, fibulins, syndecans and integrins. The multiple molecular interactions of fibrillins are believed to drive the assembly of morphologically distinct macroaggregates, which contribute to imparting the structural integrity to individual tissues and organs (structural role), and to target TGF-beta and BMP complexes to the architectural matrix, which contributes to instructing the behavior of cells (instructive role). TGF-betas and BMPs are potent modulators of extracellular matrix metabolism that are under the control of a complex network of relays and servo-mechanisms operating within and outside the cell, and at the cell surface. Thus, fibrillins are important components of the extracellular matrix which are necessary for the formation of other extracellular matrix components such as elastin and elastic fiber formation.

Hyaluronic acid (also called hyaluronan) is an anionic, non-sulfated glycosaminoglycan. It is unique among glycosaminoglycans since it is non-sulfated and can be very large, with its molecular weight (g mol-1) often reaching the millions. As a predominant voluminous molecule, hyaluronic acid is a major component of the extracellular matrix of the skin. It provides structure, volume (which is associated with hyaluronic acid's excellent water holding properties), and organization (e.g., facilitates the transport of ion solutes and nutrients) but also contributes significantly to cell proliferation and migration in the dermis. In addition, through the water-attaining properties of hyaluronic acid, it contributes to the hydration of the skin.

Glycosaminoglycans (e.g., hyaluronic acid, chondroitin sulfate, heparan sulfate, dermatan sulfate, keratan sulfate, etc.) and particularly hyaluronic acid are major components of the cutaneous extracellular matrix involved in wound healing and tissue regeneration. Wound healing is a dynamic interactive process involving many precisely interrelated phases, overlapping in time and leading to the restoration of tissue integrity. The healing process reflects the complex and coordinated body response to tissue injury resulting from the interaction of different cell types and extracellular matrix components. Hyaluronan plays a key role in each phase of wound healing by stimulating cell migration, differentiation, and proliferation as well as regulating extracellular matrix organization and metabolism. Glycosaminoglycans and particularly hyaluronic acid are also involved in skin aging.

As summarized by R. Stern in 2010 (Textbook of Aging Skin, Springer (incorporated herein by reference)), though dermal hyaluronic acid is responsible for most hyaluronic acid in skin, epidermal cells (e.g.; keratinocytes) are also able to synthesize hyaluronic acid. The most dramatic histochemical change observed in aged skin is the marked decrease in epidermal hyaluronic acid A. In skin of an elderly person, hyaluronic acid is still present in the dermis, while the hyaluronic acid of the epidermis has disappeared entirely. The reasons for this precipitous fall with aging are unknown. It has been described that the synthesis of epidermal hyaluronic acid is influenced by the underlying dermis, thereby indicating that epidermal hyaluronic acid is under separate controls from dermal hyaluronic acid.

In contrast with previous in vitro and in vivo observations, studies document that the total level of hyaluronic acid remains about constant in human skin with aging. However, the major age-related change is the increasing avidity of hyaluronic acid with tissue structures with the concomitant loss of hyaluronic acid extractability. Such intercalated hyaluronic acid may result in a diminished ability to take on water, what results in a decreased volume and, obviously, a loss in skin moisture. Progressive loss in the size of the hyaluronic acid polymer in skin as a function of age has also been reported. The increased binding of hyaluronic acid with tissue as a function of age parallels the progressive cross-linking of collagen and the steady loss of collagen extractability with age. Each of these phenomena contributes to the apparent dehydration, atrophy, and loss of volume and elasticity that characterizes aged skin.

Other than in skin aging, collagens I and III are also major extracellular matrix components involved in scar formation. Scarring occurs after trauma, injury or surgery to any tissue or organ in the body. Such scars are a consequence of a repair mechanism that replaces the missing normal tissue with an extracellular matrix consisting predominantly of collagen types I and III as well as fibronectin and some other extracellular matrix components. Scarring represents imperfect tissue regeneration. Whereas skin wounds on early mammalian embryos (e.g., up to about 24 weeks of gestation in humans) heal perfectly with no signs of scarring and complete restitution of the normal skin architecture, postnatal wounds heal with scars. (See Dang C et al., Clin Plast Surg 2003: 30, 13-23).

There are phenotypic differences between the collagen content and cross-linking patterns in fetal and postnatal wounds (See Clin Plast Surg 2003, 30, 13-23 and Curr Opin Pediatr 2012, 24, 371-378). In fetal wounds, type III collagen is rapidly deposited in a fine reticular network that is indistinguishable from uninjured skin. Post-natally, the ratio of type I to type III collagen in wounds increases. Of the many different types of collagen identified, fetal skin is known to contain a greater proportion of type III collagen, whereas adult skin consists predominantly of type I collagen. The predominance of type I collagen in postnatal wounds provides regenerating tissue with more strength and rigidity. Early scar formation in late gestation fetal wounds demonstrates larger collagen fibers with greater interfiber space.

In addition, fetal skin generally contains more hyaluronic acid than adult skin. Further, the hyaluronic acid content of the extracellular matrix in scarless fetal wounds is increased more rapidly than in adult wounds. Because fetal skin contains more hyaluronic acid than adult skin, several investigators have therefore proposed also a role of hyaluronic acid in scarless healing. The precise mechanisms of scarless healing remain unknown, however, despite the great increase in knowledge gained over the past decade.

The importance of extracellular matrix components collagen I, collagen III, collagen V, elastin and hyaluronic acid in the skin and the importance of maintaining, or even increasing, the amount thereof, thus, are self-evident for skin rejuvenation and maintaining healthy skin. In addition, collagen I, collagen III and hyaluronic acid have been particularly recognized to be important in wound healing and restoration of damaged skin without scar formation.

Conditions Associated with Changes in Extracellular Matrix Components

All terms such as "skin aging", "signs of skin aging", "topical application", and the like are used in the sense in which they are generally and widely used in the art of developing, testing and marketing cosmetic and personal care products, as well as for medicaments which are indicated for skin aging (e.g., cream with tretinoin).

Skin aging is classified into intrinsic aging and extrinsic aging depending on its cause. Intrinsic aging is a process by which the skin structure and the physiological functions of the skin deteriorate regardless of environmental changes as a human gets older. Extrinsic aging is caused by continuous exposure to external environment such as sunlight and air pollutants. Especially, skin aging caused by sun light is called photoaging. Ultraviolet (UV) light from the sun is the main cause of the physiological and morphological changes in aged skin.

As intrinsic skin aging proceeds, the skin becomes dry, and fine lines and wrinkles form which become more visible and deepen with age. Further, because of structural and functional changes of the epidermis and the dermis, the skin loses its elasticity and looks drooping. The dermis becomes thinner and well visible skin folds (e.g., nasolabial fold) form with age. It is estimated that the total quantity of collagen lost each year for adults is about 1%. In addition, the remaining collagen fibers gradually become thicker, while the cross-linking of the collagen fibers increases, so that the solubility, elasticity and like thereof decrease. Furthermore, elastin fibers become thicker and the cross-linking thereof also increases. Moreover, the proliferative activity of fibroblasts in the dermis decreases with time, and the ability of the aging fibroblasts to form (i.e., synthesize) new collagen, elastin, hyaluronic acid and other components of the extracellular matrix also decreases.

Continuous exposure to the sun is the main cause of extrinsic aging of skin. The UV component of sunlight, particularly UVA and UVB, is generally believed to be the principal causative agent in this process called photoaging. The extent of UV exposure required to cause "photoaging" is not currently known, although the amount sufficient to cause erythema (reddening, commonly described as sunburn) in human skin is quantified as the "minimal erythema dose" (MED) from a given UV light source. Repeated exposure to sunlight UV at levels that cause erythema and tanning are, nevertheless, commonly associated with photoaging.

There is a difference between the physiology of intrinsically-aged (i.e., chronologically-aged) skin in comparison with that of photoaged skin. Chronologically-aged skin typically maintains a smooth and unblemished appearance, in comparison with the leathery, blotchy, and often deep wrinkling of photoaged skin. Photoaging is characterized clinically by coarseness, wrinkles, mottled pigmentation, sallowness, laxity, telangiectasia, lentigines, purpura and relative ease of bruising, atrophy, depigmented areas, eventually premalignant, and ultimately malignant neoplasm (i.e., abnormal mass of tissue as a result of neoplasia, which is the abnormal proliferation of cells). Photoaging commonly occurs in skin that is generally exposed to sunlight such as the face, ears, bald areas of the scalp, neck, décolleté, forearms, and hands.

Although the typical appearance of photoaged and chronologically aged human skin can be readily distinguished, recent evidence indicates that chronologically aged and UV-irradiated skin share important molecular features including altered signal transduction pathways that promote matrix-metalloproteinase expression (e.g., collagenase, gelatinase) causing extracellular matrix degradation, decreased collagen formation, and alteration or damage to extracellular matrix of skin such as the accumulation of amorphous elastin-containing material residing beneath the epidermal dermal junction. This concordance of molecular mechanisms suggests that UV irradiation accelerates many key aspects of the chronological aging process in human skin.

Moreover, in women after menopause, the collagen amount and the skin thickness gradually decrease what causes a sensation of dry or tight skin and a marked increase in skin fine lines and wrinkles. In fact, in addition of wrinkling and loss of elasticity, aging of the skin is also associated with skin thinning (called atrophy) and delayed wound healing. These undesirable aging effects are exacerbated by declining estrogen levels in postmenopausal women. (See Am J Clin Dermatol 2011, 12, 297-311). Estrogens (e.g., 17-beta-estradiol) stimulate keratinocyte proliferation, leading to a thicker epidermis, and the formation of collagens and other extracellular matrix components. Estrogen products can be therefore used for the prevention and treatment of skin aging due to estrogen decline with menopause. Although topical estrogen products and systemic estrogen replacement therapy has been shown to improve some aspects of postmenopausal skin, long-term estrogen treatment has been associated with significant harmful systemic effects such as increase of breast cancer rate and cardio-toxic events). Therefore, a need for safe and effective, non-hormonal alternatives for the treatment of post-menopausal skin exists.

Furthermore, vulvar-vaginal atrophy (also called vulvovaginal atrophy) is another common consequence of menopause women. (See Adv Nurse Pract 2010, 18, 31-32, 34, 55). Vulvovaginal atrophy often manifests with discomfort what can be experienced as dryness, lack of lubrication, rawness, burning, irritation, inflammation, atrophic vaginitis, and pain. This can ultimately lead to sexual dysfunction. Today, hormone therapy is the only treatment approved by the US Food and Drug Administration for vulvovaginal atrophy. Because both physicians and women are concerned with the tolerability and safety profile of hormonal (i.e., estrogen, estrogen plus progestin) treatments, alternative, non-hormonal menopause therapies for the treatment of vulvar-vaginal atrophy are needed.

Vulvovaginal atrophy occurs most often after menopause, but it can also develop during breast-feeding, as a consequence of breast cancer treatment, or at any other time the women's estrogen production declines. Furthermore, recent evidence indicates that women taking oral contraceptives (which can cause a decline in the production of certain sex hormones such as testosterone) may also experience vulvovaginal atrophy. (See Sex Med 2012, 9, 2213-2223; Sex Med 2010, 7, 1585-1587). Vulvovaginal atrophy can lead to syndromes described as vulvodynia and vestibulodynia.

Vulvodynia is a pain syndrome that affects the vulvar area and often occurs without an identifiable cause or visible pathology. It refers to pain of the vulva unexplained by vulvar or vaginal infection or skin disease. Pain is the most notable symptom of vulvodynia, and can be characterized as a burning, stinging, irritation or sharp pain that occurs in the vulva, including the labia and entrance to the vagina. It may be constant, intermittent or happen only when the vulva is touched, but vulvodynia is usually defined as lasting for months to years. Symptoms of vulvodynia may occur in one place or the entire vulvar area. It can occur during or after sexual activity, when tampons are inserted, or when prolonged pressure is applied to the vulva, such as during sitting, bike riding, or horseback riding. Some cases of vulvodynia are idiopathic where no particular cause can be determined Vestibulodynia, or simply vulvar vestibulitis is vulvodynia localized to the vestibular region. It tends to be associated with a highly localized "burning" or "cutting" type of pain. The pain of vulvodynia may extend into the clitoris, which is referred to as clitorodynia. Vestibulodynia is the most common subtype of vulvodynia that affects premenopausal women—the syndrome has been cited as affecting about 10% to 15% of women seeking gynecological care.

Moreover, tissues from women with vulvodynia have been shown to have a significant increase in subepithelial heparanase activity what may lead to increased intraepithelial hyperinnervation as compared with healthy women. (See Int J Gynecol Pathol 2008, 27, 136-141). Heparanase, which is degranulated from mast cells, is capable of degrading the vestibular stroma and epithelial basement membrane, thus permitting stromal proliferation and intraepithelial extension of nerve fibers. Heparanase is an enzyme that acts within the extracellular matrix to degrade heparan sulfate. Heparan sulfate glycosaminoglycans (which are other examples of extracellular matrix components of skin) are abundant components of basement membranes and cell surfaces where they are present associated with specific core-proteins to form proteoglycans, mainly perlecan, glypicans and syndecans.

They play many roles such as modulation of cell proliferation and differentiation, cell-matrix adhesion and assembly. Heparan sulfate content has been also shown to be altered (decrease) during skin aging. This is mainly the result of an increased formation and activity of its degrading enzyme, heparanase (e.g., Hpse-1), due to UV-B irradiation. (See J Photochem Photobiol B, 2012, 106. 107-112). Heparanase activation and the consequent decrease of heparan sulfate are associated with wrinkle formation. (See Experimental Derm 2010, 19, 965-972).

Therefore, vulvodynia is a condition, disorder and disease of the vulva (which is composed of both keratinized and non-keratinized epithelial tissue) that can be also associated with changes in extracellular matrix components.

Vulvar lichen sclerosus, a chronic inflammatory disease which affects genital labial, perineal and perianal areas, is another disorder associated with changes in extracellular matrix components of the vulva. The histopathology of lichen sclerosus suggests abnormalities in extracellular matrix composition and in particular of proteoglycans. (See J Eur Acad Dermatol Venereol, 2012, 26, 207-212).

Vulvar lichen sclerosus produces significant discomfort and psychological distress in peri- and post-menopausal women. Other vulvar disorders associated with changes in extracellular matrix components include vulvar lichen planus, erosive lichen planus, vulvar eczema, vulvar lichen simplex chronicus, ulcers of the vulva, Behcet's disease, and vulvar intraepithelial neoplasia.

Finally, it is also accepted that emotional stress (see Brain Behav Immun 2009, 23, 1089-1095), tobacco smoke (see J Investig Dermatol Symp Proc 2009, 14, 53-55), air pollution, and certain medications (e.g., corticosteroids) (see Clin Exp Dermatol 1991, 16, 416-419) have an adverse effect on the skin and lead to changes (e.g., decreased formation and/or increased degradation) of collagen and other extracellular matrix components.

Compounds that Stimulate Formation of Extracellular Components

Numerous compounds including peptides that stimulate formation of extracellular matrix components have been reported in the scientific literature, issued patents, patent applications, or in other communications such as technical brochures from suppliers of those compounds. The chapter by F. Gorohhui and H. I. Maibach in the Textbook of Aging (2010, Springer (incorporated by reference)) discloses examples of such compounds; particularly peptides.

Peptides are preferentially used for the stimulation of the formation of extracellular matrix components for multiple reasons. They are not toxic, or less toxic than non-peptidic compounds, and no toxic or noxious degradation products of peptides are formed. Thus, peptides commonly have fewer side effects, and can be used for the long term treatment of conditions, disorders and diseases of skin and mucosa in humans associated with changes in extracellular matrix components. Di-, tri-, and tetra-peptides are particularly well suited for this purpose, as they have the advantage of not being immunogenic or of being less immunogenic, in contrast to larger peptides which can become immunogenic and cause allergic reactions. In addition, di-, tri-, and tetra-peptides are of a lower molecular weight than larger peptides what enables them to better (i.e., faster, in larger quantities) absorb and penetrate skin, mucous membranes, cell membranes, and/or other physiological barriers.

Furthermore, in contrast to natural extracts such as animal, plant or vegetable extracts, peptides can be obtained of a high purity (e.g., 95% and higher) with defined (e.g., the potential impurities are known and their content is within the specifications of the peptide product) and reproducible (e.g., from production batch to production batch) characteristics. Natural extracts cannot be obtained in a reproducible manner, frequently contain unknown impurities which vary from batch to batch, and can contain compounds which are not suitable for topical application since they cause skin irritation or sensitization in susceptible individuals. Also, natural extracts are frequently not stable and cause color and/or odor changes of the composition containing such extracts. This makes composition with natural extracts, which are known to stimulate the formation of extracellular matrix components, not useful for topical application.

The mechanisms of action of peptides are not always known. Stimulation of the formation of extracellular matrix components may be obtained with peptides acting, for example, on the skin's extracellular matrix, particularly by promoting the synthesis of molecules, by preventing their degradation, and/or by acting on receptors.

For example, patent application WO 2007/146269 discloses tetrapeptides that are characterized by the amino acid sequence motif GxxG (SEQ ID NO:2) or PxxP (SEQ ID NO:3), where G (glycine) and P (proline) residues are maintained and x is a variable amino acid. These disclosed sequences induce production of collagen from dermal fibroblasts as assessed by a dye-binding method designed for the analysis of soluble collagens released into the culture medium by mammalian cells during in vitro culture. While some of the disclosed peptides alone or in combination induced the synthesis of soluble collagen, none of the disclosed peptides induce the synthesis of any specific type of collagen (i.e., such as collagen I and/or III) or induce the synthesis of other extracellular matrix components.

Likewise, patent application WO 2009/068351 discloses tetrapeptides having the motifs GxxG (SEQ ID NO:2), PxxP (SEQ ID NO:3), or PxxK (SEQ ID NO:4). Preferred peptides disclosed in this application are tetrapeptides selected from the group of GEPG (SEQ ID NO:5), GPPG (SEQ ID NO:6), GEKG (SEQ ID NO:1), PGPP (SEQ ID NO:7), and/or PKEK (SEQ ID NO:8); or their N-acyl derivatives. While some of the disclosed peptides alone or in combination induce the synthesis of collagen I (alpha 1, or alpha 2), fibronectin 1, or hyaluronic acid synthetase 1, none of the disclosed peptides induce the synthesis of collagens III, hyaluronic acid, or other extracellular matrix components.

In a subsequent clinical study (see Exp Dermatol 2011, 20, 602-604), the tetrapeptide GEKG (SEQ ID NO:1) was further shown to stimulate hyaluronic acid formation after treatment with an oil-in-water vehicle containing 50 ppm GEKG (SEQ ID NO:1) for sixty days.

Another example is the tripeptide Gly-His-Lys (GHK), which is a fragment of collagen released during proteolysis of collagen, or may be derived from the extracellular matrix binding protein SPARC. Its copper complex (GHK-Cu) was studied for tissue remodeling and was shown to stimulate different components of the extracellular matrix including collagens I and III, elastin, and some glycosaminoglycans. (See J Biomater Sci Polymer Edn 2008, 19, 969-988). An in vivo study comparing GHK with GHK-Cu in rat experimental wounds revealed that GHK had no effect and only GHK-Cu leads to a statistical significant increase of collagen accumulation. (See J Clin Invest 1993, 92, 2368-2376). As shown in this study, only low and insignificant amounts of type III collagen were formed by GHK-Cu as compared to total collagen. Whereas higher doses of GHK-Cu produce skin irritation (see J Biomater Sci Polymer Edn 2008, 19, 969-988), GHK and its derivatives do not significantly stimulate collagen III formation, or stimulate collagen III to a significantly lesser extent than collagen I.

More recently, it was shown that the copper ion (Cu2+) stimulates both collagen I and III, but collagen III to a lesser extent than collagen I. (See Connective Tissue Res 2012, 53, 373-378). Therefore, the stimulation of collagen formation observed with GHK-Cu could originate from the copper ion and not from the GHK peptide. Copper is highly toxic and therefore not suitable for topical or subcutaneous uses. In addition to the Cu-GHK, the N-palmitoyl derivative of GHK (N-Palmitoyl-GHK) also stimulates collagen synthesis. (See Int J Cosmetic Sci 2000, 22, 207-218).

Patent FR2802413 discloses that N-Palmitoyl-GHK increases the collagen synthesis by up to 75.3% as judged from 3H-proline-incorporation experiments using human skin explants. In these studies, the collagen increase was due to formation of collagens I, IV and VII.

While some of these studies disclosed that GHK peptides and derivatives thereof induce the synthesis of collagens I and III and of a few other extracellular matrix components, none of the disclosed peptides induce the synthesis of collagen III more than collagen I. In fact, while GHK-Cu seems to stimulate some collagen III synthesis, those skilled in the art will recognize that it may be not suitable for prolonged topical application due to its intolerability and the toxicity related to copper.

As another example, patent application WO2005/048968 discloses that selected combinations of tripeptide GHK with tetrapeptide Gly-Gln-Pro-Arg (SEQ ID NO:9), or their analogues and derivatives, increase the synthesis of collagens I, IV, fibronectin and hyaluronic acid in vitro in a synergistic manner. However, none of the disclosed peptides, analogues and derivatives, or combinations thereof induces the synthesis of collagen III or of collagens V and VII.

Patent application WO 2007/143006 discloses polymeric bio-surfactants conforming to the formula Acyl-AA-Term where Acyl is an 8- to 22-membered carbon chain and AA is a consecutive sequence of four to nine amino acid residues, where at least one, preferably at least two of the amino acid residues is charged, and Term is an acid C-terminus or an amide C-terminus. While some of the disclosed polymeric bio-surfactants (alone or in combination) induce the synthesis of collagen I, fibronectin, and elastin, none of the disclosed compounds induces the synthesis of collagens III, hyaluronic acid, or other extracellular matrix components.

Moreover, patent application WO2010/082175 discloses specific peptides which significantly increase the formation of collagen I, III, IV, fibronectin, hyaluronic acid, and laminins. The peptide palmitoyl-KMO2K—OH increased the collagen I formation by 111% (as determined by ELISA) and the collagen III formation by 104% (as determined by immunofluorescence) in normal human dermal fibroblasts. Some of the disclosed peptides induce the synthesis of both collagen I and collagen III. However, none of the disclosed peptides induce the synthesis of collagen III more than collagen I or induce the synthesis of collagens V and VII, and other extracellular matrix components. In fact, also disclosed in WO2010/082175, the addition of a specific plant extract, *Portulaca pilosa*, to palmitoyl-KMO2K—OH is required to induce the synthesis of collagen III more than collagen I by the combination in a synergistic manner.

WO2010/136965 discloses dipeptides of the formula R1-Tyr-Arg-R2 which significantly increase the formation of elastin/tropelastin, fibrillin 1, and decorin in human dermal fibroblasts. However, none of the disclosed peptides, analogues and derivatives, or combinations thereof induces the synthesis of collagens, or other extracellular matrix components.

Other examples known in the art are tri-peptides with the formula K×K, which have been proposed as TGF-beta growth factor activators thereby enabling the synthesis of collagen in the skin extracellular matrix. For example, the tripeptide proposed in FR2810323 is elaidyl-KFK. However, in patent EP1625150 the inventors describe elaidyl-KFK as being insufficiently active to stimulate collagen synthesis and propose to alter the lysine side chains, for example the length of the aminated alkyl chains or to introduce specific side chains or to use a central amino acid X with a hydrocarbon chain possibly substituted by a hydroxyl group. Among the examples given are palmitoyl-KVK, palmitoyl-KAK or palmitoyl-KSK.

Also known in the art are peptides with trade names Kollaren® (INCI name: tripeptide-1), Collaxyl® IS (INCI name: hexapeptide-9), SYN®-TC (combination of palmitoyl-Lys-Val-Lys-Lys-OH with palmitoyl-Lys-Val-Thr-OH and tetradecylaminocarbonyl-Dab-Val-Dab) that significantly increase the formation of both collagens I and III in human dermal fibroblasts. However, none of these disclosed peptides, analogues and derivatives, or combinations thereof induce the synthesis of collagen III to a higher degree than the synthesis of collagen I. In addition, those other peptides are limited to the stimulation of only a few additional extracellular matrix components, most of which are not associated with skin aging. Moreover, these peptides either do not stimulate, only relatively weakly stimulate, and/or only partially stimulate the formation of the extracellular matrix components that have been described to be significantly altered with skin aging, namely collagen I, collagen III, collagen V, elastin, and hyaluronic acid. Moreover collagen III formation is either not stimulated by the peptides of the prior art, or, it is stimulated by the peptides to a lesser degree than collagen I formation. Thus, in contrast to the compositions of the instant invention, these peptides stimulate collagen I formation significantly more than collagen III formation.

Collagen III is an important component of the extracellular matrix. Both the formation and structure of collagen III are changed with aging, wounding or damaging of skin, as well as many conditions, disorders and diseases of skin and mucosa associated with changes in extracellular matrix components. Therefore, there is a need for compositions that effectively stimulate collagen III formation in skin and mucosa; for compositions that effectively stimulate collagen III without significantly stimulating collagen I formation; and/or for compositions that effectively stimulate collagen III significantly more than stimulating collagen I formation. Such compositions are particularly useful for scarless repair after wounding of skin as well as for optimal restoration of damaged skin.

More particularly, there is a need for compositions which stimulate collagen I, collagen III, collagen V, elastin and/or hyaluronic acid (e.g., all of the extracellular matrix components that are thought to be significantly altered with skin aging). There is also a need for compositions which stimulate extracellular matrix components such as fibrillins, which help in the formation of elastic fibers or other extracellular matrix components.

Preferably, the compositions of the present invention contain Octanoyl Carnosine (or one or more derivatives thereof). The compositions of the present invention include Octanoyl Carnosine (or one or more derivatives thereof) at concentration sufficient for demonstrating clinical efficacy for improving skin aging, or other skin disorders and diseases associated with skin aging.

The compositions of the present invention incorporate Octanoyl Carnosine (or one or more derivatives thereof) at concentration sufficient for demonstrating clinical efficacy for wound healing of skin, and/or for enhancing the restoration of skin after cosmetic and dermatological procedures. The compositions of the present invention can incorporate Octanoyl Carnosine (or one or more derivatives thereof) at concentration sufficient for demonstrating clinical efficacy for scarless wound healing of wounded skin.

In another example, the compositions of the present invention incorporate Octanoyl Carnosine (or one or more derivatives thereof) at concentration sufficient for demonstrating clinical efficacy for the treatment of aging vulvar and vaginal tissue.

In another example, the compositions of the present invention incorporate Octanoyl Carnosine (or one or more derivatives thereof) at concentration sufficient for demonstrating clinical efficacy for treating symptoms, disorders and diseases of the vulvar and the vaginal tissue which can be associated with vulvovaginal atrophy.

In yet another example, the compositions of the present invention incorporate Octanoyl Carnosine (or one or more derivatives thereof) at concentration sufficient for demonstrating clinical efficacy for treating vulvodynia.

In yet another example, the compositions of the present invention incorporate Octanoyl Carnosine (or one or more derivatives thereof) at concentration sufficient for demonstrating clinical efficacy for treating lichen sclerosus.

The compositions of the present invention incorporate Octanoyl Carnosine (or one or more derivatives thereof) at concentration sufficient for demonstrating clinical efficacy for treating other conditions, disorders and diseases of skin and mucosa in humans associated with changes in extracellular matrix components, including but not limited to the treatment of atrophy of any human tissue.

For example, the compositions of the invention contain Octanoyl Carnosine (or one or more derivatives thereof) at a concentration between 0.0001% to 10% Octanoyl Carnosine (or one or more derivatives thereof) per weight; depending on the solubility of Octanoyl Carnosine (or one or more derivatives thereof) in the composition.

The compositions may also contain selected tri-peptides (e.g., Palmitoyl-GHK) (or one or more derivatives thereof) and/or selected tetra-peptides (e.g., GEKG (SEQ ID NO:1)) (or one or more derivatives thereof). Preferably, the composition contains Octanoyl Carnosine, Palmitoyl-GHK, and GEKG (SEQ ID NO:1) (or one or more derivatives thereof) at a weight ratio of about 4:1:5. However, determination of other suitable weight ratios between these components is within the routine level of skill in the art.

When combining Octanoyl Carnosine (or one or more derivatives thereof) with both Palmitoyl-GHK (or one or more derivatives thereof) and GEKG (SEQ ID NO:1) (or one or more derivatives thereof), the optimal weight ratio of Octanoyl Carnosine (or one or more derivatives thereof) to Palmitoyl-GHK (or one or more derivatives thereof) to GEKG (SEQ ID NO:1) (or one or more derivatives thereof) is 4 parts Octanoyl Carnosine (or one or more derivatives thereof):1 part Palmitoyl-GHK (or one or more derivatives thereof):5 parts GEKG (SEQ ID NO:1) (or one or more derivatives thereof) (parts refer to parts per weight), as discovered during in vitro studies for hyaluronic acid formation (see Example 5, infra). Thus, one of the preferred compositions contains Octanoyl Carnosine (or one or more derivatives thereof), Palmitoyl-GHK (or one or more derivatives thereof) and GEKG (SEQ ID NO:1) (or one or more derivatives thereof) at a weight ratio of 4:1:5; whereas Octanoyl Carnosine is present in the compositions in proportions between 0.001% and 1%, in a carrier or excipient acceptable for topical application.

The combination of Octanoyl Carnosine, Palmitoyl-GHK and GEKG (SEQ ID NO:1) (or one or more derivatives thereof) at the weight ratio of 4:1:5 is not known in the art. The combination of Octanoyl Carnosine, Palmitoyl-GHK and GEKG (SEQ ID NO:1) (or one or more derivatives thereof) at the weight ratio of 4:1:5 stimulates the synthesis of hyaluronic acid at this specific weight ratio in synergistic and unexpected manner.

One or more additional ingredients, including one or more additional substances (e.g., acceptable carriers and/or excipients) suitable for topical application can also preferably be used in these compositions. The one or more additional ingredients may also include additional substances with biological activities (i.e., biologically active agents).

Also provided are methods for improving the state and appearance of human skin and reducing the signs of skin aging by using a composition containing Octanoyl Carnosine (or one or more derivatives thereof), or Octanoyl Carnosine (or one or more derivatives thereof) in combination with one or more additional selected tri- and/or tetra-peptides (or one or more derivatives thereof) according to the present invention, that stimulate the formation of extracellular matrix components.

The invention additionally provides methods of maintaining healthy skin and/or preventing skin aging by using a composition containing Octanoyl Carnosine (or one or more derivatives thereof), or Octanoyl Carnosine (or one or more derivatives thereof) in combination with selected tri- and/or tetra-peptides according to the present invention, that stimulate the formation of extracellular matrix components.

Additionally, the invention also provides methods of enhancing the restoration of skin after cosmetic and dermatological procedures, enhancing wound healing, reducing the atrophy of any human tissue including vulvovaginal atrophy, and improving other conditions, disorders and diseases of skin and mucosa in humans associated with changes in extracellular matrix components by using a composition containing Octanoyl Carnosine (or one or more derivatives thereof), or Octanoyl Carnosine (or one or more derivatives thereof) in combination with selected tri- and/or tetra-peptides according to the present invention, that stimulate the formation of extracellular matrix components.

In any of the method described herein, skin or skin cells (e.g., epidermal keratinocytes, dermal fibroblasts) are contacted (i.e., topically, subcutaneously, or by any other suitable method known in the art) with a composition containing Octanoyl Carnosine (or one or more derivatives thereof), or Octanoyl Carnosine (or one or more derivatives thereof) in combination with selected tri- and/or tetra-peptides. Additionally, the methods may also involve contacting (i.e., topically, subcutaneously, or by any other suitable method known in the art) mucosa (i.e., mucous membranes) or mucosal cells (i.e., epithelial cells) with a composition containing Octanoyl Carnosine (or one or more derivatives thereof), or Octanoyl Carnosine (or one or more derivatives thereof) in combination with selected tri- and/or tetra-peptides according to the present invention.

The compositions can be an aerosol, emulsion, liquid, lotion, cream, paste, ointment, foam, patch, microneedle device or any other cosmetic, dermatological and pharmaceutically acceptable formulation or device. Generally, an acceptable formulation for cosmetic, dermatological, and/or pharmaceutically use would include any acceptable carrier, excipient, and/or substance suitable for use on human skin or mucosa. The compositions may also contain one or more other biologically active agents including, but not limited to, retinoids, growth factors, and/or other peptides.

Any of the compositions of the present invention may also be used in combination with other cosmetic, skin care, feminine, hygiene, dermatological, pharmaceutical products, and/or medical devices.

The invention also provides methods of reducing scarring of skin damaged by normal aging, disease, injury, trauma, or by surgery or other medical procedures. Such methods can involve administering to the wound of a human a composition, wherein the composition contains any of the above-described peptides, singularly or in combination. The compositions may also be used in combination with other therapeutic agents, for example, such as tissue grafts, tissue culture products, oxygen or dressings.

The compositions of the invention can be used in humans. Alternatively, the composition may also be used in any kind of animal, preferably in mammals, and more preferably in cows, horses, cats, dogs, pigs, goats, or sheep.

Carnosine

As used herein, the term "carnosine" includes and encompasses the di-peptides beta-alanyl-histidine (see Formula II, supra) and all related compounds such as anserine (beta-alanyl-1-methyl-histidine) and homocarnosine (gamma-amino-butyryl-histidine). As used herein the term "carnosine" also includes D, L-carnosine, D-carnosine, L-carnosine, as well as salts thereof.

Carnosine's properties, functions and potential therapeutic applications have been extensively reviewed. (See P. J. Quinn et al. (Molec Aspects Med 1992, 13, 379-444) (incorporated herein by reference)). Although carnosine's anti-aging properties have previously been described, the properties of Octanoyl Carnosine have not previously been described and are surprising and unexpected. As reviewed by A. R. Hipkiss (Int J Biochem Cell Biol 1998, 30, 863-868; Cell Mol Life Sci 2000, 57, 747-753; Experimental Gerontology 2009, 44, 237-242 (incorporated herein by reference)), the naturally occurring dipeptide beta-alanyl-L-histidine (L-carnosine) is found in large amounts in long-lived tissues. It has protective functions in addition to its anti-oxidant and free-radical scavenging roles, and it extends cultured human fibroblast life-span, kills transformed cells, protects cells against aldehydes and an amyloid peptide fragment, and acts as an anti-glycating agent. More recently, carnosine was shown to protect against telomere shortening in cultured human fibroblasts and to extend the life-span of senescence-accelerated mice and *Drosophila* flies. Studies have revealed carnosine-induced upregulation of stress protein expression and nitric oxide synthesis, both of which may stimulate proteasomal elimination of altered proteins. As carnosine exerts anti-convulsant effects in rodents, the dipeptide may participate in the repair of protein isoaspartyl groups.

Carnosine has also been shown to promote healing of skin wounds, gastric and duodenal ulcers, as well as corneal and pulmonary wounds. (See Nutrition 1998, 14, 266-269; Molec Aspects Med 1992, 13, 379-444). For instance, it has been shown to accelerate healing of bleomycin-induced and irradiation-induced pulmonary wounds. (See Am J Physiol Lung Cell Mol Physiol 2007, 292, L1095-L1104; Med Hypotheses 2006, 66, 957-959). These effects of carnosine have been attributed to its affinity to quench free radicals. In dermal wounds, carnosine promotes granulation, increases the tensile strength and hydroxyproline content in the wound area. (See Surgery 91:56-60 (1982); Surgery 100:815-21 (1986)).

The observed effect has been ascribed to the histamine synthesis from histidine, one of the components of carnosine and the stimulation of collagen synthesis by beta-alanine, another component of carnosine.

Other investigations on the role of carnosine in the wound healing of surgical wounds have shown that carnosine is enhancing biosynthesis of glycosaminoglycans. (See Surgery 91:56-60 (1982); Cell Mol Biol Inc Cyto Enzymol 23:267-73 (1978); Cell Mol Biol 29:1-9 (1983)). Nagai et al. (Surgery 100: 815-821 (1986)) explain the mechanisms of action of carnosine in wound healing as beta-alanine induced collagen synthesis combined with histamine formation, which promotes granulation and results in a faster healing of the wound tissue.

In a more recent study of diabetic wound healing in a diabetic animal model (see Amino Acids 2012, 43:127-134), it was observed that daily injections and local application of carnosine significantly enhanced the expression of extracellular matrix components collagen I and smooth muscle actin, as well as certain growth factors. Carnosine treatment caused a significant increase in IGF1 expression in the wound area suggesting a direct or indirect modulation of IGF1 expression by carnosine enabling improved wound healing. Similarly, TGF-beta, which is well studied for its role in cutaneous wounds in various phases of wound healing, is significantly over-expressed in the wound tissue from carnosine-treated.

Apart from these effects, the wound healing potential of carnosine may also be due to its ability to alter the generation of free radicals and oxidative stress-induced prolonging of the inflammatory phase of the wound healing process in a diabetic wound. Since carnosine also shifts the acid-base balance to higher pH values, it can modify the wound micro-environment and block the activity of acid proteases and thereby enhance wound healing under hyperglycemic conditions.

In another recent study (see Neuro Endocrinol Lett 2010, 31 Suppl 2: 96-100), carnosine was shown to inhibit the degradation of hyaluronan induced by free radicals (hydroxy and peroxy-type radicals) in vitro. Importantly, as demonstrated in this study, and in contrast to the findings of the present invention using Octanoyl Carnosine (or one or more derivatives thereof) and combinations of Octanoyl Carnosine (or one or more derivatives thereof) with selected tri- and/or tetra-peptides, carnosine does not induce the formation of hyaluronan but, rather, limits its degradation through carnosine's antioxidant properties. Thus, the increase in glycosaminoglycans observed in earlier studies (see, e.g., Surgery 91:56-60 (1982); Cell Mol Biol Incl Cyto Enzymol 23:267-73 (1978); Cell Mol Biol 29:1-9 (1983)) is the result of a decreased degradation and not of an enhanced formation of glycosaminoglycans.

Carnosine was also shown to inhibit high-glucose-mediated matrix accumulation in human mesangial cells by interfering with TGF-β production and signaling. (See Nephrol Dial Transplant 2011, 26, 3852-3858). Under high-glucose conditions, deposition of collagen VI and fibronectin were increased, what was significantly inhibited on the protein and messenger RNA level by carnosine. TGF-β production increased under high-glucose conditions but was completely normalized by addition of L-carnosine.

Moreover, in a study investigating liver disorders induced by *Schistosoma mansoni* parasite in hamsters, subcutaneous administration of carnosine lowered the serum pro-collagen III peptide level in infested hamsters. (See Comp Biochem Physiol B Biochem Mol Biol 2002, 131, 535-542).

In diabetic nephropathy, carnosine inhibited the increased formation of fibronectin and collagen type VI in podocytes and the increased production of TGF-beta in mesangial cells induced by glucose. (See Diabetes 2005, 54, 2320-2327). Thus, carnosine protects against the adverse effects of high glucose levels on renal cells.

Therefore, all these effects (including carnosine's wound healing properties) can be attributed to carnosine's anti-oxidant properties, anti-glycation effects (in particular under hyperglycemic conditions), as well as the histamine synthesis from histidine as a component of carnosine, and/or stimulation of collagen I synthesis by beta-alanine, which is another component of carnosine.

In summary, carnosine has not been described to induce the formation of collagen III to a higher degree than collagen I, or to stimulate the formation of all extracellular matrix components that have been described to be significantly altered with skin aging, namely collagen I, collagen III, collagen V, elastin, and hyaluronic acid.

Octanoyl Carnosine and Other N-Acylated Derivatives of Carnosine

The term "N-Octanoyl Carnosine" (also referred to interchangeably herein as "Octanoyl Carnosine") in accordance with the present invention includes and encompasses all derivatives of carnosine where the amino-terminus of the di-peptide is acylated to form an octanoyl group. As used herein the term "Octanoyl Carnosine" includes octanoyl D,L-carnosine, octanoyl D-carnosine, octanoyl L-carnosine; as well as their salts. The terms Octanoyl Carnosine and N-Octanoyl Carnosine are synonyms that are used interchangeably herein. Octanoyl Carnosine can be produced by reaction of carnosine with octanoic acid (caprylic acid) under appropriate conditions. (See Example 1, infra).

Octanoyl Carnosine is an example of an N-acylated derivative of carnosine. N-Acylated derivatives of carnosine can be obtained after reacting the free amino-group (N-terminal amino group) of carnosine with an acylating agent under appropriate conditions known in the art of peptide synthesis. The acylating agent can be activated, using general techniques known in the art such as those described for example in "Amide bond formation and peptide coupling" (Tetrahedron 61(46), 10827-10852, 2005). Examples of activated acylating agents include, but are not limited to, acid chlorides, acid bromides, acid fluorides, symmetrical anhydrides, mixed anhydrides, carboxylic acids activated using common carbodiimides such as, but not limited to, diisopropylcarbodiimide (DIPCDI), N,N'-dicyclohexylcarbodiimide (DCC), 1-ethyl-3-(3'-dimethylamino-propyl)carbodiimide hydrochloride (EDC). Other non-limiting examples include carboxylic acids using the aforementioned carbodiimides and an additive, including, but not limited to, N-hydroxysuccinimide (HOSu), N-hydroxybenzotriazol (HOBt), 1-Hydroxy-7-azabenzotriazol, 6-chloro-N-hydroxybenzotriazol (HOAt), 3-Hydroxy-3,4-dihydro-4-oxo-1,2,3-benzotriazine (DhbtOH) or p-nitrophenol (PNP). Other examples include, but are not limited to, carboxylic acids activated with an uronium salt or a phosphonium salt, such as but not limited to, O-Benzotriazole-N,N,N',N'-tetramethyluronium hexafluorophosphate (HBTU), O-(Benzotriazol-1-yl)-N,N,N',N'-tetramethyluronium tetrafluoroborate (TBTU), 2-(6-Chloro-1H-benzotriazole-1,1,3,3-tetramethylaminium hexafluorophosphate (HCTU), 2-(6-Chloro-1H-benzotriazole-1-yl)-1,1,3,3-tetramethylaminium tetrafluoroborate (TCTU), 2-(1H-7-Azabenzotriazol-1-yl)-1,1,3,3-tetramethyluronium hexafluorophosphate (HATU), 2-(3,4-Dihydro-4-oxo-1,2,3-benzotriazin-3-yl)-N,N,N',N'-tetramethyluroniu-m hexafluorophosphate (HDBTU), 2-Succinimido-1,1,3,3-tetramethyluronium hexafluorophosphate (HSTU), N,N,N',N'-Tetramethyl-O-(succinimidyl)uronium tetrafluoroborate (TSTU), 2-(endo-5-norbornene-2,3-dicarboxymido)-1,1,3,3-tetramethyluronium hexafluorophosphate (HNTU), 1-benzotriazolyoxytris-(dimethylamino) phosphonium hexafluorophosphate (BOP) or benzotriazol-1-yl-oxytripyrrolidinophosphonium hexafluorophosphate (PYBOP).

Other activated acylating agents include, but are not limited to, esters of N-hydroxysuccinimide (NHS ester), p-nitrophenol (PNP ester), N-Hydroxy-5-norbornene-2,3-dicarboxylimide (HONB-ester), N-pentafluorophenol ester (PfP-ester), 2,4-dinitrophenyl ester, 4-nitrophenyl ester, 3-hydroxy-3,4-dihydro-4-oxo-1,2,3-benzotriazine (HODhbt), carbonyldiimidazole (CDI) or N-ethyl-5-phenyl-isoxazolium-3'-sulfonate (NEPIS), preferably a N-hydroxysuccinimide ester, p-nitrophenol or a HOBt ester or a derivative thereof using reaction conditions as, e.g., described in Organic Synthesis on solid Phase (Florencio Zaragoza Dorwald, Wiley-VCH Verlag GmbH, D-69469 Weinheim, 2000), Novabiochem Catalog (Merck Biosciences 2006/2007) and Fmoc Solid Phase Peptide Synthesis (Edited by W. C. Chan and P. D. White, Oxford University Press, 2000, ISBN 0-19-963724-5).

As known in the art, the same (or similar) methods of obtaining or producing N-acylated derivatives of carnosine can also be used to obtain N-acylated derivatives of other peptides, including but not limited to, the tri-peptide GHK, GHK esters, the tetra-peptide GEKG (SEQ ID NO:1), and GEKG (SEQ ID NO:1) esters.

N-Acetyl-Carnosine

The N-acetylated derivative of carnosine, N-acetylcarnosine, has previously been described for uses in ophthalmology. (See Recent Pat Drug Deliv Formul 2009, 3, 229-65). For instance, patent applications WO 2004/028536 A1; WO 94/19325; WO 95/12581; WO 2004/064866 A1 describe N-acetylcarnosine lubricant eye drops designed as 1% N-acetylcarnosine prodrug of L-carnosine containing a mucoadhesive cellulose-based compound combined with corneal absorption promoters in a drug delivery system for the management of age-related serious or disabling eye diseases in humans (age-related cataracts, ocular inflammation, age-related macular degeneration, macular dystrophies, ocular manifestations of diabetes, hypertonic retinopathy, primary open angle glaucoma, vitreous lesions).

Acetylation makes N-acetylcarnosine more resistant to degradation by carnosinase, an enzyme that breaks down carnosine to its constituent amino acids, beta-alanine and histidine. This results in the prolongation and potentiation of physiological responses to treatments with carnosine as anti-oxidant and anti-glycation agent. (See Life Sci 2006, 11, 78, 2343-57). For the prolongation and potentiation of the anti-oxidant protective effects to the cosmetic, therapeutic and medical treatments with carnosine, N-acetylcarnosine has also been proposed for the use in skin care products. (See Life Sci 2006, 78, 2343-2357).

As is true for N-acetylcarnosine, Octanoyl Carnosine is also highly resistant to hydrolysis by carnosinases and provides the antioxidant protective and anti-glycation effects characteristic for carnosine for a longer period of time as compared to unmodified carnosine.

N-acetylcarnosine has not been described to induce the formation of collagen III to a higher degree than collagen I or to stimulate the formation of all extracellular matrix components that have been described to be significantly altered with skin aging, namely collagen I, collagen III, collagen V, elastin, and hyaluronic acid.

Esters of Carnosine

Esters of carnosine include ester derivatives of carnosine which can be obtained after reacting the free carboxyl-group (free acid C-terminus) of carnosine with an esterifying agent under appropriate conditions known in the art of peptide synthesis. In one non-limiting method, an acidified alcohol solution is used for the esterification of carnosine. The method includes, for example, the use of an acidified alcohol such as methanolic HCl to generate a carnosine ester, e.g., carnosine methyl ester. Additionally, other alcohols (such as, for example, ethanol, propanol, or isopropanol) or substituted alcohols (such as, for example, aminoethanol) can be used to generate a reagent for esterification of the free acid C-terminus of carnosine.

Suitable alcohols for esterification of carnosine include but are not limited to organic chemicals with at least one hydroxyl group such as alkyl alcohols (e.g., C1 to C20 primary alcohols, C3 to C20 secondary alcohols), aryl alcohols (e.g.: benzyl alcohol), or poly-alcohols such as sugar alcohols (e.g., mono-, di-, poly-saccharides) or glycols and poly-glycols (e.g., glycerin, ethylene glycol, propylene glycol, PEGs, PPGs). Ascorbic acid is also a suitable agent (since it has at least one free hydroxyl group) useful for esterification with carnosine.

Any methods to obtain esters of carnosine known in the art can also be used to obtain esters of other peptides (including the esterification of free carboxyl groups of the peptides other than the free acid C-terminus) including, but not limited to, peptides GEKG (SEQ ID NO:1), N-Acyl-GEKG (SEQ ID NO:1), and/or N-Palmitoyl-GHK.

For example, PEGylation of carnosine, Octanoyl Carnosine, N-Palmitoyl-GHK,

GEKG (SEQ ID NO:1), and/or N-Acyl-GEKG (SEQ ID NO:1) is one preferred esterification method to prolong half-life, increase stability and provide higher water solubility of those peptides.

Peptides

The term "peptide" in accordance with the present invention is a compound that includes an uninterrupted sequence of at least two amino acids within its structure. The terms "di-peptide" or "dipeptide" as used herein refer to a compound that includes an uninterrupted sequence of two amino acids within its structure. The terms "tri-peptide" or "tripeptide" as used herein refer to a compound that includes an uninterrupted sequence of three amino acids within its structure. As used herein, a "tetra-peptide" or "tetrapeptide" is a compound that includes an uninterrupted sequence of four amino acids within its structure. These amino acids are indicated herein using a traditional one letter convention from left (N-terminal end) to right (C-terminal end). In this nomenclature, G is glycine, H is histidine, K is lysine, and E is glutamic acid.

The term "amino acid" as used herein includes and encompasses all of the naturally occurring amino acids, either in the D- or L-configuration if optically active, and the known non-native, synthetic, and modified amino acids, such as homocysteine, ornithine, norleucine and p-valine. A list of non-natural amino acids may be found in The Peptides, Vol. 5 (1983), Academic Press, Chapter VI, by D. C. Roberts and F. Vellaccio (incorporated herein by reference). The amino acids in the peptides of the present invention may be present in their natural L-configuration, unnatural D-configuration, or as a racemic mixture.

As used herein, the term "peptide" shall also refer to salts, deprotected forms, acylated forms of the peptide, deacylated forms of the peptide, enantiomers, diastereomers, racemates, prodrugs and hydrates of the above-mentioned peptide. Diastereomers of the peptide are obtained when the stereochemical or chiral center of one or more amino acids is changed. The enantiomer has the opposite stereochemistry at all chiral centers.

The term "prodrug" refers to any precursor compound which is able to generate or to release the above-mentioned peptide under physiological conditions. Such prodrugs are for instance larger peptides which are selectively cleaved in order to form the peptide of the invention. Further prodrugs are protected amino acids having especially protecting groups at the carboxylic acid and/or amino group. Suitable protecting groups for amino groups are the benzyloxycarbonyl, t-butyloxycarbonyl (BOC), formyl, and acetyl or acyl group. Suitable protecting groups for the carboxylic acid group are esters such as benzyl esters or t-butyl esters.

Peptides are synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. Peptides can be synthesized either by solid-phase peptide synthesis, by liquid-phase peptide synthesis, or by fragment condensation. In principle, the seemingly simple formation of a peptide bond can be accomplished using all the procedures available in organic chemistry for the synthesis of carboxylic acid amides. However, due to the presence of various functional groups in natural and unnatural amino acids and particularly the requirement for full retention of chiral integrity, the coupling of amino acids and peptides under mild conditions can be challenging. A plethora of coupling reagents has been developed suitability for specific applications (e.g., solid-phase peptide synthesis or fragment condensation). All coupling methods have the same reaction principle in common—after activation of the carboxyl group of the first amino acid, the second amino acid can form the peptide bond by a nucleophilic attack of its amino group. In order to prevent uncontrolled peptide bond formation the amino group of the first amino acid and all functional side chain groups need to be reversibly blocked. Repeated de-blocking, activation, and coupling build the peptide to its desired final sequence.

The general process for synthesizing peptides on solid-phase (e.g., resin) starts by attaching the first amino acid, the C-terminal residue, to the resin. To prevent the polymerization of the amino acid, the alpha amino group and the reactive side chains are protected with a temporary protecting group. Once the amino acid is attached to the resin, the resin is filtered and washed to remove byproducts and excess reagents. Next, the N-alpha protecting group is removed in a deprotection process and the resin is again washed to remove byproducts and excess reagents. Then the next amino acid is coupled to the attached amino acid. This is followed by another washing procedure, which leaves the resin-peptide ready for the next coupling cycle. The cycle is repeated until the peptide sequence is complete. Then typically, all the protecting groups are removed and the peptide resin is washed, and the peptide is cleaved from the resin.

The invention is further directed towards a method for producing the disclosed peptides. The peptides may be produced using any method known to those skilled in the art such as those disclosed in Merrifield, R. B., Solid Phase Peptide Synthesis I., J. AM. CHEM. SOC. 85:2149-2154 (1963); Carpino, L. A. et al., [(9-Fluorenylmethyl)Oxy]Carbonyl (Fmoc) Amino Acid Chlorides: Synthesis, Characterization, And Application To The Rapid Synthesis Of Short Peptides, J. ORG. CHEM. 37:51:3732-3734; Merrifield, R. B. et al., Instrument For Automated Synthesis Of Peptides, ANAL. CHEM. 38:1905-1914 (1966); or Kent, S. B. H. et al., High Yield Chemical Synthesis Of Biologically Active Peptides On An Automated Peptide Synthesizer Of Novel Design, IN: PEPTIDES 1984 (Ragnarsson U., ed.) Almqvist and Wiksell Int., Stockholm (Sweden), pp. 185-188, all of which are incorporated by reference herein in their entirety. Preferably, the peptides are manufactured by solid-phase synthesis. However, the peptides may also be manufactured using standard solution phase methodology.

Preferably, the peptides are in their trifluoroacetate (TCA) and/or acetate salt forms. However, the peptides can be in any other salt form including, but not limited to, adipate, ascorbate, alginate, benzoate, benzenesulfonate, bromide, carbonate, citrate, chloride, dibutyl phosphate, dihydrogen citrate, dioctyl phosphate, dihexadecyl phosphate, fumarate, gluconate, glucuronate, glutamate, hydrogen carbonate, hydrogen tartrate, hydro-chloride, hydrogen citrate, iodide, lactate, liponic acid, malate maleate, malonate, palmoate (embonate), palmitate, phosphate, salicylate, stearate, succinate, sulfate, tartrate, tannate, oleate, octyl phosphate; any other salts of the phosphate or carboxylate family; and/or any combination thereof. Under certain conditions, other salts can be derived from inorganic bases, include by way of example only, sodium, potassium, lithium, ammonium, calcium and magnesium salts. Salts derived from organic bases include, but are not limited to, salts of primary, secondary and tertiary amines.

The term "peptide", as used herein, includes proteins.

Skin Aging

"Signs of skin aging" include, but are not limited to, all outward visibly and tactilely perceptible manifestations as well as any other macro or micro effects due to skin aging. Such signs may be induced or caused by intrinsic factors (showing as chronological aged skin) and extrinsic factors (showing as environmental skin damage including but not limited photo-aged skin). These signs may result from processes which include, but are not limited to, the development of textural discontinuities such as wrinkles and coarse deep wrinkles, fine or skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

As used herein, prophylactically regulating a skin condition includes delaying, minimizing and/or preventing visible and/or tactile discontinuities in skin (e.g., texture irregularities in the skin which may be detected visually or by feel), including signs of skin aging. As used herein, therapeutically regulating skin condition includes ameliorating, e.g., diminishing, minimizing and/or effacing, discontinuities in skin, including signs of skin aging. Some of the compositions of the present invention may be used for prophylactically and/or therapeutically regulating a skin condition.

Some of the compositions of the present invention are useful for improving skin appearance and/or feel. For example, some preferred compositions of the present invention are useful for regulating the appearance of skin condition by providing an immediate visual improvement in skin appearance following application of the composition to the skin. Generally speaking, compositions of the present invention which further contain particulate materials will be most useful for providing the immediate visual improvement.

Demonstrating Clinical Efficacy

Prevention, amelioration, and/or treating of the signs of skin aging, protection and/or improving skin condition, and the prevention and/or treatment of skin imperfections are functional features which can be visualized, analyzed, measured and quantified using many techniques known by the specialist in cosmetic or skin rejuvenation treatments. Decrease of fine lines, wrinkles, skin folds, and of skin roughness can be quantified either directly on the person contact-free using fringe projection (FOITS=Fast Optical In vivo Topometry System; Dermatop™ or Primos™ system), or by silicon replicas of the skin area which are then analyzed by the technique called "drop shadows" or by a FOITS system, or by a Canfield VISIA™ device. Changes in volume and shape of the face can be quantified using a relief obtaining system without contact using a fringe projection FOITS system. Alteration of the skin barrier can be quantified by measuring transepidermal water loss (TEWL) using a Tewameter™, a Vapometer™, a Dermalab™, and/or an Aquaflux™ device. Loss of firmness and/or elasticity and/or tone and fatigue of the skin can be quantified using a Cutometer™, a Reviscometer™, an Aeroflexmeter™, a Dynaskin™, a Ballistometer™, a Twistometer™ and/or a Dermalab™ device. Dull complexion, loss of uniformity of skin tone, pigmentation changes (hypo and hyper pigmentation), local reddening, loss of clarity and brightness of the complexion, pigmentation spots, rosacea, dark circles are directly measurable using a Mexameter™, a Chromameter™, a Colormeter™, a Canfield VISIA™, a Canfield VISIA-CR™, a SIAscope™, a Goniolux™ or a confocal laser microscope device, and/or by specific color analysis on photo (enabled by the technique of photographing in polarized crossed and parallel light). The number and size of facial pores can be quantified by the silicon replica technology described above, or by specific analysis on photo (enabled by using a video microscope or a macroscopic photographing system). Atrophy and thinning of the skin, epidermis, dermis, or hypodermis (e.g., in case of studying slimming agents) is measurable by measuring TEWL (e.g., in case of studying the epidermis), or by an ultrasound echographic device, and/or a confocal laser microscope device. Density of skin fibers can be quantified by ultrasound and then by image analysis. Cellulite is quantified either directly by a relief obtaining system without contact using fringe projection (FOITS) or indirectly by measuring the length of the dermo-hypodermal junction by an ultrasound echographic device. Stretch marks are either directly quantified using a relief obtaining system without contact using fringe projection (FOITS) or by the silicon replica technology. Skin softness is directly measurable by techniques of friction study as with a frictiometer device or indirectly by the silicon replica technology. Changes in collagen, extracellular matrix components, and/or in connective tissue fibers may be quantified by histology, confocal laser microscopy, UV spectroscopy, SIAscopie, and/or by multiphoton spectroscopy. All changes visible to the eye (including but not limited to fine lines, wrinkles, folds, texture, sagging, loss of elasticity color, tone, pigmentation, redness) can be quantified in direct or on photography, by a trained judge person or not, with or without visual scoring system (e.g., using a 4-point severity scale).

Cosmetic Composition and Medicament

The terms "cosmetic composition" and "cosmetic product" are used interchangeably herein relate formulations that can be used for cosmetic purposes or purposes of hygiene or as a basis for delivery of one or more cosmetic and/or pharmaceutical substances, products, and/or ingredients.

The terms "pharmaceutical composition" and "medicament" is used herein to refer to a formulation that can be used for medical purposes or as a basis for delivery of one or more cosmetic and/or pharmaceutical substances, products, and/or ingredients.

It is possible that any of the formulations, compositions, medicaments, and/or products described herein can be used for two or more of these same purposes at one time.

Preferably, the compositions described herein are suitable for "topical application" (i.e., on top of skin surface, on top of mucosal surface). As used herein, topical application includes, but is not limited to, cutaneous; ocular; mucosal; buccal; vaginal; vulvar administration; administration onto skin, scar, keloid, scalp, eye, mouth, nose, vulva, vagina, rectum; and/or administration into a wound, ulcer, and granulation tissue.

The compositions may be suitable for administration to hair, and onto finger or toe nails. Alternatively, the compositions may be suitable for subcutaneous administration.

Cosmetic Product

A "cosmetic product," as used herein, include without limitation, personal care product, skin product, skin cream, skin gel, skin ointment, skin lotion, anti-aging product, skin rejuvenation product, skin conditioner, moisturizer, feminine product, hygiene product, skin patch, skin mask, tissue wipe, lipstick, mascara, rouge, foundation, blush, eyeliner, lip liner, lip gloss, lip balm, facial or body powder, sunscreens, sunblocks, nail polish, mousse, sprays, styling gels, nail conditioner, bath and shower gels, shampoos, conditioners, cream rinses, hair sprays, hair dyes and coloring products, soaps, body scrubs, exfoliants, astringents, depilatories and permanent waving solutions, antidandruff formulations, anti-sweat and antiperspirant compositions, shaving, preshaving and after shaving products, leave-on conditioners, deodorants, cold creams, deodorants, cleansers, rinses, vulvar product, vaginal product, or the like; whether in the form of creams, lotions, gels, ointments, macro-emulsions, micro-emulsions, nano-emulsions, serums, balms, colloids, solutions, liquids, suspensions, dispersions, compacts, solids, powders, pencils, spray-on formulations, brush-on formulations, patches, iontophoretic patches, microprojection patches, microneedle patches, skin delivery enhancing systems, bandage, tissue cloths, wipes, masks, aerosols, pastes, soap bars, cosmetic devices, and/or any other forms readily known to those skilled in the art.

Medicament

A "medicament," as used herein, include without limitation pharmaceutical preparations, carriers for dermatological purposes, including topical and transdermal application of pharmaceutical ingredients. These can be in the form of creams, lotions, gels, ointments, macro-emulsions, micro-emulsions, nano-emulsions, serums, balms, colloids, solutions, liquids, suspensions, dispersions, compacts, solids, powders, pencils, spray-on formulations, brush-on formulations, patches, iontophoretic patches, microprojection patches, microneedle patches, skin delivery enhancing systems, bandages, tissue cloths, wipes, masks, aerosols, pastes, soap bars, medical devices, and/or any other forms readily known to those skilled in the art.

Suitability for Topical Application

The term "acceptable substance(s) for topical application", as used herein, mean that the composition(s) comprising "acceptable substance(s) for topical application" according to the invention are suitable for use in contact with human skin and/or human mucosa; where the skin or the mucosa can be healthy, newborn, young, old, aged, appear visually different than normal, damaged, photo-damaged, sunburned, wrinkled, pathologic, diseased, wounded, atrophic, irritated, compromised, treated with cosmetic product(s), treated with pharmaceutical product(s), treated with cosmetic procedure (s), treated with dermatological procedure(s), treated with a pharmaceutical or medical device(s), surgically treated, etc. and are absent of significant (consumer-unacceptable) local intolerabilities to skin or mucosa (i.e., corrosivity, irritation, allergy), and the like after repeated topical application for cosmetic, skin care, feminine, or similar uses; or with maximally low and acceptable (consumer-acceptable) local intolerabilities to skin or mucosa skin irritation (i.e., irritation, allergy), and the like after repeated topical application for medical uses of the composition.

Local tolerability (e.g., irritation and allergy to skin; also called contact dermatitis and allergy) in humans can be determined by acute (1 day) and repetitive (4 to 21 days) patch testing on the back of humans, and/or during in use tests where the composition is used as indicated (e.g., for topical use on face, vulva, vagina, mucosal surface, and/or other body surface areas; or for wound healing). In case of a medication, safety studies generally also include animal studies.

Furthermore, acceptable substance(s) for topical application means that the compositions comprising "acceptable substance(s) for topical application" in accordance with the present invention are without significant physicochemical instability (e.g., significant changes in color, odor, viscosity, pH, and/or appearance) in the final packaging (e.g., bottle, tube, pump, jar, airless container, spray, patch, etc.) during the shelf-life of the product according to the recommended storage conditions of the product. Significant physicochemical instability means, that the color, odor, viscosity, pH, or the appearance changed (increased, decreased) more than 10% from the time when the composition was prepared and filled into the final packaging.

Any of the compositions of the present invention may also provide good aesthetics and be cosmetically elegant.

Acceptable substances for topical application or administration may include suitable excipients and/or carriers known in the art.

Additional Substances

The compositions described herein preferably include Octanoyl Carnosine (or one or more derivatives thereof), optionally in combination with at least one additional substance suitable for topical application and/or subcutaneous application. Additional substance(s) can be inert (e.g., carriers and/or d excipients) or can be with biological activities (i.e., biologically active agents and/or active pharmaceutical ingredient). Preferably, the compositions of the invention may also include additional biological active agents, including, but not limited to, peptides other than Octanoyl Carnosine, N-Palmitoyl-GHK, and GEKG (SEQ ID NO:1) (or one or more derivatives thereof) according to the present invention.

The terms "substance", "ingredient", "agent" and the like are used interchangeably herein.

The compositions of the invention may include one or more substances, various, conventional or not, which will provide some benefit to the object of the composition. More specifically, the combination of Octanoyl Carnosine (or one or more derivatives thereof) according to the present invention with selected additional ingredients may lead to an enhanced efficacy as compared to the use of the Octanoyl Carnosine (or one or more derivatives thereof) alone. The enhanced efficacy can be additive (the sum of efficacies of the individual agents alone), or it can be synergistic (larger than the sum of efficacies of the individual agents alone). Of course, the decision to include an additional ingredient and the choice of a specific ingredient depends on the specific use of the composition and the product formulation and is well within the routine level of skill in the art.

In particular examples, the compositions of the present invention may contain a wide range of additional ingredients. The 2012 International Cosmetic Ingredient Dictionary & Handbook, 14th Edition, as well as the Cosmetic Bench Reference—Directory of Cosmetic Ingredients (published by Cosmetics & Toiletries) describes a wide variety of non-limiting cosmetic and pharmaceutical ingredients commonly used in the skin care, personal care, feminine care, and dermatology and pharmaceutical industry, which are available for use in the present invention. Additional examples can be found in the books provided by the United States Pharmacopeia (USP), the National Formulary (NF), and other references for cosmetic and pharmaceutical ingredients known in the art. Each of these references is herein incorporated by reference in its entirety. This information is regularly updated by the addition of new ingredients.

Exemplary functional classes of such ingredients are, but are not limited to, abrasive agent, absorbent powder, absorption base, acidulent, activator, adhesion promoter, agent modulating cell differentiation, agent modulating cell proliferation, agent stimulating synthesis of dermal or epidermal macromolecules, agent preventing degradation of dermal or epidermal macromolecules, agent acting on microcirculation, agent acting on skin barrier, agent acting on energy metabolism of cells, agent increasing the substantivity, antimicrobial sequestering agent, analgesic agent, anesthetic agent, antacid agent, anti-acne agent, anti-aging agent, anti-wrinkle agent, anti-atrophy agent, anti-androgen agent, antibacterial agent, anti-scar agent, anti-seborrheic agent, anti-cracking agent, anti-cellulite agent, anti-stretch mark agent anti-dandruff agent, anti-foam agent, anti-fungal agent, anti-histamine agent, anti-inflammatory agent, anti-irritant agent, anti-microbial agent, anti-mite agents, antibiotic agent, anti-viral agent, antioxidant agent, anti-glycation agent, anti-neoplastic agent, anti-cancer agent, anti-skin cancer agent, anti-eczema agent, anti-psoriasis agent, antipollution agent, antiperspirant agent, anti-pruriginous agent, anti-pruritic agent, antiseptic agent, antistat agent, astringent, α-adrenergic receptor agonist, barrier agent, binding agent, bio-adhesive agents, botanical agent, botanical extract, biological additive, buffer agent, bulking agent, calcium sequestering agent, calming agent, carrier agent, chemical additive, cell lysate, cell culture medium, conditioned cell culture medium, chelating agent, circulatory stimulant agent, cleansing agent, collagen stimulating agent, co-emulsifier agent, colorant, conditioning agent, controlled release agent, cooling agent, co-solvent, coupling agent, curative agent, denaturant, deodorant agent, depilatory agent, desquamating agent, detangler agent, detergent, disinfectant, dispersant, dye stabilizer, dermatologically acceptable carrier, elastin stimulating agent, extracellular matrix stimulating agent, emollient, emulsifier, emulsion stabilizer, enzyme, enzymatic inhibitor, enzyme-inducing agent, coenzyme, cofactor, essential oil, exfoliant, fat soluble agent, fiber, film former, fixative, flavor, foam booster, foam stabilizer, foaming agent, fragrance, free radicals scavenger, fungicide, gellant, glosser, hair beaching agent, hair growth promoter, hair colorant, hair conditioning agent, hair-set polymer, hormone, hormone-like agent, humectant, hydrophobic agent, hydrotropic agents intermediate agent, hyaluronic acid stimulating agent, keratolytic agent, lathering agent, lipolytic agent, lubricant, make-up agent, moisture barrier agent, moisturizer, muco-adhesive agents, muscle relaxant, natural moisturizing factor, neutralizer, odor-masking agent, oil, oil absorbent agent, ointment base, opacifier, organosilicone, oxidant, oxygen carrier, pearlant agent, perfume, perfume solvent, perfume stabilizer, peroxide stabilizer, pharmaceutical drug, photo-sensitizer agent, pigment, pigmenting agent, pearlescent aid, plant extract, plant derivative, plant tissue extract, plant root extract, plant seed extract, plant oil, plasticizer, polish agent, polymer, polymer film former, powder, preservative agent, propellant, peptide agent, protein agent, reducing agent, re-fatting agent, regenerator, resin, rosacea inhibitory agent, scar prevention agent, scalp agent, scrub agent, sabostatic agent, sequestrant, sex hormone, sex stimulating agent, silicone agent, silicone replacement agent, skin barrier agent, skin barrier restoration agent, skin calming agent, skin clarifier, skin cleanser, skin conditioning agent, skin exfoliating agent, skin peeling agent, skin healing agent, skin lipid, skin lightening agent, skin bleaching agent, skin protectant agent, skin purifier agent, skin smoothing agent, skin calming agent, skin soothing agent, skin sensate, skin treatment agent, skin penetration enhancing agent, skin penetration retarding agent, mucosa penetration enhancing agent, solubilizer, solvent, suspending agent, sun protection factor booster, soothing agent, spreading agent, stabilizer, stimulant agent, slimming agent, sunless tanning agent, sunscreen, sunscreen UVA, sunscreen UVB, broad-band sunscreen, super-fatting agent, surfactant, amphoteric surfactant, anionic surfactant, cationic surfactant, non-ionic surfactant, silicone surfactant, suspending agent, sweetener, tanning accelerator, thickening agent, thixotrope, tightening agent, toner, tonic agent, topical delivery system, vasoconstrictor agent, vulvar soothing agent, vaginal soothing agent, vegetable oil, volatile agent, viscosity stabilizer, vitamin, vaccine, water proofing agent, water-soluble agent, water-proofing agent, wax, wetting agent, whitening agent, wound healing agent, and/or the like.

Preferably, the additional ingredients should be suitable for use in contact with human keratinous tissue (hair, nails, skin, lips, external vulva (mons pubis, labia majora, labia minora)) and/or non-keratinous tissue (vagina, introitus, inner vulva (vulvar vestibule, clitoris), mouth, anus, etc.), without undue systemic toxicity local intolerability, and chemical instability.

In most instances, the additional substances will include a cosmetic, dermatologically, and/or pharmaceutically acceptable carrier either alone or in combination with still other additional (e.g., inert and/or biologically active) ingredients. The total amounts of additional ingredients may range from about 90% to about 99.9999%, preferably from about 95% to about 99.999%, and more preferably from about 99% to about 99.999%, of the composition. In short, it is the balance of the composition. If carriers (either singularly, such as water, or complex co-solvents) are used, they may make up the entire balance of the compositions.

Non-limiting examples of additional ingredients for some of the functional classes listed above are provided herein. Additional examples of additional ingredients can be found in The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known (and commonly used) in the art.

In order to be suitable for use in accordance with the present invention, the additional ingredients and carrier/excipients must be further chemically compatible with Octanoyl Carnosine (or one or more derivatives thereof), with Palmitoyl-GHK (or one or more derivatives thereof), and/or with GEKG (SEQ ID NO:1) (or one or more derivatives thereof). Here, "chemically compatible" means that the additional ingredients do not lead to a significant chemical degradation (e.g., hydrolysis, oxidation). For example, a significant chemical degradation would include more than 10% degradation during the shelf-life period (e.g., as provided by the expiration date) of the product under the recommended storage conditions of the product.

Peptides

The composition of the present invention can contain additional peptide(s). Suitable peptides can include, but are not limited to, di-, tri-, tetra-, penta-, hexa-peptides, and other oligo- to poly-peptides, and derivatives thereof.

For example, when included in the present compositions, the additional peptides are preferably used in amounts ranging from about 0.000001% to about 10%, more preferably from about 0.000001% to about 1%, and even more preferably from about 0.00001% to about 0.1% by weight of the composition. The exact content (%) of peptides to be used in the compositions will depend on the particular peptide utilized since such agents vary widely in potency.

Suitable dipeptides for use herein include, but are not limited to, carnosine (beta-Ala-His), Tyr-Arg, Val-Trp (see WO 0164178), Asn-Phe, Asp-Phe. Suitable tripeptides for use herein include, but are not limited to, Arg-Lys-Arg, His-Gly-Gly, Gly-His-Lys, Gly-Gly-His, Gly-His-Gly, Lys-Phe-Lys. Suitable tetrapeptides for use herein include, but are not limited to, Peptide E, Arg-Ser-Arg-Lys (SEQ ID NO:10), Gly-Gln-Pro-Arg (SEQ ID NO:9). Suitable pentapeptides include, but are not limited to, Lys-Thr-Thr-Lys-Ser (SEQ ID NO:11). Suitable hexapeptides include, but are not limited to, Val-Gly-Val-Ala-Pro-Gly (SEQ ID NO:12) and such as those disclosed in FR 2854897 and US 2004/0120918.

Other suitable peptides for use herein include, but are not limited to, lipophilic derivatives of peptides, preferably octanoyl, decanoyl, lauroyl, myristoyl and palmitoyl derivatives, and metal complexes of the aforementioned (e.g., copper complex of the tripeptide His-Gly-Gly). Preferred dipeptide derivatives include N-Palmitoyl-beta-Ala-His, N-Acetyl-beta-Ala-His, N-Acetyl-Tyr-Arg-hexadecylester (WO 9807744, U.S. Pat. No. 6,372,717). Preferred tripeptide derivatives include the copper derivative of His-Gly-Gly, N-Elaidoyl-Lys-Phe-Lys and its analogs of conservative substitution, N-Acetyl-Arg-Lys-Arg-NH2, N-Biot-Gly-His-Lys (WO0058347) and derivatives thereof. Suitable tetrapeptide derivatives for use herein include, but are not limited to N-palmitoyl-Gly-Gln-Pro-Arg, suitable pentapeptide derivatives for use herein include, but are not limited to N-Palmitoyl-Lys-Thr-Thr-Lys-Ser (WO 0015188 and U.S. Pat. No. 6,620,419), N-Palmitoyl-Tyr-Gly-Gly-Phe-X with X Met or Leu (SEQ ID NO:13), or mixtures thereof. Suitable hexapeptide derivatives for use herein include, but are not limited to N-Palmitoyl-Val-Gly-Val-Ala-Pro-Gly and derivatives thereof.

The peptides can be obtained from any supplier of commercially available cosmetic and pharmaceutical peptides, peptide mixtures or derivatives thereof; including but not limited to Atrium, Unipex, Lucas Meyer Cosmetics, Biotechnologies, Sederma, Croda, Grant Industries, Pentapharm, DSM, Evonik, Lipotec, Symrise, BASF, ISP, Helix BioMedix, Oriflame, Seppic, Solabia, Procyte, EMD Chemicals, Corium Peptides, etc.; or can be directly obtained by custom synthesis. When using commercially available cosmetic and pharmaceutical peptides, the preferred composition generally contains the additional peptide(s) in the concentration range as recommended by the peptide supplier.

Additional examples of suitable peptides can be also found in the chapter by F. Gorohhui and H. I. Maibach in the Textbook of Aging (2010, Springer), in Clinics in Dermatology 2009, 27, 485-495, or numerous other scientific articles, communications, patent applications, granted patents on peptides for cosmetic or medical uses (incorporated herein by reference).

Ascorbates and Other Vitamins

The compositions of the present invention may contain one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate, tetrahexadecyl ascorbate, ascorbyl 3-aminopropyl phosphate), vitamin B, vitamin B derivatives, vitamin B1 to vitamin B12 and theirs derivatives, vitamin K, vitamin K derivatives, vitamin H, vitamin D, vitamin D3, vitamin D derivatives, vitamin E, vitamin E derivatives, and pro-vitamins thereof, such as panthenol and mixtures thereof. The vitamin compounds may be included as the substantially pure material, or as an extract obtained by suitable physical and/or chemical isolation from natural (e.g., plant) sources. In one example, when vitamin compounds are present in the compositions of the instant invention, the compositions contain from about 0.0001% to about 25%, more preferably from about 0.001% to about 10%, still more preferably from about 0.01% to about 5%, and still more preferably from about 0.1% to about 1%, by weight of the composition, of the vitamin compound. The exact content (%) of ascorbates and other vitamins to be used in the compositions will depend on the particular ascorbate and vitamin utilized since such agents vary widely in potency.

Sunscreen Actives

The compositions of the subject invention may optionally contain a sunscreen active. As used herein, "sunscreen active" includes both sunscreen agents and physical sunblocks. Suitable sunscreen actives may be organic or inorganic. A wide variety of conventional organic or inorganic sunscreen actives are suitable for use herein. In one example, the composition contains from about 0.1% to about 25%, more typically from about 0.5% to about 10% by weight of the composition, of the sunscreen active. Exact amounts will vary depending upon the sunscreen chosen and the desired Sun Protection Factor (SPF). The organic UV-screening agents which are more particularly preferred are chosen from the following compounds: ethylhexyl salicylate, butyl methoxydibenzoylmethane, ethylhexyl methoxycinnamate, octocrylene, phenylbenzimidazole sulphonic acid, terephthalylidene dicamphor sulphonic, benzophenone-3, benzophenone-4, benzophenone-5,4-methylbenzylidene camphor, benzimidazilate, anisotriazine, Ethylhexyl triazone, diethylhexyl butamido triazone, methylene bis-benzotriazolyl tetramethylbutylphenol, drometrizole trisiloxane, and mixtures thereof.

The inorganic sunscreen agents which may be used in the composition according to the invention are in particular nanopigments (mean size of the primary particles: generally between 5 nm and 100 nm, preferably between 10 nm and 50 nm; or their aggregates) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate, and silicones.

Anti-Wrinkle Actives and Anti-Atrophy Actives

The compositions of the present invention can contain a one or more anti-wrinkle actives or anti-atrophy actives. Exemplary anti-wrinkle/anti-atrophy actives suitable for use in the compositions of the present invention include amino acids, N-acetyl derivatives of amino acids (e.g., N-acetyl-cysteine), hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid (vitamin C), retinoids (e.g., retinoic acid, tretinoin, isotretinoin, adapalene, retinol, retinylaldehyde, retinylpalmitate, and other retinoid derivatives), kinetin (N6-furfuryladenine), zeatin and their derivatives (e.g., furfurylamino-tetrahydropyranyladenine), niacinamide (nicotinamide); growth factors and cytokines (e.g., TGF-beta 1, 2 and 3, EGF, FGF-2, PDGF, IL-1, IL-6, IL-8, IGF-1, IGF-2, etc.), cell lysates (e.g., dermal fibroblast cell lysate, stem cell lysate, processed skin cell proteins (PSP®), etc.), conditioned cell culture mediums (e.g., conditioned cell culture medium from dermal fibroblasts, conditioned cell culture medium from stem cells (e.g., epidermal stem cells, adipose stem cells, mesenchymal stem cells, etc.); cosmetic ingredients marketed under the trade names Nouricel-MD®, TNS®, or CCM™ Complex; etc.); cell extracts, stem cell extracts, components from stem cells; ingredients stimulating epidermal or other human adult stem cells; skin conditioning agents, stilbenes, cinnamates, ingredients activating sirtuin 1 (e.g., resveratrol); ingredients improving the functioning of the mitochondria; dimethylaminoethanol, synthetic anti-aging peptides, peptides from natural sources (e.g., soy peptides), and salts of sugar acids (e.g., Mn gluconate, Zn gluconate), lipoic acid; lysophosphatidic acid, vitamin B3 compounds, and other vitamin B compounds (e.g., thiamine (vitamin B1), pantothenic acid (vitamin B5), riboflavin (vitamin B2), and their derivatives and salts (e.g., HCl salts or calcium salts).

When anti-wrinkle/anti-atrophy compounds are present in the compositions of the instant invention, the compositions comprise from about 0.0001% to about 25%, more preferably from about 0.001% to about 10%, still more preferably from about 0.01% to about 5%, and still more preferably from about 0.1% to about 1%, by weight of the composition, of the anti-wrinkle/anti-atrophy compound. The exact content (%) of anti-wrinkle/anti-atrophy agents to be used in the compositions will depend on the particular anti-wrinkle/anti-atrophy agent utilized since such agents vary widely in potency.

Humectants, Moisturizers, and Conditioning Agents

The compositions of the present invention can contain a safe and effective amount of a conditioning agent selected from, for example, humectants, moisturizers, and skin conditioners. A variety of these materials can be employed and can be present at a level of from about 0.01% to about 80%, more preferably from about 0.1% to about 25%, and still more preferably from about 0.5% to about 10%, by weight of the composition. The exact content (%) of humectants, moisturizers, and conditioning agents to be used in the compositions will depend on the humectant, moisturizer, and conditioning agent utilized since such agents vary widely in potency.

Humectants are ingredients that help maintain moisture levels in skin. Humectants can be selected from the group consisting of polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Additional humectants include acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed proteins, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, butylene glycol, sodium pyrollidone carboxylic acid (PCA), sorbitol, sucrose, dextran sulfate (i.e., of any molecular weight), natural moisturizing factors, and/or urea.

Skin conditioners can include, but are not limited to, guanidine, urea, glycolic acid, glycolate salts (e.g., ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, hexanetriol, butanetriol, propylene glycol, butylene glycol, hexylene glycol and the like, polyethylene glycols, propoxylated glycerols, sugars (e.g., melibiose), starches, sugar and starch derivatives (e.g., alkoxylated glucose, fructose, glucosamine), C1-C30 monoesters and polyesters of sugars and related materials, hyaluronic acid, lactamide monoethanolamine, acetamide monoethanolamine, panthenol, dexpanthenol, allantoin, and mixtures thereof. Skin conditioners can also include fatty acids, fatty acid esters, lipids, ceramides, cholesterol, cholesterol esters, bee wax, petrolatum, and mineral oil.

Emollients

One or more emollients may also be included in the topical compositions described herein. An emollient generally refers to an ingredient that can help skin maintain a soft, smooth, and pliable appearance. Emollients typically remain on the skin surface, or in the stratum corneum, and act as a moisturizer, or lubricant and reduce flaking. Some examples of emollients include acetyl arginine, acetylated lanolin, algae extract, apricot kernel oil polyethylene glycol-6 esters, avocado oil polyethylene glycol-11 esters, bis-polyethylene glycol-4 dimethicone, butoxyethyl stearate, glycol esters, alkyl lactates, caprylyl glycol, cetyl esters, cetyl laurate, coconut oil polyethylene glycol-10 esters, alkyl tartrates, diethyl sebacate, dihydrocholesteryl butyrate, dimethiconol, dimyristyl tartrate, distearenth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, palm oil, coconut oil, myreth-3 palmitate, octyldecanol, octyldodecanol, odontella *aurita* oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, petrolatum, silicon oils including but not limited to caprylyl methicone, and/or tocopheryl glucoside.

Anti-Oxidants, and Radical Scavengers

The compositions of the present invention may include an anti-oxidant/radical scavenger. In one example, the composition contains from about 0.001% to about 25%, more preferably from about 0.01% to about 10%, and still more preferably from about 0.1% to about 5%, of an anti-oxidant/radical scavenger. The exact content (%) of anti-oxidant/radical scavengers to be used in the compositions will depend on the particular anti-oxidant/radical scavenger utilized since such agents vary widely in potency.

Anti-oxidants/radical scavengers may include but are not limited to ascorbic acid (vitamin C) and its salts, ascorbyl esters of fatty acids, and other ascorbic acid derivatives (e.g., magnesium ascorbyl phosphate, sodium ascorbyl phosphate, ascorbyl sorbate, ascorbyl palmitate, tetrahexyldecyl ascorbate, etc.), tocopherol (vitamin E), tocopherol sorbate, tocopherol acetate, other esters of tocopherol, beta-carotene, butylated hydroxy benzoic acids and their salts, ferulic acid, peroxides including hydrogen peroxide, perborate, thioglycolates, persulfate salts, 6-hydroxy-2,5,7,8-tetramethylchroman-2-carboxylic acid (commercially available under the trade name Trolox™), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lysine pidolate, arginine pilolate, amino acids, silymarin, lysine, 1-methionine, proline, superoxide dismutase, sorbic acids and its salts, lipoic acid, olive extracts, tea extracts, resveratrol, polyphenols such as proanthocyanidine from pine bark, carotenoids, curcumin compounds such as tetrahydrocurcumin, coenzyme Q10, OCTA (L-2-oxo-4-thiazolidine carboxylic acid), selenium, creatine, glutathione, N-acetyl cysteine, N-acetyl cysteine esters, dimethylmethoxy chromanol, lipoic acid, melanin; plant extracts containing polyphenols including but not limited to coffee berry extracts, green tea extracts, rosemary extracts, witch hazel extracts, and grape skin/seed extracts, may be used. Preferred antioxidants/radical scavengers can be selected from esters of ascorbic acid, tocopherol, ferulic acid, polyphenols, creatine, and their derivatives; as well as plant extracts containing polyphenols such as green tea extract.

Antimicrobial Peptide Sequestering Agents

Antimicrobial peptide sequestering compounds may include but are not limited to a sulfated or polysulfated monosaccharide, and salts and complexes thereof; a sulfated or polysulfated disaccharide, and salts and complexes thereof; a sulfated or polysulfated polysaccharide, and salts and complexes thereof; a dextran sulfate (e.g., sodium dextran sulfate), and salts and complexes thereof; chondroitin sulfate, and salts and complexes thereof; pentosan polysulfate, and salts and complexes thereof; sucrose sulfate (e.g., any sucrose sulfate such as sucrose octasulphate other than aluminum sucrose sulfate), and salts and complexes thereof; a fucoidan, and salts and complexes thereof; a sulfated galactan, and salts and complexes thereof; a carrageenans (e.g., *Chondrus Crispus*), and salts and complexes thereof; starch sulfate, and salts and complexes thereof; cellulose sulfate, and salts and complexes thereof; a sulfated glycosaminoglycan, and salts and complexes thereof; a heparin; a heparan sulfate; sulfated glucan; or any combinations thereof. The antimicrobial peptide sequestering compound may include a plant extract, an algae extract, an aloe vera (barbadensis) extract, a cactus extract, or a shark or fish cartilage extract. The antimicrobial peptide sequestering compound may also be a sulfated or polysulfated polymer (e.g., poly(vinyl sulfate), poly(anethole sulfonate)). Suitable polymeric sulfonic acid that can be used in the methods and compositions described herein are hydrophobically modified polymeric sulfonic acids such as Aristoflex® HMP or Aristoflex® AVC (Clamant). Alternatively, the antimicrobial peptide sequestering compound is a phosphate or polyphosphate (e.g., a monosaccharide phosphate, a disaccharide phosphate, a polysaccharide phosphate, a glycerophosphate salt, or a starch phosphate). Suitable examples of starch phosphates include, but are not limited to hydroxypropyl starch phosphates (i.e., Structure XL (National Starch, LCC)). The antimicrobial peptide sequestering compound may also be a phospholipid such as phosphatidylcholine or lecithin. Further, the antimicrobial peptide sequestering compound can be a carboxylate, a polyhydroxy acid, hyaluronic acid, alginate, and/or polylactic acid. Most preferably, the antimicrobial peptide sequestering compounds are between 100 to 10,000 g per mol. Sodium dextran sulfate of about 5000 to 10'000 g per mol is one of the most preferred antimicrobial peptide sequestering compound.

Rosacea Inhibitory Agents, and α-Adrenergic Receptor Agonists

Rosacea inhibitory agents, include but are not limited to, metronidazole, sulfacetamide, sodium sulfacetamide, sulfur, dapson, doxycycline, minocycline, clindamycin, clindamycin phosphate, erythromycin, tetracylcines, azelaic acid, calcium dobesilate, maleic acid, and any compatible combinations thereof); α-adrenergic receptor agonists (e.g., clonidine, amphetamine, doxtroamphetamine, apraclonidine, dipivefrin, α-methyldopa, oxymetazoline, oxymetazoline hydrochloride, methoxamine, metaraminol, medetomidine, dexmedetomidine, ethylnorepinephrine, guanfacine, guanabenz, phenylephrine, phenylephrine hydrochloride, ephedrine, epinine, epinephrine, ethylnorepinephrine, levarterenol, lofexidine, norepinephrine, norphenylephrine, norephedrine, phenylpropanolamine, pemoline, propylhexadrine, pseudoephedrine, methamphetamine, α-methylnorepinephrine, methylphenidate, mephentermine, midodrine, mivazerol, moxonidine, desglymidodrine, tetrahydrozoline, tetrahydrozoline hydrochloride, cirazoline, amidephrine, brimonidine, brimonidine tartrate, naphazoline, isoproterenol, xylazine, xylometazoline, and/or tizanidine); chemicals and botanical extracts with vasoconstrictor properties including, but not limited to, corticosteroids, ephedrine, pseudoephedrine, caffeine, and/or escin; ephedra, phedra sinica, hamamelis viginiana, hydrastis canadensis, lycopus virginicus, aspidosperma quebracho, cytisus scoparius, raphanus sativus linn (radish leave extracts), horse chestnut extracts, etc., as well as any compatible combinations thereof; and/or a nasal and/or sinus decongestant.

Skin Lightening Agents, and Skin Bleaching Agents

The compositions of the present invention may contain a skin lightening agent. Suitable skin lightening agents include, but are not limited to, ascorbic acid and derivatives thereof; kojic acid and derivatives thereof; resorcinol and derivatives thereof (including but not limited to 4-ethyl resorcinol, 4-butyl resorcinol, 4-hexyl resorcinol, 4-octyl resorcinol, 4-decyl resorcinol, 6-methyl resorcinol, 6-ethyl resorcinol, 6-butyl resorcinol, 6-hexyl resorcinol, 6-octyl resorcinol, 6-decyl resorcinol, 4-phenylethyl resorcinol), retinoic acid and derivatives thereof (e.g., retinol, retinyl palmitate), L-leucine and derivatives thereof (e.g., N-acyl derivatives of L-leucine, esters of L-leucine, etc.), glycine and derivatives thereof, disodium glycerophosphate and derivatives thereof, undecenoyl phenylalanine, arbutin and derivatives thereof (e.g., dehydroxyarbutin), niacinamide and derivatives thereof, hydroquinone; mequinol, glabridin, aleosin, curcumin, genistein, ethyl linoleate, tranexaminic acid, azelaic acid, resveratrol and derivatives thereof (e.g., oxyresveratrol), N-acetyl glucosamine, 4-isopropylcetchol, 4-ethoxybenzaldehyde, 2-ethoxybenzaldehyde, 4-propoxybenzaldehyde, alpha-hydroxyacids (e.g., glycolic acid, lactic acid, etc.), salicylic acid, polyphenols; and/or various plant extracts, such as those from licorice, grape seed, mulberry, soy, green tea, and/or bear berry; and/or any ingredient or combination thereof.

When used, the compositions preferably contain from about 0.01% to about 15%, more preferably from about 0.1% to about 10%, also preferably from about 0.5% to about 5%, by weight of the composition, of a skin lightening agent. The exact content (%) of skin lightening agents to be used in the compositions will depend on the particular skin lightening agent utilized since such agents vary widely in potency.

Skin Protectants

Suitable skin protectant agents for use in the compositions described herein include, for example, a compound that protects injured or exposed skin or mucous membrane surfaces from harmful or irritating external compounds. Representative examples include algae extract, allantoin, *camellia sinensis* leaf extract, cerebrosides, dimethicone, glucuronolactone, glycerin, kaolin, lanolin, malt extract, mineral oil, petrolatum, white petrolatum, potassium gluconate, colloidal oat meal, calamine, cocoa butter, starch, zinc oxide, zinc carbonate, zinc acetate, and/or talc.

Desquamation Actives, Keratolytic Agents, and Peeling Agents

A desquamating/keratolytic active may be added to the compositions of the present invention. In one example, the composition contains from about 0.01% to about 30%, preferably from about 0.1% to about 10%, more preferably from about 0.5% to about 5%, by weight of the composition, of a desquamating/keratolytic active. The exact content (%) of desquamating/keratolytic agents to be used in the compositions will depend on the particular desquamating/keratolytic agent utilized since such agents vary widely in potency.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids. Resorcinol and its low-molecular weight derivatives are other examples of useful keratolytic and/or desquamating agents.

Preferred keratolytic agents are selected from the group containing glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcinol, retinoic acid, adapalene, trichloroacetic acid, 5-fluoro uracil, azelaic acid. Keratolytic agents are also the salts, esters, possible cis- or trans-forms, racemic mixtures and/or the relative dextrorotatory or levorotatory forms of the above listed compounds. Such substances can be used singularly or in associations with each other.

Anti-Inflammatory Agents

An anti-inflammatory agent may be added to the compositions of the present invention. In one example, an anti-inflammatory agent is added at a level of from about 0.01% to about 10%, preferably from about 0.5% to about 5%, by weight of the composition. The exact content (%) of anti-inflammatory agents to be used in the compositions will depend on the particular anti-inflammatory agent utilized since such agents vary widely in potency.

Steroidal anti-inflammatory agents can include, but are not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, fluradrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. One of the preferred steroidal anti-inflammatory for use is hydrocortisone.

In addition, non-steroidal anti-inflammatory agents can be useful herein. The varieties of compounds encompassed by this group are well known to those skilled in the art. Specific non-steroidal anti-inflammatory agents that can be useful in the composition of the present invention include, but are not limited to, diclofenac, indomethacin, oxicams such as piroxicam, salicylates such as aspirin; acetic acid derivatives such as felbinac, fenamates such as etofenamate, flufenamic acid, mefenamic acid, meclofenamic acid, tolfenamic acid; propionic acid derivatives such as ibuprofen, naproxen, pyrazoles, and mixtures thereof. Mixtures of these non-steroidal anti-inflammatory agents may also be employed, as well as the dermatologically acceptable salts and esters of these agents. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), kola extract, chamomile, red clover extract, sea whip extract, licorice extract, and tea extract may be used.

Anti-inflammatory agents useful herein include allantoin and compounds of the Licorice, including glycyrrhetic acid, glycyrrhizic acid, and derivatives thereof (e.g., salts and suitable esters). Additional anti-inflammatory agents include diosgenol, saponines, sapogenines, lignanes, triterpenes saponosides and genines.

Additional examples of anti-inflammatory agents can include anti-inflammatory interleukins (e.g., IL-lra, IL-10); anti-inflammatory fatty acids (e.g., linoleic acid, linolenic acid) and their derivatives (e.g., esters), isoprenylcystein analogues (i.e., N-acetyl-S-farnesyl-L-cysteine), aromatic aldehydes with anti-inflammatory properties (e.g., 4-methoxy benzaldehyde, 4-ethoxy benzaldehyde, 4-butoxy benzaldehyde, 4-penthoxy benzaldehyde), as well as any compatible combinations thereof.

Anti-Acne Actives

The compositions of the present invention can contain one or more anti-acne actives. Examples of useful anti-acne actives include resorcinol, sulfur, erythromycin, salicylic acid, benzoyl peroxide, retinoic acid, tretinoin, alpha-hydroxy acids (e.g., glycolic acid, lactic acid), dehydroacetic acid and zinc. When anti-acne compounds are present in the compositions of the instant invention, the compositions contain from about 0.0001% to about 50%, more preferably from about 0.001% to about 20%, still more preferably from about 0.01% to about 10%, and still more preferably from 0.1% to about 5%, by weight of the composition, of the anti-acne compound. The exact content (%) of anti-acne actives to be used in the compositions will depend on the particular antimicrobial, anti-bacterial and anti-acne active utilized since such agents vary widely in potency.

Antimicrobial, Anti-Bacterial and Anti Fungal Actives

The compositions of the present invention can contain one or more anti-fungal or anti-microbial actives. A safe and effective amount of an antimicrobial or antifungal active can be added to the present compositions. For example, the composition contains from about 0.001% to about 10%, preferably from about 0.01% to about 5%, and more preferably from about 0.05% to about 2%, by weight of the composition, of an antimicrobial or antifungal active. The exact content (%) of antimicrobial, anti-bacterial and anti-fungal actives to be used in the compositions will depend on the particular antimicrobial, anti-bacterial and anti-fungal active utilized since such agents vary widely in potency.

Suitable anti-microbial actives include, but are not limited coal to tar, sulfur, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, iodopropynyl butylcarbamate, azelaic acid, isothiazalinones such as octyl isothiazolinone and azoles, parabens (e.g., methylparaben, ethylparaben, etc.), glycols (e.g., hexylenglycol, ethylhexylglycerin), and combinations thereof.

For example, suitable agents with anti-fungal properties are ketoconazole, naftifine hydrochloride, oxiconazole nitrate, sulconazole nitrate, urea, terbinafine hydrochloride, selenium sulfide. Suitable agents with anti-mite properties are crotamiton, ivermectin, and permethrin.

One or more anti-fungal or anti-microbial active is combined with an anti-dandruff active selected from polyvalent metal salts of pyrithione.

Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol; and pharmaceutically acceptable salts thereof; benzyl alcohol, camphor, menthol, resorcinol; and appropriate combinations thereof.

Plant Extracts and Vegetable Extracts

The compositions of the present invention may also contain a safe amount of a plant extract and vegetable extract. Examples of plant or vegetable extracts include extracts obtained from ivy (in particular English Ivy (*Hedera Helix*)), Chinese thorowax (*Bupleurum chinensis*), barley, *Bupleurum Falcatum*, arnica (*Arnica Montana* L), rosemary (*Rosmarinus officinalis* N), marigold (*Calendula officinalis*), sage (*Salvia officinalis* L), soy, ginseng (*Panax ginseng*), ginko biloba, St.-John's-Wort (*Hyperycum Perforatum*), butcher's-broom (*Ruscus aculeatus* L), European meadowsweet (*Filipendula ulmaria* L), big-flowered Jarva tea (*Orthosiphon Stamincus* Benth), algae (*Fucus Vesiculosus*), birch (*Betula alba*), green tea, white tea, fermented tea, cola nuts (Cola Nipida), horse-chestnut, bamboo, spadeleaf (*Centella asiatica*), heather, fucus, willow, witch hazel, wild yam, mouse-ear, escine, cangzhu, *chrysanthellum indicum*, plants of the *Armeniacea* genus, *Atractylodis Platicodon, Sinnomenum, Pharbitidis, Flemingia, Coleus* such as *C. Forskohlii, C. blumei, C. esquirolii, C. scutellaroides, C. xanthantus and C, Barbatus*, root of *Coleus barbatus, Ballote, Guioa, Davallia, Terminalia, Barringtonia, Trema, antirobia, cecropia, argania, dioscoreae* such as *Dioscorea opposita* or Mexican, *Ammi visnaga, Centella asiatica* and *Siegesbeckia*, in particular *Siegesbeckia orientalis*, the family of Ericaceae in particular bilberry extracts (*Vaccinium angustifollium*) or *Arctostaphylos uva ursi*, aloe vera, plant sterols (e.g., phytosterol), *Manjistha* (extracted from plants in the genus *Rubia*, particularly *Rubia Cordifolia*), and *Guggal* (extracted from plants in the genus *Commiphora*, particularly *Commiphora Mukul*), kola extract, chamomile, red clover extract, *Piper methysticum, Bacopa monieri* extract, sea whip, *Glycyrrhiza glabra*, mulberry, melaleuca (tea tree), mushroom extracts, *Larrea divaricata, Rabdosia rubescens, euglena gracilis, Fibraurea recisa Hirudinea*, Chaparral Sorghum, sun flower extract, *Enantia chlorantha*, Mitracarpe of *Spermacocea* genus, *Buchu barosma, Lawsonia inermis* L., *Adiantium Capillus-Veneris* L., *Chelidonium majus, Luffa* cylindrical, Japanese Mandarin (*Citrus reticulata Blanco* var. *unshiu*), broccoli extract, *Camelia sinensis, Imperata* cylindrical, *Glaucium Flavum, Cupressus Sempervirens, Polygonatum multiflorum*, loveyly hemsleya, *Sambucus Nigra, Phaseolus lunatus, Centaurium, Macrocystis Pyrifera, Turnera Diffusa, Anemarrhena asphodeloides, Portulaca pilosa, Humulus lupulus*, Coffee Arabica, coffee berry, black berry, *Ilex Paraguariensis*; and so on.

Oils and Lipids

The oil phase can contain any cosmetic or dermatological oil or a mixture thereof. Examples of such oils include but are not limited to aliphatic hydrocarbons such as liquid paraffin, squalene, squalane, vaseline and ceresin; silicon oils such as dimethicone and cyclomethicones; vegetable oils such as avocado oil, apricot oil, almond oil, borage oil, borage seed oil, *camellia* oil, canola oil, castor oil, coconut oil, cocoa butter, corn oil, cottonseed oil, olive oil, evening primrose oil, flax seed oil, palm oil, palm kernel oil, peanut oil, rapeseed oil, safflower oil, sesame oil, sweet almond oil, rose hip oil, *calendula* oil, chamomile oil, eucalyptus oil, juniper oil, safflower oil, sandalwood oil, tea tree oil, sunflower oil, soybean oil, wheat germ oil; animal oils such as shark liver oil, cod liver oil, whale oil, beef tallow and butterfat; waxes such as beeswax, carnauba palm wax, spermaceti and lanolin; fatty acids such as lauric acid, myristic acid, palmitic, acid, stearic acid, oleic acid, behenic acid; omega-3 fatty acids such as alpha-linolenic acid, eicosapentaenoic acid, and docosahexaenoic acid; omega-6 fatty acids such as linoleic acid and gamma-linolenic acid; aliphatic alcohols such as lauryl, stearyl, cetyl, and oleyl alcohol; and aliphatic esters such as isopropyl, isocetyl, or octadecyl myristate, butyl stearate, hexyl laureate, diisopropyl ester of adipic acid, or diisopropyl sebacate; and/or mixtures thereof. Generally, the oils are refined and/or hydrogenated. Lipids include monoglycerides, diglycerides, triglycerides, phospholipids, and ceramides.

Suspending Agents

The compositions of the present invention may further contain a suspending agent, preferably at concentrations effective for suspending water-insoluble material in dispersed form in the compositions or for modifying the viscosity of the composition. Such concentrations can preferably range from about 0.1% to about 10%, more preferably from about 0.25% to about 5.0%. Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Other optional suspending agents include crystalline suspending agents which can be categorized as acyl derivatives, long chain amine oxides, long chain acyl derivatives and mixtures thereof. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin). Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

Emulsifying Agents

Emulsifying agents include a wide variety of nonionic, cationic, anionic, zwitterionic, and amphoteric surfactants such as are known in the art and discussed below. The hydrophilic surfactants (cationic, anionic, zwitterionic, amphoteric) useful herein can contain a single surfactant, or any combination of suitable surfactants. The exact surfactant (or surfactants) chosen will depend upon the pH of the composition and the other components present.

Useful nonionic surfactants include the condensation products of alkylene oxides with fatty acids (i.e., alkylene oxide esters of fatty acids), the condensation products of alkylene oxides with 2 moles of fatty acids (i.e., alkylene oxide diesters of fatty acids), the condensation products of alkylene oxides with fatty alcohols (i.e., alkylene oxide ethers of fatty alcohols), the condensation products of alkylene oxides with both fatty acids and fatty alcohols [i.e., wherein the polyalkylene oxide portion is esterified on one end with a fatty acid and etherified (i.e., connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof. Still other useful nonionic surfactants include polyhydroxy fatty acid amide surfactants. An especially preferred surfactant corresponding to the above structure is coconut alkyl N-methyl glucoside amide. Preferred among the nonionic surfactants are those selected from the group consisting of steareth-21, ceteareth-20, ceteareth-12, sucrose cocotte, steareth-100, PEG-100 stearate, and mixtures thereof. Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof. Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the trade name Arlatone 2121.

Also useful herein are cationic surfactants, especially dialkyl quaternary ammonium compounds. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride. Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow)dimethyl ammonium chloride, di(hydrogenated tallow)dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride. More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof. A preferred combination of cationic surfactant and structuring agent is behenamidopropyl PG dimonium chloride and/or behenyl alcohol, wherein the ratio is preferably optimized to maintain or to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethianonic acid and neutralized, i.e., the alkoyl isethionates typically have the formula RCOOCH2CH2SO3M wherein R is alkyl or alkenyl of from about 10 to about 30 carbon atoms, and M is a water-soluble cation such as ammonium, sodium, potassium and triethanolamine. For example, the fatty acids are derived from coconut or palm kernel oil. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. The alkyl and alkyl ether sulfates typically have the respective formulae ROSO3M and RO(C2H4O)xSO3M, wherein R is alkyl or alkenyl of from about 10 to about 30 carbon atoms, x is from about 1 to about 10, and M is a water-soluble cation such as ammonium, alkanolamines such as triethanolamine, monovalent metals, such as sodium and potassium, and polyvalent metal cations such as magnesium and calcium. Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized. Another suitable class of anionic surfactants are the water-soluble salts of the organic, sulfuric acid reaction products of the general formula R1-503-M, wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and beta-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-0,2-dicarboxyethyfi-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxyalkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. Another class of anionic surfactants suitable for use in the compositions is the beta-alkyloxy alkane sulfonate class. Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH(CH2)mCO2M wherein m is from 1 to 4, R is a C8-C22 alkyl or alkenyl, and M is H, alkali metal, alkaline earth metal ammonium, or alkanolammonium. Preferred amphoteric surfactants for use in the present invention include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate; N-higher alkyl aspartic acids; and the products sold under the trade name "Miranol". Other examples of useful amphoterics include phosphates, such as coamidopropyl PG-dimonium chloride phosphate (commercially available as Monaquat PTC, from Mona Corp.). Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alphacarboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel). Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Thickening Agents

Thickening agents suitable for inclusion in a composition described herein include those agents commonly used as an excipient or a carrier for topical application to increase the viscosity of the formulation. Thickening agents may also be used to improve the stability of the formulation and the product.

More specifically, such examples include but are not limited to, acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethyl-cellulose, hydroxypropylcellulose, hydroxypropyl starch, magnesium alginate, methylcellulose, microcrystalline cellulose, pectin, various polyethylene glycol's, polyacrylic acid, poly-methacrylic acid, polyvinyl alcohol, various polypropylene glycols, sodium acrylates copolymer, sodium carrageenan, xanthan gum, and/or yeast beta-glucan.

More generally, carboxylic acid polymers useful thickening agents. Carboxylic acid polymers are cross-linked compounds containing one or more monomers derived from acrylic acid, substituted acrylic acids, and salts and esters of these acrylic acids and the substituted acrylic acids, wherein the cross-linking agent contains two or more carbon-carbon double bonds and is derived from a polyhydric alcohol. Examples of commercially available carboxylic acid polymers useful herein include the carbomers, which are homopolymers of acrylic acid cross-linked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of C10-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-30 alkyl acrylate crosspolymers and are commercially available as Carbopol® 1342, Carbopol® 1382, Pemulen TR-1, and Pemulen TR-2, from B.F. Goodrich. Examples of preferred carboxylic acid polymer thickeners useful herein include those selected from carbomers, acrylates/C10-30 alkyl acrylate crosspolymers, and mixtures thereof.

Moreover, a wide variety of polysaccharides are useful herein as thickening agents. Non-limiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10-30 straight chain or branched chain alkyl group through an ether linkage Typically these polymers are ethers of C10-30 straight or branched chain alcohols with hydroxyalkylcelluloses. Examples of alkyl groups useful herein include those selected from stearyl, isostearyl, lauryl, myristyl, cetyl, isocetyl, cocoyl (e.g., alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the trade name Natrosol® CS Plus from Aqualon Corporation (Wilmington, Del.). Additional examples can be found in The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art. Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, dextran sulfate, sodium carrageenan, tragacanth gum, xanthan gum, and/or mixtures thereof. In addition, the compositions of the present invention can also optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the trade name Sepigel 305 from Seppic Corporation (Fairfield, N.J.). Other polyacrylamide polymers useful herein include multi-block copolymers of acrylamides and substituted acrylamides with acrylic acids and substituted acrylic acids.

Preferred compositions of the present invention include a thickening agent selected from carboxylic acid polymers, cross-linked polyacrylate polymers, polyacrylamide polymers, and mixtures thereof, more preferably selected from carboxylic acid polymers, polyacrylamide polymers, and mixtures thereof.

Penetration Enhancers

Penetration enhancers are the substances that facilitate the absorption of penetrant through the skin or mucosal membranes by temporarily diminishing the impermeability of the skin or, respectively, the mucosa. Ideally, these materials should be pharmacologically inert, nontoxic, nonirritating, non-allergenic, compatible with Octanoyl Carnosine, odorless, tasteless, colorless, and inexpensive and have good solvent properties. The enhancer should not lead to the significant loss of body fluids, electrolytes, and other endogenous materials, and skin or mucosa should regain its barrier properties on its removal within an acceptable period of time. No single penetration enhancer can possess all the required properties. However, many enhancers exhibit many of these attributes, and they have been described (for example as reviewed in Drug Development and Industrial Pharmacy 2000, 26, 1131-1140) or are being currently researched.

Anti-Histamines

Anti-histamines, also called histamine antagonists, are substances that inhibit the action of histamine by blocking it from attaching to histamine receptors; or by inhibiting the enzymatic activity of histidine decarboxylase, catalyzing the transformation of histidine into histamine; or similar Examples of anti-histamines are acrivastine, azelastine, brompheniramine, buclizine, bromodiphenhydramine, carbinoxamine, cetirizine, chlorpromazine, cyclizine, chlorpheniramine, chlorodiphenhydramine, cimetidine, clemastine, cyproheptadine, desloratadine, dexbrom-pheniramine, deschlorpheniramine, dexchlorpheniramine, dimenhydrinate, dimetindene, diphenhydramine, doxylamine, ebastine, embramine, famotidine, fexofenadine, lafutidine, levocetirizine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tripelennamine, and triprolidine.

The choice of additional substances to be included in the composition is made depending on the constraints relating to Octanoyl Carnosine (or one or more derivatives thereof) (e.g., stability, solubilization, etc.), if enhanced and/or additional benefits and properties (e.g., anti-acne, anti-microbial, anti-wrinkle, skin lightening, anti-redness, antioxidant, skin protectant, sunscreen, hair growth, anti-inflammatory, emolliant, moisturization, enhanced skin penetration, etc.) of the composition are desired, and, where applicable, the use subsequently envisaged for the composition.

As mentioned, the compositions of the invention may include one or more additional substances, various, conventional or not, which will provide some benefit to the object of the composition. More specifically, the combination of Octanoyl Carnosine (or one or more derivatives thereof) with selected additional substances may lead to an enhanced efficacy as compared to the use of Octanoyl Carnosine (or one or more derivatives thereof) alone. The enhanced efficacy can be additive (the sum of efficacies of the individual agents alone), or it can be synergistic (larger than the sum of efficacies of the individual agents alone). Of course, a decision to include an additional ingredient or substance and the choice of a specific ingredient or substance depends on the specific use of the composition and the product formulation.

For example, the use of one or more suitable anti-wrinkling substance (e.g., retinoic acid, retinol, transforming growth factor beta-1, selected peptides, etc.) will increase the clinical efficacy (e.g., reduced skin wrinkles) of the composition containing Octanoyl Carnosine (or one or more derivatives thereof) after topical administration; the use of one or more suitable emollient substance (e.g., octyldodecanol, etc.) will increase the clinical efficacy (e.g., improved skin feel or sensations) of the composition containing Octanoyl Carnosine (or one or more derivatives thereof) after topical administration; the use of one or more suitable humectant substance (e.g., glycerin, hyaluronic acid, etc.) will increase the clinical efficacy (e.g., increased skin moisturization) of the composition containing Octanoyl Carnosine (or one or more derivatives thereof) after topical administration; the use of one or more suitable skin penetration enhancer substance (e.g., propylene glycol, butylene glycol, ethanol, oleic acid, lauric acid, palmitic acid, isopropyl palmitate, DMSO, sodium lauryl sulfate, Azone®, etc.) for Octanoyl Carnosine (or one or more derivatives thereof) will increase the clinical efficacy (e.g., reduced skin wrinkles) of the composition containing Octanoyl Carnosine (or one or more derivatives thereof) after topical administration; the use of one or more suitable anti-inflammatory substance (e.g., bisabolol, glycyrrhetinic acid, linoleic acid, borage seed oil, wheat germ oil, etc.) will increase the clinical efficacy (e.g., reduced irritation or redness of skin or mucosa) of the composition containing Octanoyl Carnosine (or one or more derivatives thereof) after topical administration; the use of one or more suitable topical anesthetic substance (e.g., lidocaine, pramoxine hydrochloride, etc.) will increase the clinical efficacy (e.g., reduced local pain) of the composition containing Octanoyl Carnosine (or one or more derivatives thereof) after topical administration; and the use of one or more suitable topical anti-histamine substance (e.g., diphenhydramine, etc.) will increase the clinical efficacy (e.g., reduced local itch) of the composition containing Octanoyl Carnosine (or one or more derivatives thereof) after topical administration.

Carriers and Excipients

The compositions of the present invention can also contain one or more carriers and/or excipients acceptable for a mode of administration (i.e., for topical application and/or for subcutaneous administration). Those skilled in the art will be able to routinely select an appropriate carrier and/or excipient for the mode of administration. Depending in the use and the way of administration, the compositions of the present invention can also contain a carrier and/or excipient acceptable for injection, implantation, or subcutaneous placement.

The carrier and/or excipient can be in a wide variety of forms. Non-limiting examples of suitable carriers and/or excipients include simple solutions (water or oil based), emulsions, dispersions, multi-phase systems, semi-solid forms, solid forms (powder, sticks, patches), skin masks, tissues, foams, and aerosols. For example, emulsion carriers and/or excipients can include, but are not limited to, oil-inwater, silicone-in-water, water-in-oil, water-in-silicone, water-in-oil-in-water, oil-in-water-in-oil, and oil-in-water-in-silicone emulsions.

Depending upon the desired product form, preferred carriers and/or excipients can contain an emulsion such as oil-in-water emulsions (e.g., silicone-in-water) and water-in-oil emulsions, (e.g., water-in-silicone emulsions). In one example, oil-in-water emulsions are especially preferred. Emulsions according to the present invention can contain an aqueous phase and a lipid or oil. Lipids and oils may be derived from animals, plants, or petroleum and may be natural or synthetic (e.g., man-made).

Preferred emulsions can also contain a humectant, such as glycerin. Emulsions can further contain from about 0.1% to about 25%, more preferably from about 0.2% to about 10%, of an emulsifying agent (emulsifier), based on the weight of the composition. Emulsifier agents may be nonionic, anionic, or cationic. Suitable emulsifiers are disclosed for example in McCutcheon's Detergents and Emulsifiers, North American Edition, pages 317-324 (1986).

Suitable emulsions may have a wide range of viscosities, depending on the desired product form. The compositions of the present invention can be in the form of pourable liquids, semi-solids, to highly viscous systems (e.g., solids) under ambient conditions.

Any of the compositions can contain an aqueous carrier and/or excipient, which is typically present at a level of from about 20% to about 99%, preferably from about 60% to about 90%. The aqueous carrier and/or excipient may contain water, or a miscible mixture of water and organic solvent (e.g., alcohols, including but not limited to ethanol, glycerin, propylene glycol, butylene glycol, other glycols, etc.), but preferably contain water with significant lower or no concentrations of organic solvent, except as otherwise incidentally incorporated into the composition as minor ingredients of other essential or optional components.

The compositions of the subject invention, including but not limited to solutions, lotions, serums and creams, may contain an acceptable emollient. Such compositions preferably contain from about 1% to about 80% of the emollient. As used herein, "emollient" refers to a material useful for the prevention or relief of dryness, as well as for the protection of the skin. A wide variety of suitable emollients is known and may be used herein. In addition to the examples of emollients provided above, Sagarin, Cosmetics, Science and Technology, 2nd Edition, Vol. 1, pp. 32-43 (1972) contains numerous other examples of materials suitable as an emollient. A preferred emollient is glycerin. Glycerin is preferably used in an amount of from or about 0.001% to or about 80%, more preferably from or about 0.01% to or about 25%, still more preferably from or about 0.1% to or about 10%, and even more preferably from or about 2% to or about 5%.

Lotions, serums and creams according to the present invention generally contain a carrier and/or excipient and one or more emollients. Lotions and creams typically contain from about 1% to about 50%, preferably from about 1% to about 20%, of emollient; from about 50% to about 90%, preferably from about 60% to about 80%, water; and, optionally, additional substances in amounts sufficient to provide additional benefits. Creams are generally thicker than lotions and serums due to higher levels of emollients, higher levels of thickeners, and/or differences in the emulsifying system.

Ointments of the present invention may contain a simple base of animal or vegetable oils or semi-solid hydrocarbons such as petrolatum; absorption ointment bases which absorb water to form emulsions; or water soluble carriers, e.g., a water soluble solution carrier. Ointments may further contain a thickening agent, such as described above and in Sagarin, Cosmetics, Science and Technology, 2nd Edition, Vol. 1, pp. 72-73 (1972), and/or an emollient. For example, an ointment may contain from about 2% to about 10% of an emollient; from about 0.1% to about 2% of a thickening agent as well as one or more additional substances(s) in amounts sufficient to provide additional benefits.

Compositions of this invention useful for cleansing ("cleansers") can be formulated with a suitable carrier, e.g., as described above, and preferably contain from about 1% to about 30%, more preferably from about 5% to about 10%, of an acceptable surfactant. The surfactant is suitably selected from anionic, nonionic, zwitterionic, amphoteric and ampholytic surfactants, as well as mixtures of these surfactants. Such surfactants are well known to those skilled in the detergency art. Examples of a broad variety of surfactants useful herein are described above and in McCutcheon's Detergents and Emulsifiers, North American Edition (1986), published by Allured Publishing Corporation. The cleansing compositions can optionally contain, at their art-established levels, other materials which are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like.

The compositions of the present invention can also contain a liquid that is acceptable for injection to and/or under the skin if the composition is to be injected. Any suitable acceptable liquid as known in the art or otherwise can be used.

Composition Preparation

The compositions of the present invention are generally prepared by conventional methods such as are known in the art of making compositions suitable for topical application. Such methods can typically be conducted in one or more steps, with or without heating, cooling, and the like.

In addition, the compositions of the present invention can also be prepared by conventional methods such as are known in the art of making compositions suitable for injections.

As used herein, a "formulation" is a mixture prepared according to a specific procedure.

The physical form of the compositions according to the invention is not important. They may be in any galenic form such aerosols, creams, lotions, milk or cream ointments, gels, emulsions, dispersions, solutions, suspensions, cleansers, foundations, anhydrous preparations (sticks, in particular lip balm, body and bath oils), shower and bath gels, shampoos and scalp treatment lotions, cream or lotion for care of skin or hair, gel or solution for care of skin or hair, cream or lotion for care of the genitals (e.g., vulva, vagina, penis, scrotum), gel or solution for care of genitals, make-up removing lotions or creams, sunscreen lotions, milks, artificial suntan lotions; pre-shave, shave or after shave creams, foams, gels or lotions; make-up, lipsticks, mascaras or nail varnishes; skin essences, serums; adhesive or absorbent materials, skin masks; tissues; hydrating patches, transdermal patches, iontophoretic patches, microneedle patches; powders; emollient lotion, sprays, oils for the body and the bath, foundation tint bases, pomade, colloid, compact or solid suspension, pencil, sprayable or brossable formulation, blush, rouge, eyeliner, lip liner, lip gloss, facial or body powder, mousse or styling gels, nail conditioner, lip balms, skin conditioners, anorectal creams, hygiene cream, moisturizers, hair sprays, hair conditioners, soaps, body exfoliants, astringents, depilatories and permanent waving solutions, anti-dandruff formulations, anti-hair loss formulations, anti-sweat and anti-perspirant formulations, nose sprays; and so on.

These compositions can also be presented in the form of lipsticks intended to apply color or to protect the lips from cracking, or of make-up products for the eyes or tints and tint bases for the face. Compositions in accordance with the invention include cosmetics, personal care products, feminine products, male products, hygiene products, and dermatological or pharmaceutical preparations.

The compositions of the present invention may also be applied on animal skin when wounds or defects or disorders of animal skin affecting the extracellular matrix are present.

The compositions according to the present invention may be prepared in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes, cubosomes; macro-, micro-, or nanoparticles; or macro-, micro or nanosponges; or macro-, micro-, and nanocapsules; or macro-, micro- or nanospheres; micro- or nanoemulsions; or adsorbed onto tip of needles; or adsorbed onto microneedles or onto microneedle arrays; or adsorbed to organic polymer powders, talcs, bentonites, or other inorganic or organic supports.

Furthermore, the compositions according to the present invention may be used in any form whatsoever, in a form bound to or incorporated in or absorbed in or adsorbed on macro-, micro-, and nanoparticles; or macro-, micro or nanosponges; or macro-, micro-, and nanocapsules; or macro-, micro- or nanospheres; or adsorbed (e.g., by coating) onto microneedle patches or arrays (such as described by Amen M. et al., Pharm Res 2010, 27: 303-313); for the treatment of textiles, natural or synthetic fibers, wools, and any materials that may be used for clothing or underwear for day or night intended to come into contact with the skin, handkerchiefs or cloths, to exert their effect via this skin/textile contact and to permit continuous topical deliver.

The compositions according to the present invention may also be prepared or used in a form of a device (e.g., medical device, combination between drug and medical device). Preferred devices include, but are not limited to, devices for overcoming biological barriers such as ultrasound devices (i.e., sonophoresis, sonoporation, acoustic ablation), electric devices (iontophoresis, electroporation), high pressure devices (i.e., liquid injection, powder injection), microneedles (i.e., solid, hollow, degradable, coated), thermal and optical devices (i.e., light, infrared, laser, radiofrequency), other physical devices reducing the skin barrier (i.e., plasma devices, micro-dermabrasion, dermabrasion, suction devices, macro-needle devices, etc.), devices reducing the skin barrier by chemical means (i.e., chemical exfoliating devices, skin corrosion (e.g., using NaOH) devices), and/or any combination or combination device thereof. Some example of methods and devices for overcoming biological barriers have been described in Advanced Drug Delivery Reviews 2013, 65, 100-103 (incorporated herein as reference).

In addition, the compositions according to the present invention may be used in any form intended to be placed into the skin or mucosal tissue, or under the skin or mucosal tissue (e.g., by injection, implantation, or subcutaneous placement).

Method of Treatment

The present invention concerns compositions for their application as a cosmetic, personal care, or a medicinal product.

The composition according to the invention can be applied topically onto any areas of the face, neck, neckline, décolleté, scalp, hand, palm, arm, leg, foot, sole, chest, breast, back, abdomen, buttock, vulva, or penis and scrotum, anus, and/or any other skin areas of the human body.

Further, the composition according to the invention can be also applied locally or topically onto any areas of the eye, mouth, nose; breast nipples, vulva, vagina and introitus; or penis and scrotum; rectum, and/or any other mucosal areas of the human body.

Furthermore, the composition according to the invention can also be applied locally or topically to other surfaces of the human body, including hair and nail, or any wound, scar, or skin and mucosal surface areas affected by atrophy, or other conditions, disorders and diseases associated with changes in extracellular matrix components.

In addition, the compositions according to the present invention may also be applied by injection, implantation, or subcutaneous placement.

For example, the compositions described herein can be applied using a syringe, a micro-cannula, a patch, an iontophoretic patch, microneedles, and/or a microneedle array or patch. In addition, the composition can be also applied in conjunction (i.e., before, after, or simultaneously) with the use of other skin devices changing the penetration characteristics of skin such as, for example, laser, light, infrared, radiofrequency, ultrasound, electroporation, sonophoresis, thermal, plasma, and/or high pressure devices, and/or any combination(s) (including combination devices) thereof. Any other commonly used means of administration can also be utilized.

In addition, the compositions according to the present invention may also be applied in animals.

In one example, the present invention concerns cosmetic treatment methods to improve the general state of the skin involving topical application of an effective amount of the composition as defined above to the skin. More specifically, these methods can be used to prevent and/or treat the signs of intrinsic and extrinsic skin aging; to prevent and/or treat skin slackening and/or improve tone and/or firmness and/or elasticity of the skin; to prevent and/or treat skin atrophy and/or improve the density of the dermis and epidermis; to give or return volume to the dermis and epidermis; to prevent and/or treat skin dehydration; to prevent and/or treat skin roughness; to prevent and/or treat cellulite, to prevent and/or treat stretch marks, to reduce expansion and/or prevent the development of adipose tissue within the hypodermis; to lighten and/or whiten the skin; to prevent and/or treat glycation of molecules in the skin; and/or to prevent and/or treat degradation of the skin due to the effects of oxidation.

The present invention also provides methods to improve the general state of the atrophic tissue involving topical application of an effective amount of the composition as defined above to the tissue. More specifically, such methods can be used to restore damaged skin; to restore skin after cosmetic and dermatological procedures; to prevent and/or treat atrophy of the female genitals, to prevent and/or treat vulvovaginal atrophy; to prevent and/or treat skin conditions and disorders related to menopause; to prevent and/or treat skin conditions and disorders associated with reduced estrogen levels in females; to prevent and/or treat vulvodynia; to prevent and/or treat vulvar lichen sclerosus; to prevent and/or treat vulvar dermatoses; to prevent and/or treat the signs of intrinsic and extrinsic aging of the female genitals; and/or to prevent and/or treat the signs of intrinsic and extrinsic aging of male genitals.

Some benefits (e.g., moisturization, soothing, calming, tightening, smooth feel, etc.) can be noticed within a few hours to a few days after topically applying the compositions according to the present invention on the affected human skin or human tissue (for example vulva and/or vagina). However, it takes generally at least 30 days to notice benefits (e.g., anti-aging, wrinkle reducing, skin lightening, anti-redness, improving atrophy, wound healing, etc.). Thereby, the composition should be applied to the affected human skin or human tissue at least once to twice a day.

Determination of an effective dose (e.g., therapeutically, cosmetically, pharmaceutically, and/or medicinally effective dose) of any of the compositions of the instant invention is within the routine level of skill in the art.

Kits and Dosage Forms

According to the invention, products or devices with several compartments or kits (having one or more containers) may be proposed to apply the compositions of the invention. By way of non-limiting example, a first compartment or container having a composition including the Octanoyl Carnosine, the selected tri-peptides, and/or tetra-peptides (or one or more derivatives thereof), and one or more additional substances (e.g., one or more biologically active ingredients and/or one or more inactive ingredients such as an excipient and/or a carrier) in a second compartment or container, the compositions contained in the said first and second compartments in this case being considered to be a combination composition for simultaneous, separate or step-wise use in time, particularly in any one of the treatments defined above. Alternatively, kits according to the invention may include the components of the compositions in separate compartments or containers or certain components can be in the same compartments or containers while others are in separate compartments or containers. Such kits will also preferably include instructions for use.

Any of the compositions described herein may be supplied in dosage unit form for ease of administration and uniformity of dosage. Dosage unit form as used herein refers to physically discrete units suited as unitary dosages for the mammalian subjects to be treated; each unit containing a predetermined quantity of Octanoyl Carnosine (and one or more additional active ingredients) calculated to produce the desired cosmetic, personal care or therapeutic effect in association with the required cosmetic and/or pharmaceutical carrier(s). The specification for the dosage unit forms of the invention are dictated by and directly dependent on (a) the unique characteristics of the compositions and the particular maintenance, therapeutic or prophylactic effect to be achieved, and (b) the limitations inherent in the art of compounding Octanoyl Carnosine (and one or more additional active ingredients) for the treatment of individuals.

The unit dosage form is any of a variety of forms, including, for example, but not limited to, a solution, any semi-solid form, a capsule, a bag, a tablet, a single pump on an aerosol or a vial. The quantity of active ingredient(s) in a unit dose of composition is an effective amount and is varied according to the particular treatment involved.

One skilled in the art will appreciate that it is sometimes necessary to make routine variations to the dosage depending on the age and condition of the patient. The dosage will also depend on the route of administration.

EXAMPLES

Examples of methods of chemical synthesis of Octanoyl Carnosine, Palmitoyl-GHK, and GEKG (SEQ ID NO:1), as well as suitable compositions and their preparation according to the present invention will be described hereafter. These compositions and their preparation are representative, but do not restrict, the scope of the invention.

The Examples set forth herein are meant to exemplify the various aspects of carrying out the invention and are not intended to limit the invention in any way. Unless otherwise specified, it is to be understood that the concentrations of the ingredients in the compositions of the invention are in weight percentages (w %), based on the total weight of the composition. All measurements are performed at 25° Celsius unless stated otherwise.

The following examples describe and demonstrate various aspects within the scope of the present invention. The examples are only given for illustrative purposes and should not be considered to be restrictive to this invention. Additionally for illustrative purposes several compositions and their use for topical administration will be described.

Example 1

Example of Synthesis of Peptide Octanoyl Carnosine

The di-peptide Octanoyl Carnosine can be prepared according to standard procedures in peptide chemistry using solid-phase synthesis or liquid-phase synthesis. As an example, one way of the synthesis and purification of Octanoyl Carnosine (Octanoyl-beta-Ala-His-OH) in its acetate salt form by solid-phase synthesis is illustrated in FIG. 1.

The Octanoyl Carnosine synthesized can be purified using standard methods (e.g., crystallization (as shown in this Example), thin layer chromatography, column chromatography, preparative HPLC, liquid-liquid extraction, etc.). Its identity can be confirmed by ESI-MS, and its purity can be determined by HPLC. Other analytical methods for peptides or lipoamino-peptides known in the art can also be used to determine the identity and purity.

Example 2

Example of Synthesis of Palmitoyl-GHK

Figure 2:
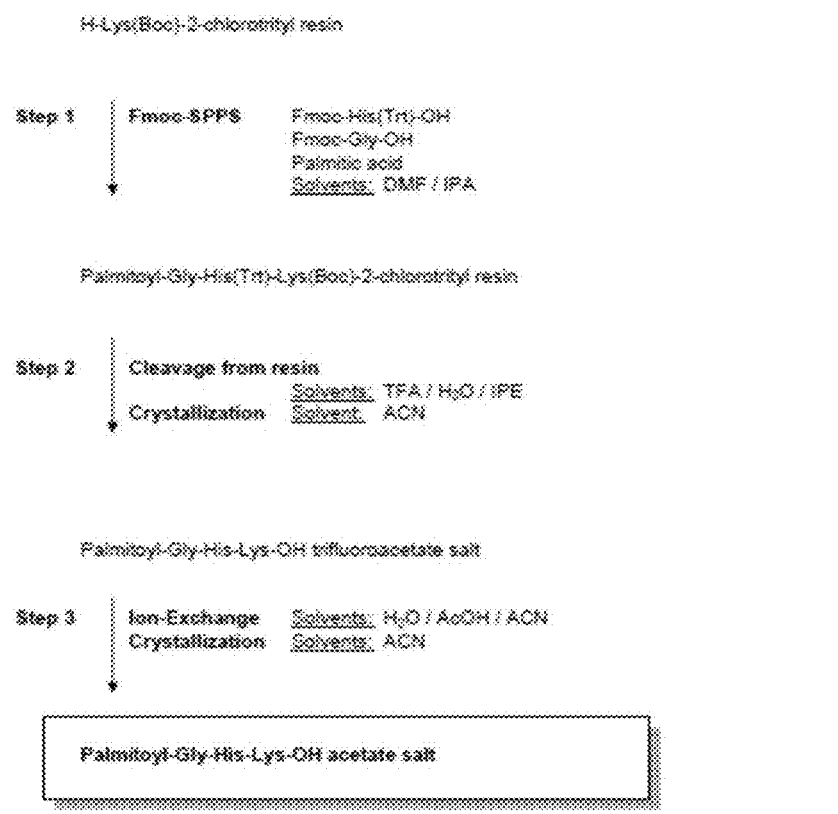
FIG. 2 is a schematic showing one way of the synthesis and purification of Palmitoyl-GHK (Palmitoyl-Gly-His-Lys-OH) in its acetate salt form by solid-phase synthesis.

The tri-peptide Palmitoyl-GHK can be prepared according to standard procedures in peptide chemistry using solid-phase synthesis or liquid-phase synthesis. As an example, one way of the synthesis and purification of Palmitoyl-GHK (Palmitoyl-Gly-His-Lys-OH) in its acetate salt form by solid-phase synthesis is illustrated in FIG. 2.

The Palmitoyl-GHK synthesized can be purified using standard methods (e.g., crystallization (as realized in this Example), thin layer chromatography, column chromatography, preparative HPLC, liquid-liquid extraction, etc.). Its identity can be confirmed by ESI-MS, and its purity can be determined by HPLC. Other analytical methods for peptides or lipoamino-peptides known in the art can also be used to determine the identity and purity.

Example 3

Example of Synthesis of Peptide GEKG (SEQ ID NO:1)

Peptide GEKG (SEQ ID NO:1) (NH$_2$-Gly-Glu-Lys-Gly-OH) (SEQ ID NO:1) can be prepared according to standard procedures in peptide chemistry using solid-phase synthesis or liquid-phase synthesis known in the art. (See, e.g., Merrifield, J. AM. CHEM. SOC. 85:2149-54 (1963) (incorporated herein by reference)).

The GEKG (SEQ ID NO:1) synthesized can be purified using standard methods (e.g., crystallization (as realized in this Example), thin layer chromatography, column chromatography, preparative HPLC, liquid-liquid extraction, etc.). Its identity can be confirmed by ESI-MS, and its purity can be determined by HPLC. Other analytical methods for peptides or lipoamino-peptides known in the art can also be used to determine the identity and purity.

Example 4

Preparation of Compositions

This Example illustrates the preparation of a series of compositions suitable for topical application in accordance to the present invention. These compositions may contain Octanoyl Carnosine (or one or more derivatives thereof) alone in a carrier acceptable for topical applications; the combination of both Octanoyl Carnosine and GEKG (SEQ ID NO:1) (or one or more derivatives thereof); the combination of both Octanoyl Carnosine and Palmitoyl-GHK (or one or more derivatives thereof); and/or the combination of Octanoyl Carnosine, GEKG (SEQ ID NO:1) and Palmitoyl-GHK (or one or more derivatives thereof). In addition, any of the compositions may also include one or more additional substances and/or one or more acceptable carriers and/or excipients suitable for topical applications.

The peptides Octanoyl Carnosine, Palmitoyl-GHK, GEKG (SEQ ID NO:1) (as well as their derivatives) can be synthesized in accordance with the methods described in Examples 1, 2 and 3, respectively. Alternatively, they can be obtained by different processes of synthesis and purifications known in the art. Octanoyl Carnosine, Palmitoyl-GHK, GEKG (SEQ ID NO:1) (or their derivatives) may be also obtained from any peptide manufacturer or supplier; either in solid form (i.e., as salt at high purity; e.g., larger than 75%, ideally larger than 90%, and more ideally larger than 95%), or already solubilzed in a simple and acceptable solvent, excipient, and/or carrier suitable for topical application (e.g., water, glycerin, propylene glycol, butylene glycol, hexylene glycol, low molecular weight PEGs such as PEG-400, and/or any mixtures thereof; with or without suitable surfactants helping to solubilize and stabilize the peptides; and/or with or without anti-microbial preservatives; and/or with or without chemical stabilizers including antioxidants or iron chelators).

Preferably, Octanoyl Carnosine (or one or more derivatives thereof) is present in the compositions in proportions of between 0.0001% and 10% of the total weight of the composition, more preferably between 0.001% and 5%, and even more preferably between 0.005% and 1%, depending on the use of the composition and the more or less potent effect sought. Thus, one of the preferred composition contains Octanoyl Carnosine (or one or more derivatives thereof) in proportions of between 0.005% and 1% in a carrier acceptable for topical application.

The compositions according to the invention can be prepared by adding Octanoyl Carnosine (or one or more derivatives thereof), either in its solid form, or solubilized in a suitable solvent, excipient, or carrier suitable for topical application, at any stage of the preparation process of the composition. Typically, however, Octanoyl Carnosine (or one or more derivatives thereof) is added as part of the aqueous phase during the preparation process of the composition. For instance in case of oil-in-water type compositions, hydrogels, and aqueous systems, Octanoyl Carnosine (or one or more derivatives thereof) can be added as the last step to the previously prepared bulk of the composition by mixing or homogenizing (e.g., using a mixer or homogenizer) Octanoyl Carnosine (or one or more derivatives thereof), which has been previously solubilized or incorporated into a solvent, excipient, and/or carrier system, to the bulk of the composition at lower temperatures (e.g., typically below 60° C.; and ideally between about 20° to 40° C.).

For example, a solvent, excipient, and/or carrier system suitable for topical application and able to solubilize or incorporate Octanoyl Carnosine (or one or more derivatives thereof) can contain one or more of the following ingredients: water, glycerin, propylene glycol, propanediol, butylene glycol, hexylene glycol, low molecular weight PEGs such as PEG-400, cyclodextrins, ethanol, and/or any mixtures thereof. Additionally, this solvent or carrier system may further contain suitable surfactants (e.g., Tween 20, Tween 80, etc.) to help solubilize and stabilize the peptides, and/or anti-microbial preservatives to help prevent microbial growth and contamination, and/or antioxidants or iron chelators (e.g., EDTA, etc.) as chemical stabilizers. Water, glycerin, propylene glycol, propanediol, butylene glycol, cyclodextrins, and/or any mixtures thereof, are the preferred ingredients.

In most instances, the additional ingredients will include a cosmetic, dermatologically or pharmaceutically acceptable carrier either alone or in combination with other additional ingredients. The amounts of additional ingredients may range from about 90% to about 99.9999%, preferably from about 95% to about 99.999%, more preferably from about 99% to about 99.999%, of the composition. In short, the percentage of additional ingredients in the compositions of the invention depends on the percentages of Octanoyl Carnosine, Palmitoyl GHK, and/or GEKG (SEQ ID NO:1) present in a given composition (i.e., the additional ingredients make up the balance of the composition). If carriers (either singularly, such as water, or complex co-solvents) are used, they may make up the entire balance of the compositions.

When preparing compositions combining peptide Octanoyl Carnosine (or one or more derivatives thereof) with other peptides, including but not limited to peptide Palmitoyl-GHK (or one or more derivatives thereof) and/or peptide GEKG (SEQ ID NO:1) (or one or more derivatives thereof), those peptides can be adding either in their solid form, or solubilized in a suitable solvent, excipient, and/or carrier for topical application, at any stage of the composition preparation process. Often, the peptides can be added as part of the aqueous phase during the preparation process of the composition. For instance in case of oil-in-water type compositions, hydrogels, and aqueous systems, the peptides can be added as the last step to the previously prepared bulk of the composition by mixing the peptides, which have been previously incorporated into a solvent, excipient, and/or carrier for topical application, to the bulk of the composition at lower temperatures (e.g., typically below 60.degree. C.; and ideally between about 20.degree. to 40.degree. C.). For example, a solvent, excipient, and/or carrier suitable to incorporate the peptides into the composition can include one or more of the following ingredients: water, glycerin, propylene glycol, propanediol, butylene glycol, hexylene glycol, low molecular weight PEGs such as PEG-400, cyclodextrins, ethanol, and/or any mixtures thereof. Additionally, this solvent, excipient and/or carrier may further contain suitable surfactants (e.g., Tween 20, Tween 80, etc.) to help solubilize and stabilize the peptides, and/or anti-microbial preservatives to help prevent microbial growth and contamination, and/or antioxidants or iron chelators (e.g., EDTA, etc.) as chemical stabilizers.

Water, glycerin, propylene glycol, propanediol, butylene glycol, cyclodextrins, and/or any mixtures thereof are the preferred ingredients.

However, when preparing compositions combining peptides which are not or poorly water soluble, or if the peptides cannot be solubilized as described above using suitable solvents, excipients, and/or carrier known to the person of skill in the art, the peptides can be added as part of the oil phase during the preparation process of the composition. Thereby, the peptides can be either added to the oil phase in their solid form, or solubilized in a suitable solvent or carrier system (e.g., oils) suitable for topical application and able to solubilize or incorporate the peptides.

Alternatively, instead of at the end of the preparation process of an oil-in-water composition for example, Octanoyl Carnosine (or one or more derivatives thereof) may be added already at an earlier step in the process. Thereby, Octanoyl Carnosine (or one or more derivatives thereof) can be added when preparing the water phase of the composition; either in its solid form, or solubilized in a suitable solvent or carrier system for Octanoyl Carnosine (or one or more derivatives thereof).

When combining Octanoyl Carnosine (or one or more derivatives thereof) with both Palmitoyl-GHK (or one or more derivatives thereof) and GEKG (SEQ ID NO:1) (or one or more derivatives thereof), the optimal weight ratio of Octanoyl Carnosine (or one or more derivatives thereof) to Palmitoyl-GHK (or one or more derivatives thereof) to GEKG (SEQ ID NO:1) (or one or more derivatives thereof) is 4 parts Octanoyl Carnosine (or one or more derivatives thereof): 1 part Palmitoyl-GHK (or one or more derivatives thereof): 5 parts GEKG (SEQ ID NO:1) (or one or more derivatives thereof) (parts refer to parts per weight), as discovered during in vitro studies for hyaluronic acid formation (see Example 5, infra). Thus, one of the preferred composition contains Octanoyl Carnosine (or one or more derivatives thereof), Palmitoyl-GHK (or one or more derivatives thereof) and GEKG (SEQ ID NO:1) (or one or more derivatives thereof) at a weight ratio of 4:1:5; whereas Octanoyl Carnosine (or one or more derivatives thereof) is present in the compositions in proportions between 0.001% and 1%, in a carrier or excipient acceptable for topical application.

In accordance to the present invention, the following illustrates suitable compositions for topical applications containing either 0.01%, 0.013%, 0.02%, or 0.1% of the combination of Octanoyl Carnosine, Palmitoyl-GHK and GEKG (SEQ ID NO:1) (or one or more derivatives thereof) at a weight ratio of 4:1:5.

Furthermore, also in accordance to the present invention, the following also illustrates suitable compositions for topical applications containing either 0.01%, 0.1%, 0.25%, 0.5%, 1%, or 5% of Octanoyl Carnosine (or one or more derivatives thereof).

Provided herein is information on the preparation of such exemplary compositions. However, the person of skill in the art will understand that any other suitable methods can also be used to prepare compositions in accordance with the instant invention.

The compositions obtained as described in the following were tested for physicochemical stability (including, but not limited to, changes in color, odor, viscosity, pH, and/or appearance) under accelerated conditions (40° C. to 50° C.) for up to three to six months. During this period, the compositions were stable; meaning that the color, odor, viscosity, pH, and the appearance did not change, or only changed to a limited and acceptable extent (±10% from baseline). If indicated, testing for chemical stability of the drug actives (e.g., OTC drug actives such as sunscreen actives, hydroquinone, retinoic acid, acne drug active, rosacea drug active, etc.) in the compositions were additionally realized by acceptable analytical methods (e.g., by HPLC, etc.).

The local tolerability (irritant and allergic contact dermatitis potential) of the compositions provided herein was determined by patch tests with challenge (repeated insult patch test) on the back of humans, and, during in use tests for few of the compositions. Those tests revealed that these compositions are of acceptable local tolerability. This means that the compositions intended for cosmetic, feminine, personal care or hygiene use are neither contact irritants nor contact allergens. The compositions intended for pharmaceutical use (i.e., medicaments) are of a negligible to minor potential for inducing irritant and allergic contact dermatitis in humans. Accordingly, those compositions are suitable for topical use since they were shown to be stable and of acceptable local tolerability.

The compositions can be filled into suitable packaging (containers) such as, for example, tubes, pumps, airless pumps, jars, bottles, pens, aerosol containers, or other containers depending on use and administration. The compositions are generally commercialized in those containers.

Composition A1: Example of a Serum Containing 0.1% of Octanoyl Carnosine

A serum containing 0.1% of Octanoyl Carnosine containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition A2: Example of a Serum Containing 0.25% of Octanoyl Carnosine

A serum containing 0.25% of Octanoyl Carnosine containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition A3: Example of a Serum Containing 0.5% of Octanoyl Carnosine

A serum containing 0.5% of Octanoyl Carnosine containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition A4: Example of a Serum Containing 1% of Octanoyl Carnosine

A serum containing 1% of Octanoyl Carnosine containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition A5: Example of a Serum Containing 5% of Octanoyl Carnosine

A serum containing 5% of Octanoyl Carnosine containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition B1: Example of Oil-in-Water Cream Containing 0.01% of Octanoyl Carnosine An oil-in-water cream containing 0.01% Octanoyl Carnosine, free of parabens and triethanolamine, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition B2: Example of Oil-in-Water Cream Containing 0.1% of Octanoyl Carnosine An oil-in-water cream containing 0.1% Octanoyl Carnosine, free of parabens and triethanolamine, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition B3: Example of Oil-in-Water Cream Containing 0.5% of Octanoyl Carnosine An oil-in-water cream containing 0.5% Octanoyl Carnosine, free of parabens and triethanolamine, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition B4: Example of Oil-in-Water Cream Containing 1% of Octanoyl Carnosine An oil-in-water cream containing 1% Octanoyl Carnosine, free of parabens and triethanolamine, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition B5: Example of Oil-in-Water Cream Containing 5% of Octanoyl Carnosine An oil-in-water cream containing 5% Octanoyl Carnosine, free of parabens and triethanolamine, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition C: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, hydrogenated peanut oil, glycerin, cetearyl ethylhexanoate, cetearyl alcohol, PEG-8 C12-18 alkyl ester, PPG-25-laureth-25, PEG-5 pentaerythrityl ether, hydroxyethylcellulose, cetyl alcohol, cetyl palmitate, glyceryl stearate, sodium chloride, ascorbyl palmitate, glucose, simethicone, tocopheryl acetate, citric acid, ricinoleth-40, potassium chloride and magnesium chloride. The cream further contained a mixture of metylparaben, propylparaben and imidazolidinyl urea for antimicrobial preservation.

Composition D1: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, octyldodecanol, glyceryl stearate decyl oleate, glycerin, propylene glycol, *triticum vulgare* (wheat germ oil), stearic acid, cetyl alcohol, ceteareth 20, myreth-3 myristate, ceteareth 12, cetearyl alcohol, cetyl palmitate, tocopheryl acetate, dimethicone, *borago officinalis* (borage seed oil), carbomer, triethanolamine, methylparaben, propylparaben, glycosphingolipids (e.g., from *Triticum vulgare* (wheat) seed extract), disodium EDTA and BHT.

The cream further contained a mixture of phenoxyethanol, ethylparaben, butylparaben, methyl-isothiazolinone and methylchloroisothiazolinone for antimicrobial preservation.

Composition D2: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, octyldodecanol, glyceryl stearate decyl oleate, glycerin, propylene glycol, *triticum vulgare* (wheat germ oil), stearic acid, cetyl alcohol, ceteareth 20, myreth-3 myristate, ceteareth 12, cetearyl alcohol, cetyl palmitate, tocopheryl acetate, dimethicone, *borago officinalis* (borage seed oil), carbomer, triethanolamine, methylparaben, sodium methylparaben, propylparaben, ethylparaben, butylparaben, glycosphingolipids (e.g., from *Triticum vulgare* (wheat) seed extract), disodium EDTA and BHT.

Composition E: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, octyldodecanol, glyceryl stearate decyl oleate, glycerin, propylene glycol, *triticum vulgare* (wheat germ oil), stearic acid, cetyl alcohol, ceteareth 20, myreth-3 myristate, ceteareth 12, cetearyl alcohol, cetyl palmitate, tocopheryl acetate, dimethicone, *borago officinalis* (borage seed oil), carbomer, methylparaben, propylparaben, glycosphingolipids (e.g., from *Triticum vulgare* (wheat) seed extract), and disodium EDTA. The cream further contained tocopherol, sodium hydroxide, and a mixture of phenoxyethanol, ethylparaben, butylparaben for antimicrobial preservation.

Composition F: Example of Oil-in-Water Cream Containing 0.013% Total Peptides

An oil-in-water cream containing 0.013% of the combination of Octanoyl Carnosine, Palmitoyl-GHK and GEKG (SEQ ID NO:1) at a weight ratio 4:1:5 was prepared as described above and contained the following other components in order of descending predominance: water, caprylic/capric triglyceride, C12-20 acid PEG-8 ester, butylene glycol, glycerin, saccharide isomerate, PEG-8, cetyl alcohol, caprylyl glycol, potassium cetyl phosphate, carbomer, bisabolol, ascorbyl tetraisopalmitate, caffeine, disodium EDTA, phospholipids, glycyrrhetinic acid, sodium hyaluronate, sodium polyacrylate, citric acid, propylparaben, tocopherol, beech tree bud extract (*fagus sylvatica* extract), palm oil (*elaeis guineensis*), tocotrienols, ascorbyl palmitate, squalene, ascorbic acid and phytosterols. The cream further contained a mixture of phenoxyethanol, methylparaben, butylparaben, and ethylparaben for antimicrobial preservation.

Composition G: Example of Oil-in-Water Cream Containing 0.013% Total Peptides

An oil-in-water cream containing 0.013% of the combination of Octanoyl Carnosine, Palmitoyl-GHK and GEKG (SEQ ID NO:1) at a weight ratio 4:1:5 was prepared as described above and contained the following other components in order of descending predominance: WATER, C12-20 ACID PEG-8 ESTER, PETROLATUM, CAPRYLIC/CAPRIC TRIGLYCERIDE, HYDROGENATED POLYISOBUTENE, GLYCERIN, SACCHARIDE ISOMERATE, HYDROXYETHYL ACRYLATE/SODIUM ACRYLOYLDIMETHYL TAURATE COPOLYMER, BUTYLENE GLYCOL, ETHYLHEXYLGLYCERIN, ISOHEXADECANE, POTASSIUM CETYL PHOSPHATE, *DIOSCOREA VILLOSA* (WILD YAM) ROOT EXTRACT, BISABOLOL, ASCORBYL TETRAISOPALMITATE, CAFFEINE, DISODIUM EDTA, PHOSPHOLIPIDS, GLYCYRRHETINIC ACID, SODIUM HYALURONATE, ACRYLATES/C10-30 ALKYL ACRYLATE CROSSPOLYMER, CITRIC ACID, SODIUM CITRATE, SODIUM HYDROXIDE, TOCOPHEROL, BEECH TREE BUD EXTRACT (*FAGUS SYLVATICA* EXTRACT), PALM OIL (*ELAEIS GUINEENSIS*), TOCOTRIENOLS, SQUALENE, PHYTOSTEROLS, PHENOXYETHANOL, CHLORPHENESIN, POLYSORBATE 60, BENZYL ALCOHOL, BENZOIC ACID Composition H: Example of Oil-in-Water Cream Containing 0.01% Total Peptides An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, caprylic/capric triglyceride, C12-20 acid PEG-8 ester, coco-caprylate/caprate, butylene glycol, dimethicone, phenyl trimethicone, biosaccharide gum-1, glycerin, cetyl alcohol, phenoxyethanol, saccharide isomerate, carbomer, potassium cetyl phosphate, *borago officinalis* (borage seed oil), ascorbyl tetraisopalmitate, caprylyl glycol, methylparaben, disodium EDTA, *chondrus crispus* (carrageenan), sodium hyaluronate, *elaeis guineensis* (palm) oil, tocotrienols, phytosterols, butylparaben, ethylparaben, PEG-8, isobutylparaben, propylparaben, tocopherol, citric acid, ascorbyl palmitate, squalene and ascorbic acid.

Composition I: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 was prepared as described above and contained the following other components in order of descending predominance: water, ethylhexyl methoxycinnamate, C12-20 acid PEG-8 ester, caprylic/capric triglyceride, coco-caprylate/caprate, butylene glycol, butyl methoxydibenzoylmethane, cetyl alcohol, biosaccharide gum-1, glycerin, C12-15 alkyl benzoate, saccharide isomerate, phenoxyethanol, caprylyl glycol, titanium dioxide, potassium cetyl phosphate, carbomer, *borago officinalis* seed oil, ascorbyl tetraisopalmitate, methylparaben, sodium hydroxide, disodium EDTA, *chondrus crispus* (carrageenan), sodium hyaluronate, *elaeis guineensis* (palm) oil, tocotrienols, phytosterols, butylparaben, aluminum stearate, polyhydroxystearic acid, ethylparaben, alumina, PEG-8, isobutylparaben, propylparaben, tocopherol, citric acid, BHT, ascorbyl palmitate, squalene and ascorbic acid.

Composition J: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 which provides additionally sun protection (e.g., of about SPF30) properties due to the presence of sunscreen actives including octinoxate and zinc oxide was prepared as described above and contained the following other components: sunscreens actives: octinoxate (about 7.5%) and zinc oxide (about 7.3%). Remaining ingredients in order of descending predominance: Water, Caprylic/Capric Triglyceride, Hydrogenated C6-14 Olefin Polymers, Hexyldecanol, Glycerin, Glyceryl Stearate, PEG-100 Stearate, Potassium Cetyl Phosphate, Hydrogenated Palm Glycerides, Microcrystalline Cellulose, *Camelia Sinensis* Extract, Silica, Sodium Ascorbyl Phosphate, Tocopheryl Acetate, Squalane, Hydroxyethyl Acrylate/Sodium Acryloyldimethyl Taurate Copolymer, Polyhydroxystearic Acid, Steareth-21, Melanin, Cetearyl Alcohol, Sodium Hyaluronate, Polysorbate 60, Triethoxycaprylsilane, Disodium EDTA, Xanthan Gum, Styrene/Acrylates Copolymer, Phenoxyethanol, Methylparaben, Ethylparaben, Propylparaben.

Composition K: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5, free of parabens, triethanolamine and BHT, was prepared as described above and contained the following other components in order of descending predominance: water, octyldodecanol, decyl oleate, glyceryl stearate, propanediol, glycerin, stearic acid, *Triticum vulgare* (wheat) germ oil, ceteareth-20, cetyl alcohol, *Borago officinalis* (borage) seed oil, dimethicone, *Triticum vulgare* (wheat) seed extract, myreth-3 myristate, ceteareth-12, tocopheryl acetate, tocopherol, cetearyl alcohol, cetyl palmitate, carbomer, disodium EDTA, sodium hydroxide, phenoxyethanol, ethylhexylglycerin, hexylene glycol, and caprylyl glycol.

Composition L: Example of Oil-in-Water Serum Containing 0.02% Total Peptides (Excluding TRIFLUORACETYL TRIPEPTIDE-2 which is Present in this Composition as an Additional Peptide)

An oil-in-water serum containing 0.02% of the combination of Octanoyl Carnosine, Palmitoyl-GHK and GEKG (SEQ ID NO:1) at a weight ratio 4:1:5 was prepared as described above and contained the following other components in order of descending predominance: WATER, GLYCERIN, CAPRYLIC/CAPRIC TRIGLYCERIDE, HYDROXYETHYL ACRYLATE/SODIUM ACRYLOYLDIMETHYL TAURATE COPOLYMER, PULLULAN, SQUALANE, AMINOPROPYL ASCORBYL PHOSPHATE, BUTYLENE GLYCOL, SODIUM HYALURONATE, ACETYL GLUCOSAMINE, ARGININE, PROLINE, GLYCINE, GLUTAMINE, TRIFLUORACETYL TRIPEPTIDE-2, ALGAE EXTRACT, POLYSORBATE 60, DEXTRAN, ETHYLHEXYLGLYCERIN, ETHYLENE/ACRYLIC ACID COPOLYMER, DISODIUM EDTA, SODIUM HYDROXIDE, CHLORPHENESIN, PHENOXYETHANOL Composition M: Example of Oil-in-Water Serum Containing 0.1% Total Peptides (Excluding TRIFLUORACETYL TRIPEPTIDE-2 which is Present in this Composition as an Additional Peptide)

An oil-in-water serum containing 0.1% of the combination of Octanoyl Carnosine, Palmitoyl-GHK and GEKG (SEQ ID NO:1) at a weight ratio 4:1:5 was prepared as described above and contained the following other components in order of descending predominance: WATER, GLYCERIN, CAPRYLIC/CAPRIC TRIGLYCERIDE, HYDROXYETHYL ACRYLATE/SODIUM ACRYLOYLDIMETHYL TAURATE COPOLYMER, PULLULAN, SQUALANE, AMINOPROPYL ASCORBYL PHOSPHATE, BUTYLENE GLYCOL, SODIUM HYALURONATE, ACETYL GLUCOSAMINE, ARGININE, PROLINE, GLYCINE, GLUTAMINE, TRIFLUORACETYL TRIPEPTIDE-2, ALGAE EXTRACT, POLYSORBATE 60, DEXTRAN, ETHYLHEXYLGLYCERIN, ETHYLENE/ACRYLIC ACID COPOLYMER, DISODIUM EDTA, SODIUM HYDROXIDE, CHLORPHENESIN, PHENOXYETHANOL Composition N: Example of Oil-in-Water Lotion Containing 0.01% Total Peptides An oil-in-water lotion containing 0.01% of the combination of Octanoyl Carnosine, Palmitoyl-GHK and GEKG (SEQ ID NO:1) at a weight ratio 4:1:5 which provides additional anti-properties due to the presence of retinol (e.g., embedded in microcapsules for controlled release) was prepared as described above and contained the following other components in order of descending predominance: Water, Caprylic/Capric Triglyceride, Glycerin, Cetearyl Alcohol, C10-30 Cholesterol/Lansterol Esters, Cetyl Ricinoleate, Cetyl Alcohol, Dimethicone, Polysorbate 60, Methyl Methacrylate/Glycol Dimethacrylate Crosspolymer, Benzyl Alcohol, Retinol, Ascorbic Acid, Ascorbyl Palmitate, Bisabolol, Tocopheryl Acetate, Cyclopentasiloxane, Cyclohexasiloxane, PEG-10 Soy Sterol, Stearic Acid, BHT, Propyl Gallate, Disodium EDTA, Magnesium Aluminum Silicate, Phenoxyethanol, Polysorbate 20, Triethanolamine, and Methylparaben.

Composition O1: Example of a Serum Containing 0.01% Total Peptides

An serum containing 0.01% of the combination of Octanoyl Carnosine, Palmitoyl-GHK and GEKG (SEQ ID NO:1) at a weight ratio 4:1:5 and containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition O2: Example of a Serum Containing 0.1% Total Peptides

An serum containing 0.1% of the combination of Octanoyl Carnosine, Palmitoyl-GHK and GEKG (SEQ ID NO:1) at a weight ratio 4:1:5 and containing high levels of hyaluronic acid was prepared as described above and contained the following other components in order of descending predominance: WATER, SODIUM HYALURONATE, CITRIC ACID, PHENOXYETHANOL, SODIUM METHYLPARABEN, SODIUM BUTYLPARABEN, SODIUM PROPYLPARABEN, and SODIUM CHLORIDE.

Composition P: Example of a Gel Containing 0.01% Total Peptides

A gel (e.g., hydrogel) containing 0.01% of the combination of Octanoyl Carnosine, Palmitoyl-GHK and GEKG (SEQ ID NO:1) at a weight ratio 4:1:5 was prepared as described above and contained the following other components in order of descending predominance: WATER (AQUA), BUTYLENE GLYCOL, GLYCERIN, CARBOMER, PEG-8, CAPRYLYL GLYCOL, CARRAGEENAN (*CHONDRUS CRISPUS*), PHENOXYETHANOL, DISODIUM EDTA, METHYLPARABEN, BUTYLPARABEN, SODIUM HYALURONATE, ETHYLPARABEN, SODIUM POLYACRYLATE, ISOBUTYLPARABEN, and PROPYLPARABEN.

Composition Q: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 which provides additionally skin lightening properties due to the presence of skin lighting agents (as disclosed in WO 2010/083368) was prepared as described above and contained the following other components:

| NO. | PHASE | INGREDIENT (TRADE NAME) | INCI DESIGNATION | SUPPLIER | % BY WEIGHT |
|---|---|---|---|---|---|
| 1 | A | DEIONIZED WATER | WATER (AQUA) | | 63.30 |
| 2 | A | NA₂EDTA | DISODIUM EDTA | AKZO/ DEWOLF | 0.100 |
| 3 | A | KELTROL CG-T | XANTHAN GUM | CP KELCO/ UNIVAR | 0.300 |
| 4 | B | LIPOWAX D | CETEARYL ALCOHOL CETEARETH-20 | LIPO | 8.250 |
| 5 | B | LIPO GMS 450 | GLYCERYL STEARATE | LIPO | 6.000 |
| 6 | B | CERAPHYL 230 | DIISOPROPYL ADIPATE | ISP SUTTON | 5.000 |

-continued

| NO. | PHASE | INGREDIENT (TRADE NAME) | INCI DESIGNATION | SUPPLIER | % BY WEIGHT |
|---|---|---|---|---|---|
| 7 | B | DC TORAY FZ-3196 | CAPRYLYL METHICONE | DOW CORNING/ UNIVAR | 3.000 |
| 8 | B | DC 200 FLUID 100 CST | DIMETHICONE | DOW CORNING/ UNIVAR | 1.000 |
| 9 | B | LIPOVOL J | *SIMMONDSIA CHINENSIS* (JOJOBA) SEED OIL | LIPO | 1.000 |
| 10 | B | SHEA BUTTER HMP | *BUTYROSPERMUM PARKII* (SHEA BUTTER) | EARTH SUPPLIED PRODUCTS | 1.000 |
| 11 | B | VITAMIN E ACETATE OIL (USP, FCC) | DL-ALPHA TOCOPHERYL ACETATE | BASF/ CHEMCENTRAL | 0.200 |
| 12 | C | DEIONIZED WATER | WATER (AQUA) |  | 0.100 |
| 13 | C | ELESTAB CPN ULTRA PURE | CHLORPHENESIN | COGNIS | 0.300 |
| 14 | C | PHENOXETOL | PHENOXYETHANOL | CLARIANT | 0.600 |
| 15 | C | SEPIWHITE MSH | UNDECYLENOYL PHENYLALANINE | SEPPIC | 0.500 |
| 16 | C | SODIUM GLYCEROPHOSPHATE (Ph. Eur. 6 Ed, Item# 500012045500) | SODIUM GLYCEROPHOSPHATE | DR. PAUL LOHMANN | 3.000 |
| 17 | C | L-LEUCINE | LEUCINE | AJINOMOTO | 1.000 |
| 18 | C1 | CITRIC ACID 50% SOLUTION (TO pH 4.5-5.0) | CITRIC ACID | PCI | 1.920 |
| 19 | C2 | GLYCERIN 99.7% (USP) | GLYCERIN | ACME-HARDESTY | 2.000 |
| 20 | C2 | SYMWHITE 377 | PHENYLETHYL RESORCINOL | KAH/SYMRISE | 0.500 |
| 21 | C2 | VITAGEN | AMINOPROPYL ASCORBYL PHOSPHATE | BASF | 0.500 |
| 22 | D | SIMULGEL INS 100 | HYDROXYETHYL ACRYLATE/SODIUM ACRYLOYLDIMETHYL TAURATE COPOLYMER ISOHEXADECANE POLYSORBATE 60 | SEPPIC | 0.420 |
| TOTAL |  |  |  |  | 99.99 |

Such compositions were generally prepared in a clean and sanitized stainless steel vessel as described herein below:

PHASE A: DISPERSE KELTROL IN WATER, MIX UNTIL ALL HYDRATES;

ADD REMAINING PHASE A INGREDIENTS, HEAT TO ABOUT 75° C. WHILE MIX UNTIL ALL DISSOLVES.

PHASE B: COMBINE PHASE B INGREDIENTS IN A SEPARATE VESSEL AND MIX WHILE HEATING TO 75° C.; ONCE ALL WAXES MELT AND PHASE IS AT TEMP AND UNIFORM, SLOWLY ADD TO PHASE A; COOL TO 35° C.

PHASE C: COMBINE PHASE C INGREDIENTS WITH MECHANICAL STIRRING UNIT AND MIX WITH MODERATE AGITATION

PHASE C1: USE PHASE C1 TO ADJUST pH OF PHASE C TO 4.0-4.5

PHASE C2: COMBINE PHASE C2 AND MIX WHILE HEATING SLIGHTLY TO 40° C.; CONTINUE MIXING UNTIL POWDERS DISSOLVE THEN ADD TO PHASE C; ADD PHASE C TO BATCH WITH MODERATE AGITATION

PHASE D: ADD PHASE D TO BATCH, MIX UNTIL UNIFORM;

HOMOGENIZE THE BATCH AT 3500 RPM FOR 5 MINUTES; SWITCH TO IMPELLER MIXING; COOL TO ROOM TEMPERATURE.

Composition R: Example of Oil-in-Water Cream Containing 0.01% Total Peptides

An oil-in-water cream containing 0.01% of the combination of Octanoyl Carnosine, Palmitoyl-GHK and GEKG (SEQ ID NO:1) at a weight ratio 4:1:5 which provides additionally skin lightening properties due to the presence of skin lighting agents including hydroquinone (as disclosed in WO 2010/083368) was prepared as described above and contained the following other components:

| NO. | PHASE | INGREDIENT (TRADE NAME) | INCI DESIGNATION | SUPPLIER | % BY WEIGHT |
|---|---|---|---|---|---|
| 1 | A | DEIONIZED WATER | WATER (AQUA) | AKZO | 59.670 |
| 2 | A | NA₂EDTA | DISODIUM EDTA | AKZO | 0.100 |
| 3 | A | KELTROL CG-T | XANTHAN GUM | CP KELCO | 0.300 |
| 4 | A | ELESTAB CPN ULTRA PURE | CHLORPHENESIN | COGNIS | 0.300 |
| 5 | A | PHENOXETOL | PHENOXYETHANOL | CLARIANT | 0.600 |
| 6 | A | SEPIWHITE MSH | UNDECYLENOYL PHENYLALANINE | SEPPIC | 0.500 |
| 7 | A | SODIUM GLYCEROPHOSPHATE (Ph. Eur. 6 Ed, Item# 500012045500) | SODIUM GLYCEROPHOSPHATE | DR. PAUL LOHMANN | 3.000 |
| 8 | A | L-LEUCINE | LEUCINE | AJINOMOTO | 1.000 |
| 9 | B | LIPOWAX D | CETEARYL ALCOHOL CETEARETH-20 | LIPO | 6.000 |
| 10 | B | LIPO GMS 450 | GLYCERYL STEARATE | LIPO | 6.000 |
| 11 | B | CERAPHYL 230 | DIISOPROPYL ADIPATE | ISP SUTTON | 3.000 |
| 12 | B | DC TORAY FZ-3196 | CAPRYLYL METHICONE | DOW CORNING | 3.000 |
| 13 | B | DC 200 FLUID 100 CST | DIMETHICONE | DOW CORNING/UNIVAR | 1.000 |
| 14 | B | LIPOVOL J | *SIMMONDSIA CHINENSIS* (JOJOBA) SEED OIL | LIPO | 1.000 |
| 15 | B | SHEA BUTTER HMP | *BUTYROSPERMUM PARKII* (SHEA BUTTER) | EARTH SUPPLIED PRODUCTS | 1.000 |
| 16 | B | VITAMIN E ACETATE OIL (USP, FCC) | DL-ALPHA TOCOPHERYL ACETATE | BASF/ CHEMCENTRAL | 0.200 |
| 17 | C | CITRIC ACID 50% SOLUTION (TO pH 4.5-5.0) | CITRIC ACID | PCI | 1.920 |
| 18 | D | EASTMAN™ HYDROQUINONE (USP GRADE) | HYDROQUINONE | EASTMAN/ CHEMPOINT | 4.000 |
| 19 | E | SODIUM METABISULFITE (NF/FCC) | SODIUM METABISULFITE | UPI | 0.400 |
| 20 | F | GLYCERIN 99.7% (USP) | GLYCERIN | ACME-HARDESTY | 2.000 |
| 21 | F | SYMWHITE 377 | PHENYLETHYL RESORCINOL | KAH/SYMRISE | 0.500 |
| 22 | F | VITAGEN | AMINOPROPYL ASCORBYL PHOSPHATE | BASF | 0.500 |
| 23 | G | SIMULGEL INS 100 | HYDROXYETHYL ACRYLATE/SODIUM ACRYLOYLDIMETHYL TAURATE COPOLYMER ISOHEXADECANE POLYSORBATE 60 | SEPPIC | 4.000 |
| TOTAL | | | | | 99.99 |

Such compositions were generally prepared in a clean and sanitized stainless steel vessel, which was suitable for blending products containing hydroquinone, as described herein below:

PHASE A: DISPERSE KELTROL IN WATER, MIX UNTIL ALL HYDRATES; ADD EDTA, MIX UNTIL ALL DISSOLOVES;
ADD REMAINING PHASE A INGREDIENTS, HEAT TO 75° C. WHILE MIX UNTIL ALL DISSOLVES.
PHASE B: COMBINE PHASE B INGREDIENTS, HEAT TO 75° C., MIX UNTIL ALL MELTED AND UNIFORM;
WHEN BOTH PHASE A AND PHASE B AT 75° C., ADD PHASE B INTO PHASE A WITH AGITATION MIX FOR 10 MINUTES, START COOLING TO 50° C.
PHASE C: ADJUST pH WITH PHASE C TO pH 4.5-5.0, COOL TO 45° C.
PHASE D: ADD PHASE D TO BATCH WITH MIX, MIX UNTIL ALL DISSOLVES AND UNIFORM.
PHASE E: ADD PHASE E TO BATCH WITH MIXING, MIX UNTIL ALL DISSOLVES.
PHASE F: COMBINE PHASE F INGREDIENTS, SLIGHTLY HEAT AND MIX UNTIL ALL DISSOLVES, ADD TO THE BATCH.

PHASE G: ADD PHASE G TO BATCH, MIX UNTIL UNIFORM;
HOMOGENIZE THE BATCH AT 3500 RPM FOR 5 MINUTES, SWITCH TO IMPELLER MIXER, MIX;
ADJUST pH WITH PHASE C TO pH 4.5-5.0 IF NECESSARY.

Composition S: Example of Oil-in-Water Serum Containing 0.01% Total Peptides

An oil-in-water serum containing 0.01% of the combination of Octanoyl Carnosine, Palmitoyl-GHK and GEKG (SEQ ID NO:1) at a weight ratio 4:1:5 which provides additionally anti-rosacea or skin redness reducing properties due to the presence of antimicrobial peptide sequestering agents such as the sodium salt of dextran sulfate (as disclosed in WO 2011/109469) was prepared as described above and contained the following other components:

| Phase | Ingredient (Trade Name) | INCI Name | Supplier(s) | % by weight (% w) |
|---|---|---|---|---|
| A | Water | Water (Aqua) | | 60.03 |
| A | Na2EDTA | Disodium EDTA | Akzo/DeWolf | 0.1 |
| A | Keltrol CG-SFT | Xanthan Gum | CP Kelco/Univar | 0.25 |
| A | Structure XL | Hydroxypropyl Starch Phosphate | National Starch | 1.0 |
| A | Simulgel INS 100 | Hydroxyethyl Acrylate/Sodium Acryloyldimethyl Taurate Copolymer (and) Isohexadecane (and) Polysorbate-60 | Seppic | 1.0 |
| B | Water | | | 15 |
| B | Oristract CF | Caffeine | Orient Stars | 1.5 |
| B | Dextran Sulfate Sodium Salt (av. M.W. about 8000) | Dextran Sodium Sulfate | MP Biomedical/Spectrum | 0.5 |
| B | Ajidew ZN-100 | Zinc PCA | Ajinomoto | 1 |
| B1 | Elestab CPN Ultra Pure | Chlorphenesin | Cognis | 0.2 |
| B1 | Glycerin 99.7% | Glycerin | Acme-Hardesty | 15 |
| B1 | Phenoxetol | Phenoxyethanol | Clariant/Essential Ingredients | 0.5 |
| C | Structure XL | Hydroxypropyl Starch Phosphate | National Starch | 1.5 |
| C | Simulgel INS 100 | Hydroxyethyl Acrylate/Sodium Acryloyldimethyl Taurate Copolymer (and) Isohexadecane (and) Polysorbate-60 | Seppic | 0.41 |
| D | DC Toray FZ-3196 | Caprylyl Methicone | Dow Corning/Univar | 2 |

Such compositions were generally prepared in a clean and sanitized stainless steel vessel as described herein below:

Phase A: Dissolve Na2EDTA into agitating Phase A water. Mix until uniform. Sprinkle Keltrol slowly into batch. Mix until fully hydrated. Sprinkle Structure XL into agitating Phase A water. Mix until fully dispersed, and homogenize at 3500 RPM for 5-6 minutes. Add Simulgel INS 100 and mix until uniform, then homogenize for about 4 minutes at 3500 RPM.

Phase B: Combine Phase B ingredients, one by one in a separate vessel while heating to 50-53° Celsius (not higher than 55° Celsius).

Phase B1: In a separate vessel combine Phase B1 ingredients and heat to 40° Celsius. Mix until powder is dispersed. Add Phase B1 to Phase B and mix until clear. Cool to 30° Celsius and add combined Phase B/B1 to batch. Mix until uniform.

Phase C: Add Phase C to batch one by one to raise viscosity, homogenize after adding the Structure X1 and again after adding the Simulgel INS 100.

Phase D: Add Phase D ingredients to batch and mix until uniform.

Example 5

Results of In Vitro Tests on Examples According to the Invention

In Vitro Test 1: Stimulation of Gene Expression of Extracellular Matrix Components Including but not Limited to Collagens I and III by Octanoyl Carnosine Normal human dermal fibroblasts (NHDF); used at the $8^{th}$ passage, were cultured in culture medium (DMEM supplemented with 10% fetal calf serum, 2 mM L-glutamine, 50 U/ml penicillin, and 50 μg/ml streptomycin) in 24-well plates for 48 h at 37° C. and 5% $CO_2$ with a renewal of culture medium after 24 h. The culture medium was then removed, replaced by assay medium (DMEM culture medium supplemented with 1% fetal calf serum, 2 mM L-glutamine, 50 U/ml penicillin, and 50 μg/ml streptomycin) and the cells were further incubated for 24 h. The cells were then treated with the test peptides, or not (control), or with the reference TGF-beta 1 and incubated for 24 h. All experimental conditions were performed 4-times (n=4). At the end of the incubation, the cells were washed in PBS solution and immediately frozen at about −80° C. The expression of the markers was analyzed using quantitative real time polymerase chain reaction (RT-qPCR) method on mRNA extracted from the cell monolayers for each treatment; whereby the replicates were pooled before RNA extraction. Analysis of gene expression was performed in duplicate (n=2) using a PCR array. Total RNA was extracted from each sample using TriPure Isolation Reagent® according to the supplier's instructions. The amount and quality of RNA were evaluated using a lab-on-a-chip Bioanalyzer (Agilent Technologies). Potential contaminant traces of genomic DNA were removed using the DNAfree system (Ambion). The reverse-transcription of mRNA was conducted in presence of oligo(dT) and Superscript II reverse-transcriptase. Quantification of cDNA was performed using Nanovue (GE Healthcare) and cDNA was adjusted.

The PCRs were performed using the LightCycler® system (Roche Molecular System Inc.) according to the supplier's instructions. This system allowed rapid and powerful PCRs, after determining analysis conditions of the test primers. The reaction mix (10 µl final) was added as follows: 2.5 µl of cDNA, primers forward and reverse; and reagent mix containing taq DNA polymerase, SYBR Green I, and $MgCl_2$.

The incorporation of the fluorescence in amplified DNA was continuously measured during the PCR cycles. This resulted in a "fluorescence intensity" versus "PCR cycle" plot allowing the evaluation of a relative expression (RE) value for each marker. The value selected for RE calculations is the "output point" (Ct) of the fluorescence curve. For a considered marker, the highest is the cycle number; the lowest is the mRNA quantity. The RE value was expressed in arbitrary units (AU) according to the formula: $(1/2^{number\ of\ cycles}) \times 10^6$.

This evaluation was realized with non-cytotoxic concentrations of the test peptides. Cytotoxicity of the test peptides in the assay medium was previously determined in NHDF by the MTT reduction assay and morphological observations with help of microscope after a 24 h incubation time.

This test surprisingly revealed that the peptide Octanoyl Carnosine is able to significantly stimulate extracellular matrix components other than only collagen I. It was discovered that Octanoyl Carnosine at 300 ppm (0.03%) stimulates the formation of collagen I (alpha 1) by 38%, collagen III (alpha 1) by 120%, collagen V (alpha 1) by 35%, collagen VI (alpha 1) by 46%, collagen VII (alpha 1) by 97%, collagen XVI (alpha 1) by 91%, elastin by 51%, laminin (alpha 4) by 20%, hyaluronan synthase 2 by 23%, fibrillin 1 by 23%, and heparan sulfate protoglycan 2 by 79%.

Even more unexpectedly, this test surprisingly revealed that the peptide Octanoyl Carnosine is able to stimulate collagen III significantly more than collagen I; collagen III (alpha 1) formation was stimulated by 120%, whereas collagen I (alpha 1) only by 38%. This property of Octanoyl Carnosine was unexpected as other peptides which stimulate formation of both collagen I and collagen III generally stimulate collagen I significantly more than collagen III. For example, as also demonstrated in this test, beta-alanyl-histidine (the natural carnosine) at 300 ppm (0.03%) stimulates formation of collagen III only by 24% but stimulates collagen I at 28%. Furthermore, TGF-beta 1 (10 ng/ml) was shown to stimulate formation of collagen III by 164% but at the same time stimulates collagen I by 245%.

For the interpretation of the data related to the stimulation of the formation of extracellular matrix components as determined during the in vitro experiments, a "significant" stimulation of the formation of extracellular matrix components means a stimulation of at least 20% more than measured using a control material under identical experimental conditions. The control material is the identical material (here: assay medium) as used when testing the active (here: peptide(s)) but without the active(s).

Consequently, compositions containing Octanoyl Carnosine (or one or more derivatives thereof) according to the present invention have therefore great potential in the field of cosmetics, dermatology, wound healing, and any other areas in need of treatments for conditions, disorders and diseases where extracellular matrix components (including, but not limited to, collagen III) are altered. In addition, such compositions can be used for maintaining healthy skin, skin rejuvenation, scarless wound healing, restoration of damaged skin and mucosa, as well as for the treatment of atrophy of any human tissue including, but not limited to, vulvovaginal atrophy.

In contrast, the prior art discloses other peptides significantly stimulating both collagen I and collagen III formation, but they stimulate collagen I more than collagen III.

In Vitro Test 2: Stimulation of Hyaluronic Acid—Combination of Octanoyl Carnosine with Other Peptides Normal human dermal fibroblasts (NHDF); used at the $8^{th}$ passage, were cultured in culture medium (DMEM supplemented with 10% fetal calf serum, 2 mM L-glutamine, 50 U/ml penicillin, and 50 µg/ml streptomycin) in 96-well plates for 24 h at 37° C. and 5% $CO_2$.

Afterwards, the culture medium was removed and replaced by assay medium (DMEM culture medium supplemented with 2% fetal calf serum, 2 mM L-glutamine, 50 U/ml penicillin, and 50 µg/ml streptomycin) containing the test peptides or not (control). The cells were then incubated for 72 h. All experimental conditions were performed 3-times (n=3). At the end of the incubation, culture supernatants were collected and immediately frozen at about −80° C.

Hyaluronic acid was quantified in the culture supernatant using the Duoset Hylaluronan ELISA kit (R&D Systems Ref. DY3614, 0.37 ng/ml as low detection limit) according to the provider's specifications.

This evaluation was realized with non-cytotoxic concentrations of the test peptides. Cytotoxicity of the test peptides in the assay medium was previously determined in NHDF by the MTT reduction assay and morphological observations with help of microscope after a 72 h incubation time.

This test surprisingly revealed that the combination of Octanoyl Carnosine with both Palmitoyl-GHK and GEKG (SEQ ID NO:1) at a weight ratio of 4 parts Octanoyl Carnosine, 1 part Palmitoyl-GHK, and 5 parts GEKG (SEQ ID NO:1) stimulates synthesis of hyaluronic acid significantly more than at other ratios. We discovered that a combination of 100 ppm (0.01%) Octanoyl Carnosine, 25 ppm (0.0025%) Palmitoyl-GHK and 125 ppm (0.0125%) GEKG (SEQ ID NO:1) significantly stimulates the synthesis of hyaluronic acid by 64%.

This significant stimulation of the synthesis of hyaluronic acid using Octanoyl Carnosine when combined with Palmitoyl-GHK and GEKG (SEQ ID NO:1) at a weight ratio of 4:1:5 was unexpected, as other weight ratios did not produce similar stimulation of hyaluronic acid synthesis.

For instance, this test revealed that a combination at the same total concentration of peptides (250 ppm) at a weight ratio of 1:2:2 (Octanoyl Carnosine:Palmitoyl-GHK:GEKG (SEQ ID NO:1)) only non-significantly stimulated the synthesis of hyaluronic acid by 8%. Likewise, combinations at a weight ratio of 1:1:2 (tested at total peptide concentrations of 132 ppm and 400 ppm), 1:3:1 (166 and 500 ppm), and 1:30:1 (320 ppm) non-significantly stimulated the synthesis of hyaluronic acid by less than 20%.

Even more surprisingly, this test also revealed that the combination of Octanoyl Carnosine with both Palmitoyl-GHK and GEKG (SEQ ID NO:1) at a weight ratio of 4 parts Octanoyl Carnosine, 1 part Palmitoyl-GHK, and 5 parts GEKG (SEQ ID NO:1) stimulates synthesis of hyaluronic acid in a synergistic manner. Specifically, a combination of 100 ppm (0.01%) Octanoyl Carnosine, 25 ppm (0.0025%) Palmitoyl-GHK and 125 ppm (0.0125%) GEKG (SEQ ID NO:1) significantly stimulates the synthesis of hyaluronic acid by 64%. However, Octanoyl Carnosine alone at same concentration (100 pm) did not stimulate the synthesis of hyaluronic acid (the results show a −5% increase, which, in fact, means a non-significant inhibition of hyaluronic acid synthesis); Palmitoyl-GHK alone (at 10 or 30 ppm) non-significantly stimulated hyaluronic acid synthesis by only up to 11%; and GEKG (SEQ ID NO:1) alone (at 100 or 300 ppm) significantly stimulated hyaluronic acid synthesis but only by up to 25%.

Consequently, if the effect of the combination of these three peptides (or any derivatives thereof) was additive, one would only expect only about a 30-40% increase in hyaluronic acid synthesis (corresponding approximately to the sum of −5% plus 11% plus 25%). However, unexpectedly, the combination of Octanoyl Carnosine, Palmitoyl-GHK and GEKG (SEQ ID NO:1) at the weight ratio of 4:1:5 resulted in a stimulation hyaluronic acid formation by 64%, which demonstrates that a combination of Octanoyl Carnosine, Palmitoyl-GHK and GEKG (SEQ ID NO:1) at the weight ratio of 4:1:5 provides synergistic effects (i.e., total effect of the combination of the three peptides is greater than the sum of the effects of the three peptides alone) in the stimulation of hyaluronic acid formation.

Therefore, compositions containing Octanoyl Carnosine combined with Palmitoyl-GHK and GEKG (SEQ ID NO:1) (or one or more derivatives thereof) at the weight ratio of 4:1:5 according to the present invention have therefore great potential in the field of cosmetics, dermatology, wound healing, and any other area in the need of treatments for conditions, disorders and diseases where hyaluronic acid is altered. In addition, such compositions can be used for maintaining healthy skin, skin rejuvenation, scarless wound healing, restoration of damaged skin and mucosa, as well as for the treatment of atrophy of any human tissue including but not limited to vulvovaginal atrophy.

Example 6

Results of Clinical Tests on Examples According to the Invention

The following clinical tests with compositions according to the present invention illustrate a series of examples of the different uses of the compositions and demonstrate the suitability of the compositions for topical application in the field of cosmetics, dermatology, wound healing, and any other areas in need of treatments for conditions, disorders and diseases where extracellular matrix components (including, but not limited to, collagen III) are altered; and in particular for maintaining healthy skin, skin rejuvenation, scarless wound healing, restoration of damaged skin and mucosa, as well as for the treatment of atrophy of any human tissue including but not limited to vulvovaginal atrophy.
Clinical Test 1: Anti-Aging Study An oil-in-water cream containing 0.01% of the combination of Octanoyl Carnosine, Palmitoyl-GHK and GEKG (SEQ ID NO:1) at a weight ratio 4:1:5 (Composition D2; prepared as described in Example 4) was studied in humans for maintaining healthy skin and skin rejuvenation. The human subjects applied the cream twice daily to their face over a period of six months. They were asked to apply the cream as they would normally use a cosmetic facial product (e.g., facial moisturizer). Evaluations for safety and effectiveness were performed before the treatment with the cream started (baseline), and after 1, 2, 3 and 6 months, respectively.

The evaluations included the assessment of the subject's face by trained investigators for fine lines and coarse wrinkles in the peri-orbital area, fine lines and coarse wrinkles in the peri-oral area, tactile roughness, mottled hyperpigmentation, redness and telangiectasia, skin pores and pore size, skin tone, and for global skin damage using visual severity scores. The evaluations for effectiveness further included clinical photography of the face (under standardized conditions including position of the subject and lighting), quantification of the skin roughness and wrinkle depths of the peri-orbital skin area using the PRIMOS-3D System (GF Messtechnik GmbH, Germany; utilizing standardized measuring and lighting conditions in the 'Overlay' mode), as well as the measurement of skin elasticity of the upper cheek area with a Cutometer® MPA580 device (Courage & Khazaka, Koln, Germany; probe aperture 2 mm) after the subjects have been in a seated position in the environmentally-controlled room for at least 30 minutes. The assessment of erythema (redness), edema (swelling), dryness, and peeling (desquamation) was performed to determine the safety of the cream. For this purpose, the investigator used the following 5-point scale: 0=none, 1=mild, 2=moderate, 3=marked, 4=severe. Furthermore, adverse events were recorded during the entire study duration. In a subset of subjects, a 3 mm punch biopsy was taken from the pre-auricular skin area under local anesthesia (i.e., up to 1 cc lidocaine with epinephrine given intradermally) performed by the study doctor before treatment and at the end of the six month treatment period. The sequential biopsies were nearly adjacent to each other. The biopsy specimens were fixed in formaldehyde, embedded in standard embedding medium, and then evaluated for changes in epidermal and dermal structure (and for changes of the extracellular matrix in particular) by histology. In addition, the subjects reported about diverse attributes of the cream (benefits, improvements, tolerability, cosmetic feel, satisfaction, etc.) using questionnaires.

The following results were obtained in a study which included females of skin types I to III with at least moderate signs of facial wrinkles. Peri-orbital wrinkles improved (by at least 1 unit) in 35% of the subjects after 1 month (from 2.9±0.5 before treatment to 2.6±0.6; mean±SD, n=20 subjects), 71% after 3 months (2.1±0.6; n=17), and 88% after 6 months (1.8±0.4; n=17). Peri-oral wrinkles improved (by at least 1 unit) in 30% of the subjects after 1 month (from 2.7±0.6 before treatment to 2.4±0.6; mean±SD, n=20), 47% after 3 months (2.2±0.5; n=17), and 71% after 6 months (1.7±0.5; n=17). The product was well tolerated.

This study clearly demonstrated that an oil-in-water cream containing 0.01% of the combination of Octanoyl Carnosine, Palmitoyl-GHK and GEKG (SEQ ID NO:1) at a weight ratio 4:1:5 rejuvenates aged skin. The composition was further well tolerated in all subjects and did not cause any adverse events.
Clinical Test 2: Skin Restoration Studies after Cosmetic and Dermatological Procedures An oil-in-water cream containing 0.01% of the combination of Octanoyl Carnosine, Palmitoyl-GHK and GEKG (SEQ ID NO:1) at a weight ratio 4:1:5 (Composition E; prepared as described in Example 4) was studied in humans for enhancing the restoration of skin after cosmetic and dermatological procedures such as chemical skin peels, skin abrasion treatments, skin laser treatments, skin light treatments, skin radiofrequency treatments, skin ultrasound, cold or hot treatments of skin, non-surgical face lifts; or combinations thereof. The subjects were asked to apply the cream once to six-times daily to the affected skin area until at least the skin has healed. This study involving different clinical case trials demonstrated that an oil-in-water cream containing 0.01% of the combination of Octanoyl Carnosine, Palmitoyl-GHK and GEKG (SEQ ID NO:1) at a weight ratio 4:1:5 enhances the restoration process of skin (e.g., decrease of time to heal, reduction of severity of side effects due to procedure, reduction of skin inflammation, decrease of time for restoring normal skin barrier, decrease of time for re-epithelialization, increase of hydration, decrease of time to appear normal again, help to improve appearance, help to reduce signs of skin aging, contribution to increase collagen III formation, does not result in scar formation, etc.) after cosmetic and dermatological procedures. The composition was further well tolerated.

A serum containing 0.5% of Octanoyl Carnosine (Composition A3; prepared as described in Example 4) was studied in humans for enhancing the restoration of skin after cosmetic and dermatological procedures. The subjects were asked to apply the serum once to six-times daily to the affected skin area until at least the skin has healed. This study involving different clinical case trials demonstrated that a serum containing 0.5% of Octanoyl Carnosine enhances the restoration process of skin after cosmetic and dermatological procedures. The composition was further well tolerated.

Clinical Test 3: Wound Healing Studies

An oil-in-water cream containing 0.01% of the combination of Octanoyl Carnosine, Palmitoyl-GHK and GEKG (SEQ ID NO:1) at a weight ratio 4:1:5 (Composition D2; prepared as described in Example 4) was studied in humans for wound healing of surgical wounds, accidental wounds, skin ulcers, and skin burns. The subjects were asked to apply the cream once to six-times daily to the wounded area until at least the wound has healed. This study involving different clinical case trials demonstrated that an oil-in-water cream containing 0.01% of the combination of Octanoyl Carnosine, Palmitoyl-GHK and GEKG (SEQ ID NO:1) at a weight ratio 4:1:5 accelerates wound closure and helps skin heal without scar formation. The composition was further well tolerated.

A serum containing 0.5% of Octanoyl Carnosine (Composition A3; prepared as described in Example 4) was studied in humans for wound healing of surgical wounds, accidental wounds, skin ulcers, and skin burns. The subjects were asked to apply the serum once to six-times daily to the wounded area until at least the wound has healed. This study involving different clinical case trials demonstrated that a serum containing 0.5% of Octanoyl Carnosine accelerates wound closure and helps skin heal without scar formation. The composition was further well tolerated.

Clinical Test 4: Skin Atrophy Studies

An oil-in-water cream containing 0.01% of the combination of Octanoyl Carnosine, Palmitoyl-GHK and GEKG (SEQ ID NO:1) at a weight ratio 4:1:5 (Composition E; prepared as described in Example 4) was studied in humans with skin atrophy due to long-term topical corticosteroids use, or respectively, after menopause in women. The subjects were asked to apply the cream once to six-times daily for at least four weeks to the affected skin area. This study involving different clinical case trials demonstrated that an oil-in-water cream containing 0.01% of the combination of Octanoyl Carnosine, Palmitoyl-GHK and GEKG (SEQ ID NO:1) at a weight ratio 4:1:5 reduce the severity of skin atrophy and helps restore a normal skin barrier. The composition was further well tolerated.

A serum containing 0.5% of Octanoyl Carnosine (Composition A3; prepared as described in Example 4) was studied in humans with skin atrophy due to long-term topical corticosteroids use, or respectively, after menopause in women. The subjects were asked to apply the serum once to six-times daily for at least four weeks to the affected skin area. This study involving different clinical case trials demonstrated that a serum containing 0.5% of Octanoyl Carnosine reduces the severity of skin atrophy and helps restore a normal skin barrier. The composition was further well tolerated.

Clinical Test 5: Vulvovaginal Atrophy Studies

An oil-in-water cream containing 0.01% of the combination of Octanoyl Carnosine, Palmitoyl-GHK and GEKG (SEQ ID NO:1) at a weight ratio 4:1:5 (Composition K; prepared as described in Example 4) was studied in women with vulvovaginal atrophy. In those women, vulvovaginal atrophy was due to menopause (either naturally occurring, or surgically induced), use of oral contraceptives, when undergoing breast cancer treatments (e.g., including taking aromatase inhibitors), or due to other causes altering their human sex hormone levels. The women were asked to apply the cream once to four-times daily for at least four weeks to their vulva by using their index finger. This study involving different clinical case trials demonstrated that an oil-in-water cream containing 0.01% of the combination of Octanoyl Carnosine, Palmitoyl-GHK and GEKG (SEQ ID NO:1) at a weight ratio 4:1:5 reduces the severity of the symptoms associated with vulvovaginal atrophy (e.g., dryness of vulva, feel of rawness, discomfort, pain with sex, itch, etc.) as well as reduces the severity of vulvovaginal atrophy; in particular for the vulva.

Clinical Test 6: Studies in Other Conditions, Disorders and Diseases where Extracellular Matrix Components are Altered Compositions according to the present invention were also studied for the treatment of other conditions, disorders and diseases where extracellular matrix components are altered including atopic dermatitis, eczema, scars and keloids, atrophie blanche, vulvar lichen sclerosus, epidermolysis bullosa, Ehlers-Danlos syndromes, and the Marfan syndrome. The subjects were asked to apply the compositions between once to six-times daily for at least four weeks to the affected skin area. This study involving different clinical case trials demonstrated that the compositions help reduce the symptoms and the severity of those conditions, disorders and diseases. The composition was generally well tolerated.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

I claim:

1. A composition for stimulating the formation of one or more extracellular matrix components in skin or mucosa, comprising N-Octanoyl carnosine, the lipoaminoacid derivative of the tripeptide GHK (N-Palmitoyl-GHK), and the tetrapeptide GEKG (SEQ ID NO:1) at a weight ratio of 4:1:5, wherein the composition is formulated for topical or subcutaneous administration.

2. The composition of claim 1, wherein the composition further comprises one or more carriers or excipients suitable for topical administration or subcutaneous administration.

3. The composition of claim 2, wherein the composition stimulates the formation of one or more extracellular matrix components selected from the group consisting of collagen I, collagen III, collagen V, collagen VI, collagen VII, collagen XVI, elastin, laminin, hyaluronic acid, fibrillin, heparan sulfate proteoglycan 2, and combinations thereof.

4. The composition of claim 3, wherein the composition additionally stimulates the formation of one or more extracellular matrix components predominantly associated with skin aging selected from the group consisting of collagen I, collagen VII, elastin, hyaluronic acid, and combinations thereof.

5. The composition of claim 3, wherein the composition stimulates formation of hyaluronic acid.

6. The composition of claim 2, wherein the composition is suitable for topical administration in humans on skin, aged skin, damaged skin, skin after cosmetic and dermatological procedures, atrophic skin, atrophic mucosa, wounded skin, vulva, vagina, atrophic vulva, atrophic vagina, vulvovaginal atrophy.

7. The composition of claim 5, wherein the composition is suitable for topical administration in humans on skin, aged skin, damaged skin, skin after cosmetic and dermatological procedures, atrophic skin, wounded skin, vulva, vagina, atrophic vulva, atrophic vagina.

8. The composition of claim 5, wherein the combination of N-Octanoyl Carnosine, tripeptide, and tetrapeptide stimulates the production of extracellular matrix components in skin or epithelial cells to a greater degree than any one or two active ingredients alone.

9. The composition of claim 2, wherein the composition comprises between about 0.0001% to 10% per weight of N-Octanoyl Carnosine.

10. The composition of claim 8, wherein the composition comprises between about 0.0001% to 10% per weight of N-Octanoyl Carnosine.

11. The composition of claim 2, wherein the composition comprises about 0.004% per weight of N-Octanoyl Carnosine; about 0.001% per weight of Palmitoyl-GHK, and about 0.005% per weight of GEKG (SEQ ID NO:1), and one or more acceptable carriers or excipients suitable for topical application in humans on skin, aged skin, damaged skin, skin after cosmetic and dermatological procedures, wounded skin, atrophic skin, atrophic mucosa, atrophic vulva, atrophic vagina.

12. A pharmaceutical composition comprising the composition of claim 2 and one or more pharmaceutically acceptable carriers.

13. A cosmetic composition comprising the composition of claim 1 and one or more cosmetically acceptable carriers.

14. A kit comprising, in one or more containers, the pharmaceutical composition of claim 12 and instructions for use.

15. A kit comprising, in one or more containers, the cosmetic composition of claim 13 and instructions for use.

* * * * *

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthesized peptide

<400> SEQUENCE: 1

Gly Glu Lys Gly
1

<210> SEQ ID NO 2
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (2)..(3)
<223> OTHER INFORMATION: Xaa can be any amino acid

<400> SEQUENCE: 2

Gly Xaa Xaa Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (2)..(3)
<223> OTHER INFORMATION: Xaa can be any amino acid

<400> SEQUENCE: 3

Pro Xaa Xaa Pro
1

<210> SEQ ID NO 4
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (2)..(3)
<223> OTHER INFORMATION: Xaa can be any amino acid

<400> SEQUENCE: 4

Pro Xaa Xaa Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthesized peptide

<400> SEQUENCE: 5

Gly Glu Pro Gly
1

```
<210> SEQ ID NO 6
<211> LENGTH: 4
<212> TYPE: PRT
<213> ORGANISM: Artificial Sequence
<220> FEATURE:
<223> OTHER INFORMATION: Synthesized peptide

<400> SEQUENCE: 6

Gly Pro Pro Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthesized peptide

<400> SEQUENCE: 7

Pro Gly Pro Pro
1

<210> SEQ ID NO 8
<211> LENGTH: 4
<212> TYPE: PRT
<213> ORGANISM: Artificial Sequence
<220> FEATURE:
<223> OTHER INFORMATION: Synthesized peptide

<400> SEQUENCE: 8

Pro Lys Glu Lys
1

<210> SEQ ID NO 9
<211> LENGTH: 4
<212> TYPE: PRT
<213> ORGANISM: Artificial Sequence
<220> FEATURE:
<223> OTHER INFORMATION: Synthesized peptide

<400> SEQUENCE: 9

Gly Gln Pro Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthesized peptide

<400> SEQUENCE: 10

Arg Ser Arg Lys
1

<210> SEQ ID NO 11
<211> LENGTH: 5
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: A palmitoyl group may be attached to the Lys
      residue

<400> SEQUENCE: 11
```

```
Lys Thr Thr Lys Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized peptide

<400> SEQUENCE: 12

Val Gly Val Ala Pro Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: A palmitoyl group is attached to the Tyr
      residue
<220> FEATURE:
<221> NAME/KEY: MISC_FEATURE
<222> LOCATION: (5)..(5)
<223> OTHER INFORMATION: Xaa can be any amino acid.

<400> SEQUENCE: 13

Tyr Gly Gly Phe Xaa
1               5
```